US009828384B2

(12) United States Patent
Lowe, III et al.

(10) Patent No.: US 9,828,384 B2
(45) Date of Patent: Nov. 28, 2017

(54) SPIRO-LACTAM NMDA RECEPTOR MODULATORS AND USES THEREOF

(71) Applicant: Aptinyx Inc., Evanston, IL (US)

(72) Inventors: John A. Lowe, III, Stonington, CT (US); M. Amin Khan, Evanston, IL (US)

(73) Assignee: Aptinyx Inc., Evanston, IL (US)

( * ) Notice: Subject to any disclaimer, the term of this patent is extended or adjusted under 35 U.S.C. 154(b) by 0 days.

(21) Appl. No.: 14/764,402

(22) PCT Filed: Jan. 29, 2014

(86) PCT No.: PCT/US2014/013621
§ 371 (c)(1),
(2) Date: Jul. 29, 2015

(87) PCT Pub. No.: WO2014/120784
PCT Pub. Date: Aug. 7, 2014

(65) Prior Publication Data
US 2015/0368252 A1 Dec. 24, 2015

Related U.S. Application Data

(60) Provisional application No. 61/757,920, filed on Jan. 29, 2013.

(51) Int. Cl.
*C07D 487/10* (2006.01)
*A61K 31/397* (2006.01)

(52) U.S. Cl.
CPC ................................ *C07D 487/10* (2013.01)

(58) Field of Classification Search
None
See application file for complete search history.

(56) References Cited

U.S. PATENT DOCUMENTS

| | | | |
|---|---|---|---|
| 4,904,681 A | 2/1990 | Cordi et al. | |
| 4,959,493 A | 9/1990 | Ohfume et al. | |
| 5,061,721 A | 10/1991 | Cordi et al. | |
| 5,086,072 A | 2/1992 | Trullas et al. | |
| 5,166,136 A | 11/1992 | Ward et al. | |
| 5,168,103 A | 12/1992 | Kinney et al. | |
| 5,350,769 A | 9/1994 | Kasai et al. | |
| 5,523,323 A | 6/1996 | Maccecchini | |
| 5,605,911 A | 2/1997 | Olney et al. | |
| 5,648,259 A | 7/1997 | Mallet et al. | |
| 5,741,778 A | 4/1998 | Martin et al. | |
| 5,763,393 A | 6/1998 | Moskal et al. | |
| 5,804,550 A | 9/1998 | Bourguignon | |
| 5,902,815 A | 5/1999 | Olney et al. | |
| 5,952,389 A | 9/1999 | Fogel | |
| 5,959,075 A | 9/1999 | Lok et al. | |
| 6,007,841 A | 12/1999 | Caruso | |
| 6,025,471 A | 2/2000 | Deghenghi | |
| 6,107,271 A | 8/2000 | Moskal et al. | |
| 6,147,230 A | 11/2000 | Shimamoto et al. | |
| 6,197,820 B1 | 3/2001 | Sontheimer et al. | |
| 6,521,414 B2 | 2/2003 | Melcher et al. | |
| 6,541,453 B2 | 4/2003 | Oldham et al. | |
| 6,635,270 B2 | 10/2003 | Hong et al. | |
| 6,667,317 B2 | 12/2003 | Chenard et al. | |
| 6,821,985 B2 | 11/2004 | Chenard et al. | |
| 6,828,318 B2 | 12/2004 | Snape et al. | |
| 7,273,889 B2 | 9/2007 | Mermelstein et al. | |
| 7,884,080 B2 | 2/2011 | Aslanian et al. | |
| 8,492,340 B2 | 7/2013 | Moskal | |
| 2002/0103335 A1 | 8/2002 | Oldham et al. | |
| 2003/0022253 A1 | 1/2003 | Moskal | |
| 2003/0064921 A1 | 4/2003 | Millhauser et al. | |
| 2003/0175734 A1 | 9/2003 | Kroes et al. | |
| 2005/0037433 A1 | 2/2005 | Nakanishi et al. | |
| 2005/0118286 A1 | 6/2005 | Suffin et al. | |
| 2006/0063707 A1 | 3/2006 | Baudry et al. | |
| 2006/0241046 A1 | 10/2006 | Olivera et al. | |
| 2007/0087404 A1 | 4/2007 | Stahl et al. | |
| 2007/0208001 A1 | 9/2007 | Zhuo et al. | |
| 2009/0221544 A1 | 9/2009 | Stein et al. | |
| 2010/0102616 A1 | 4/2010 | Yamasaki et al. | |
| 2011/0306586 A1 | 12/2011 | Khan et al. | |
| 2012/0295852 A1 | 11/2012 | Moskal | |
| 2013/0005662 A1 | 1/2013 | Moskal | |
| 2013/0035292 A1 | 2/2013 | Moskal et al. | |
| 2013/0053325 A1 | 2/2013 | Moskal et al. | |

(Continued)

FOREIGN PATENT DOCUMENTS

| | | |
|---|---|---|
| CN | 101066945 A | 11/2007 |
| CN | 101125817 A | 2/2008 |

(Continued)

OTHER PUBLICATIONS

Macias et al. Journal of Organic Chemistry 2006 (71) 7721-7730.*
Overman et al. Journal of the American Chemical Society 1985 (107) 1698-1701.*
Abbott AV et al., 'The Formalin Test: Scoring Properties of the First and Second Phases of the Pain Response in Rats,' Pain, Jan. 1995 (Jan. 1995), 60(1):91-102.
Abramets, II, 'Neurophysiological and Neurochemical Aspects of the Effects of Antidepressants and Mood Stabilizers,' Neurophysiol, Jan. 2008 (Jan. 2008), 40(1):64-78.
Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.
Anonymous, Database Accession No. 1031928-30-9, Database Registry [Online] Chemical Abstracts Service, Columbus, Ohio, US; Jul. 1, 2008 (Jul. 1, 2008), XP002668992.
Anonymous, Database Accession No. 1053605-89-2, Database Registry [Online] Chemical Abstracts Service, Columbus, Ohio, US; Sep. 28, 2008 (Sep. 28, 2008), XP002668993.

(Continued)

*Primary Examiner* — Jeffrey S Lundgren
*Assistant Examiner* — Michael Schmitt
(74) *Attorney, Agent, or Firm* — Goodwin Procter LLP

(57) ABSTRACT

Disclosed are compounds having enhanced potency in the modulation of NMD A receptor activity. Such compounds are contemplated for use in the treatment of conditions such as depression and related disorders. Orally available formulations and other pharmaceutically acceptable delivery forms of the compounds, including intravenous formulations, are also disclosed.

63 Claims, 1 Drawing Sheet

(56) References Cited

U.S. PATENT DOCUMENTS

| | | |
|---|---|---|
| 2013/0310323 A1 | 11/2013 | Moskal |
| 2013/0316954 A1 | 11/2013 | Moskal |
| 2014/0107037 A1 | 4/2014 | Moskal |
| 2015/0051262 A1 | 2/2015 | Khan et al. |
| 2015/0105364 A1 | 4/2015 | Khan et al. |
| 2015/0336969 A1 | 11/2015 | Khan et al. |
| 2015/0368252 A1 | 12/2015 | Lowe, III et al. |
| 2015/0368253 A1 | 12/2015 | Lowe, III et al. |
| 2015/0368254 A1 | 12/2015 | Lowe, III et al. |
| 2015/0376195 A1 | 12/2015 | Lowe, III et al. |

FOREIGN PATENT DOCUMENTS

| | | | |
|---|---|---|---|
| CN | 103974712 A | 8/2014 | |
| CN | 104321071 A | 1/2015 | |
| EP | 2542254 A1 | 1/2013 | |
| EP | 2771021 | 5/2013 | |
| JP | 2013519683 A | 5/2013 | |
| JP | 2014520072 A | 8/2014 | |
| RU | 2039035 C1 | 7/1995 | |
| WO | 9632105 A1 | 10/1996 | |
| WO | WO-97/43306 A1 | 11/1997 | |
| WO | WO-99/24584 A1 | 5/1999 | |
| WO | WO-99/51985 A1 | 10/1999 | |
| WO | WO-00/28090 A2 | 5/2000 | |
| WO | WO-01/36685 A2 | 5/2001 | |
| WO | WO-01/96606 A2 | 12/2001 | |
| WO | WO-01/98367 A2 | 12/2001 | |
| WO | WO-02/47535 A2 | 6/2002 | |
| WO | WO-02/072609 A2 | 9/2002 | |
| WO | WO-03/010540 A1 | 2/2003 | |
| WO | WO-2004-005293 A2 | 1/2004 | |
| WO | WO-2005/020973 A2 | 3/2005 | |
| WO | WO-2005-035535 A1 | 4/2005 | |
| WO | 2007103719 A2 | 9/2007 | |
| WO | WO-2009/039390 A2 | 3/2009 | |
| WO | WO-2009/105718 A1 | 8/2009 | |
| WO | WO-2010/015545 A1 | 2/2010 | |
| WO | WO-2010/033757 A1 | 3/2010 | |
| WO | WO-2010/065709 A2 | 6/2010 | |
| WO | WO-2010/102616 A1 | 9/2010 | |
| WO | WO-2011/003064 A2 | 1/2011 | |
| WO | WO-2011/044089 A2 | 4/2011 | |
| WO | WO-2011/100585 A1 | 8/2011 | |
| WO | WO 2011100585 A1 * | 8/2011 | ......... A61K 31/4025 |
| WO | WO-2012/149389 A2 | 11/2012 | |
| WO | WO-2013/001448 A1 | 1/2013 | |
| WO | WO-2013/063120 A2 | 5/2013 | |
| WO | WO-2014/011590 A2 | 1/2014 | |
| WO | WO-2014/120783 A1 | 8/2014 | |
| WO | WO-2014/120786 A1 | 8/2014 | |
| WO | WO-2014/120789 A1 | 8/2014 | |
| WO | WO-2014/120800 A1 | 8/2014 | |

OTHER PUBLICATIONS

Anonymous, NCBI Submission NM_000149, 'Homo sapiens Fucosyltransferase 3 (galactoside 3(4)-L-fucosyltransferase, Lewis Blood Group)(FUT3), Transcript Variant 1, mRNA,' 1990 (1990), Retrieved from the internet; <<URL:http://www.ncbi.nlm.nih.gov/nuccore/148277008>>, pp. 1-5.

Anonymous, NCBI Submission NM_001276, 'Homo sapiens Chitinase 3-like 1 (cartilage glycoprotein-39)(CHI3L1), mRNA,'1989 (1989), Retrieved from the internet; <URL:http://www.ncbi.nlm.nih.gov/nuccore/144226250>, pp. 1-5.

Anonymous, NCBI Submission NM_030979.1, 'Homo sapiens poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, 'Homo sapiens ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett Gj and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).

Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' ACNP 2010 Meeting, Dec. 6, 2010 (Dec. 6, 2010), pp. 1 (Poster #198).

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.

Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.

Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].

Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.

Coates C et al., 'Product Class 9: Beta-Lactams,' Science of Synthesis, Georg Thieme Verlag KG, Stuttgart, DE (Pub), 2000 (2000), 21:609-46.

Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.

Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.

Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.

Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.

Duman RS, 'Pathophysiology of Depression: The Concept of Synaptic Plasticity,' Eur Psychiatry, Jul. 2002 (Jul. 2002), 17(Suppl 3):306-10.

Erick M Carreira and Lisbet Kvaerno, Classics in Stereoselective Synthesis, (1st ed. 2009), Wiley-Vch Verlag GmbH & Co. KGaA, Weinham, DE (Publ), pp. 19-102 ISBN: 978-3-527-32452-1.

European Patent Office, Supplementary European Search Report (Form 1503) for EP 09 81 5233 (Fink D), completed at Munich DE dated Feb. 8, 2012 (Feb. 8, 2012) pp. 1-3.

(56) References Cited

OTHER PUBLICATIONS

European Patent Office, Supplementary European Search Report (Form 1503) for EP 10 82 2514 (Fink D), completed at Munich DE dated Feb. 1, 2013 (Feb. 1, 2013) pp. 1-2.
Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.
Foster AC and Fagg GE, 'Neurobiology: Taking Apart NMDA Receptors,' Nature, Oct. 1, 1987 (Oct. 1, 1987), 329(6138):395-6.
Golik U, 'Synthesis of Malonimide Derivatives as Potential Penicillin Analogs,' J Heterocycl Chem, Feb. 1972 (Feb. 1972), 9(1):21-4.
Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.
Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.
Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.
Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.
Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.
Holderbach R et al., 'Enhanced Long-Term Synaptic Depression in an Animal Model of Depression,' Biol Psychiatry, Dec. 4, 2006 (Dec. 4, 2006) (ePub), 62(1):92-100.
International Searching Authority, International Search Report (ISA/210) for Application No. PCT/US08/77045, (Young LW), dated Mar. 28, 2009 (Mar. 28, 2009) and dated Apr. 29, 2009 (Apr. 29, 2009), pp. 1-3.
International Searching Authority, International Search Report (ISA/210) for Application No. PCT/US09/57401, (Young LW), dated Dec. 6, 2009 (Dec. 6, 2009) and dated Dec. 24, 2009 (Dec. 24, 2009), pp. 1-2.
International Searching Authority, International Search Report (ISA/210) for Application No. PCT/US09/66536, (Kang YJ), dated Aug. 9, 2010 (Aug. 9, 2010) and dated Aug. 9, 2010 (Aug. 9, 2010), pp. 1-5.
International Searching Authority, International Search Report (ISA/210) for Application No. PCT/US2014/013619, (Wolf C), dated Mar. 6, 2014 (Mar. 6, 2014) and dated Mar. 20, 2014 (Mar. 20, 2014), pp. 1-3.
International Searching Authority, International Search Report (ISA/210) for Application No. PCT/US2014/013621, (Wolf C), dated Feb. 27, 2014 (Feb. 27, 2014) and dated Mar. 13, 2014 (Mar. 13, 2014), pp. 1-2.
International Searching Authority, International Search Report (ISA/210) for Application No. PCT/US2014/013623, (Wolf C), dated Mar. 3, 2014 (Mar. 3, 2014) and dated Mar. 13, 2014 (Mar. 13, 2014), pp. 1-3.
International Searching Authority, International Search Report (ISA/210) for Application No. PCT/US2014/013626, (Rudolf M), dated Mar. 10, 2014 (Mar. 10, 2014) and dated Mar. 18, 2014 (Mar. 18, 2014), pp. 1-4.
International Searching Authority, International Search Report (ISA/210) for Application No. PCT/US2014/013639, (Wolf C), dated Feb. 28, 2014 (Feb. 28, 2014) and dated Mar. 13, 2014 (Mar. 13, 2014), pp. 1-3.
International Searching Authority, Written Opinion of Application No. PCT/US2008/077045 (ISA/237), (Young LW), dated Mar. 28, 2009 (Mar. 28, 2009) and dated Mar. 24, 2010 (Mar. 24, 2010), pp. 1-8.
International Searching Authority, Written Opinion of Application No. PCT/US2009/057401 (ISA/237), (Young LW), dated Dec. 6, 2009 (Dec. 6, 2009) and dated Mar. 22, 2011 (Mar. 22, 2011), pp. 1-6.
International Searching Authority, Written Opinion of Application No. PCT/US2009/066536 (ISA/237), (Kang YJ), dated Aug. 9, 2010 (Aug. 9, 2010) and dated Jun. 7, 2011 (Jun. 7, 2011), pp. 1-8.
International Searching Authority, Written Opinion of Application No. PCT/US2014/013619 (ISA/237), (Wolf C), dated Mar. 6, 2014 (Mar. 6, 2014) and dated Aug. 4, 2015 (Aug. 4, 2015), pp. 1-4.
International Searching Authority, Written Opinion of Application No. PCT/US2014/013621 (ISA/237), (Wolf C), dated Feb. 27, 2014 (Feb. 27, 2014) and dated Aug. 4, 2015 (Aug. 4, 2015), pp. 1-6.
International Searching Authority, Written Opinion of Application No. PCT/US2014/013623 (ISA/237), (Wolf C), dated Mar. 3, 2014 (Mar. 6, 2014) and dated Aug. 4, 2015 (Aug. 4, 2015), pp. 1-4.
International Searching Authority, Written Opinion of Application No. PCT/US2014/013626 (ISA/237), (Rudolf M, dated Mar. 10, 2014 (Mar. 10, 2014) and dated Aug. 4, 2015 (Aug. 4, 2015), pp. 1-6.
International Searching Authority, Written Opinion of Application No. PCT/US2014/013639 (ISA/237), (Wolf C), dated Feb. 28, 2014 (Feb. 28, 2014) and dated Aug. 4, 2015 (Aug. 4, 2015), pp. 1-4.
Johnson JA et al., 'The Preparation of a Double Metallahelicate Containing 28 Copper Atoms,' Angew Chem Int Ed Engl, Feb. 3, 2003 (Feb. 3, 2003), 42(5):546-9.
Johnson KM and Jones SM, 'Neuropharmacolgy of Phencyclidine: Basic Mechanisms and Therapeutic Potential,' Annu Rev Pharmacol Toxicol, 1990 (1990), 30:707-50.
Khasanov AB et al., 'Novel Asymmetric Approach to Proline-Derived Spiro-beta-Lactams,' J Org Chem., Aug. 20, 2004 (Aug. 20, 2004), 69(17):5766-9.
Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.
Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.
Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.
Kroes RA et al., 'Development of a Novel Glycobiologic Therapy for Glioblastoma,' Neuro-oncol, Oct. 2006 (Oct. 2006), 8(4):397-8, (Abstract #CB-14).
Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).
Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.
Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).
Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.
Lynch G et al., 'Synaptic Pasticity in Early Aging,' Ageing Res Rev, Aug. 28, 2006 (Aug. 28, 2006) (ePub), 5(3):255-80.
Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.
Macias A et al., 'Unusual Rearrangement of Spiro-beta-Lactams to 1,4-diazabicyclo[4,4,0]decanes and 1,4-diazabicyclo[4,3,0] nonanes. Synthesis of Conformationally Restricted Sigma-Receptor Ligands,' Tetrahedron Lett, Jun. 2004 (Jun. 2004), 45(24):4657-60.

(56) References Cited

OTHER PUBLICATIONS

Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.

Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.

McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.

Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.

Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.

Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).

Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.

Moskal JR et al., 'A Novel Approach to Unlocking the Therapeutic Potential of the NMDA Receptor,' Vital Signs e-Magazine, Sep. 2010 (Sep. 2010), pp. 1-2.

Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.

Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.

Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).

Myers SM and Johnson CP, 'Management of Children with Autism Spectrum Disorders,' Pediatrics, Oct. 29, 2007 (Oct. 29, 2007) (ePub), 120(5):1162-82.

Narahashi T et al., 'Mechanisms of Action of Cognitive Enhancers on Neuroreceptors,' Biol Pharm Bull, Nov. 2004 (Nov. 2004), 27(11):1701-6.

Overman LE and Osawa T, 'A Convenient Synthesis of 4-Unsubstituted beta-Lactams,' J Am Chem Soc, Mar. 1985 (Mar. 1985), 107(6):1698-701.

Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.

Pittenger C et al., 'The NMDA Receptor as a Therapeutic Target in Major Depressive Disorder,' CNS Neurol Disord Targets, Apr. 2007 (Apr. 2007), 6(2):101-15.

Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.

Ransom RW and Stec NL, 'Cooperative Modulation of [3H]MK-801 Binding to the N-Methyl-d-Asparate Receptor-Ion Channel Complex by I-Glumate, Glycine, and Polyamines,' J Neurochem, Sep. 1988 (Sep. 1988), 51(3):830-6.

Rasmusson GH et al., '6-Substituted Penicillin Derivatives,' Tetrahedron Lett, 1973 (1973), 14(2):145-8.

Rautio J et al., 'Prodrugs: Design and Clinical Applications,' Nat Rev Drug Discov, Mar. 2008 (Mar. 2008), 7(3):255-70.

Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.

Shankar GM and Walsh DM, 'Alzheimer's Disease: Synaptic Dysfunction and A-beta,' Mol Neurodegener, Nov. 23, 2009 (Nov. 23, 2009), 4:48-61.

Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.

Simplício AL et a;., 'Prodrugs for Amines,' Molecules, Mar. 2008 (Mar. 2008), 13(3):519-47.

Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.

Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.

Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.

Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.

Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):6492-B501.

Various, *The NMDA Receptor*, (2nd ed. 1994), GL Collingridge and JC Watkins Eds., Oxford University Press, Inc., New York, New York US (Publ), pp. 1-479 ISBN: 0-19-262371-0.

Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.

Wood PL, 'The NMDA Receptor Complex: A Long and Winding Road to Therapeutics,' IDrugs, Mar. 2005 (Mar. 2005), 8(3):229-35.

Wood SG et al., 'Tetrapeptide Inhibitors of the IgA1 Proteinases from Type I Neisseria gonorrhoeae,' J Med Chem, Oct. 1989 (Oct. 1989), 32(10):2407-11.

Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.

U.S. Appl. No. 14/764,395, filed Jul. 29, 2015, Spiro-Lactam NMDA Modulators and Uses Thereof, Pending.

U.S. Appl. No. 14/932,579, filed Nov. 4, 2015, Spiro-Lactam NMDA Modulators and Uses Thereof, Pending.

U.S. Appl. No. 15/049,577, filed Feb. 22, 2016, Spiro-Lactam NMDA Modulators and Uses Thereof, Pending.

U.S. Appl. No. 14/764,411, filed Jul. 29, 2015, Spiro-Lactam NMDA Modulators and Uses Thereof, Published.

U.S. Appl. No. 14/764,419, filed Jul. 29, 2015, Spiro-Lactam NMDA Modulators and Uses Thereof, Published.

U.S. Appl. No. 14/764,426, filed Jul. 29, 2015, Spiro-Lactam NMDA Modulators and Uses Thereof, Published.

Singapore Search Report and Written Opinion issued for corresponding Singapore application No. 11201505860X, dated Apr. 18, 2016.

Singapore Search Report and Written Opinion issued for corresponding Singapore application No. 11201505942Y dated Mar. 22, 2016.

Singapore Search Report and Written Opinion issued for corresponding Singapore application No. 11201505934X, dated Apr. 27, 2016.

(56) References Cited

OTHER PUBLICATIONS

Singapore Search, Report and Written Opinion issued for corresponding Singapore application No. 11201505362T, dated Apr. 18, 2016.
Singapore Search Report and Written Opinion issued for corresponding Singapore application No. 11201505937S, dated May 5, 2016.

* cited by examiner

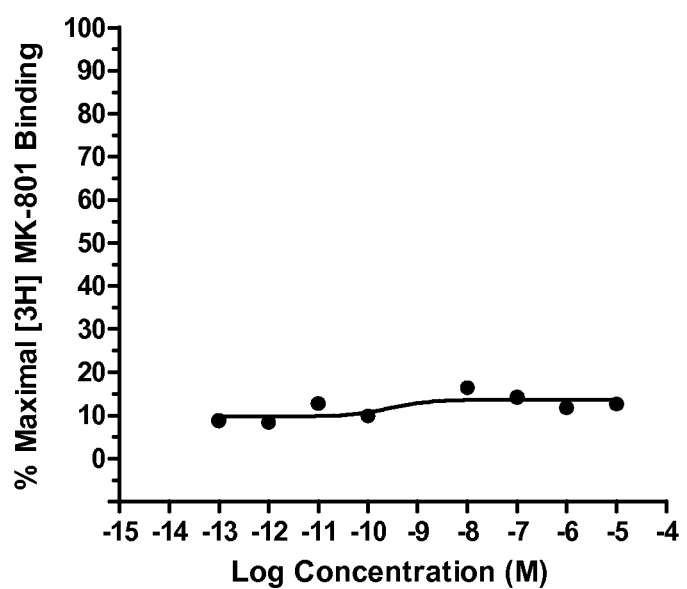

SPIRO-LACTAM NMDA RECEPTOR MODULATORS AND USES THEREOF

CROSS REFERENCE TO RELATED APPLICATIONS

This application is a United States National Stage of International Application No. PCT/US2014/013621, filed on Jan. 29, 2014, which claims the benefit of U.S. Provisional Application No. 61/757,920, filed on Jan. 29, 2013; the entire disclosure of each of these applications is incorporated by reference herein in its entirety.

BACKGROUND

An N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for orally deliverable forms of such compounds.

SUMMARY

Provided herein, at least in part, are compounds that are NMDA modulators, for example, partial agonists of NMDA. For example, disclosed herein are compounds represented by the formula:

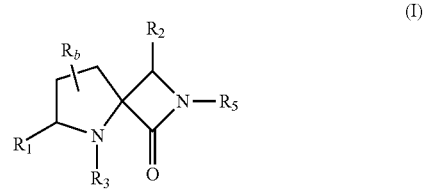

(I)

and pharmaceutically acceptable salts, stereoisomers, and N-oxides thereof, wherein $R_b$ is selected from the group consisting of H, halogen, hydroxyl, cyano or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

$R_5$ is X or —$C_1$-$C_6$ alkylene-X, wherein X is selected from the group consisting of phenyl, a 4- to 6-membered heteroaryl ring having 1, 2, or 3 heteroatoms selected from O, S, or N, or a 4- to 6-membered heterocyclyl ring having 1, 2, or 3 heteroatoms selected from O, S, or N, and wherein X is optionally substituted with

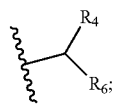

and $R_6$ is selected from the group consisting of H, halogen, hydroxyl, cyano, —O—C(O)—$C_1$-$C_6$ alkyl, $C_1$-$C_6$ alkyl, or $C_1$-$C_6$ alkoxy;

or, in other embodiments, the variables set forth in formula (I) are defined as follows:

$R_b$ is selected from the group consisting of H, halogen, hydroxyl, cyano or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

$R_5$ is X or —$C_1$-$C_6$ alkylene-X, wherein X is selected from the group consisting of:
(i) phenyl;
(ii) heteroaryl including from 5 to 6 ring atoms wherein 1, 2, or 3 of the ring atoms are independently selected from the group consisting of N, NH, N(C1-C3 alkyl), O, and S; and
(iii) heterocyclyl including from 3 to 6 ring atoms wherein 1, 2, or 3 of the ring atoms are independently selected from the group consisting of N, NH, N(C1-C3 alkyl), O, and S; wherein $R_5$ is optionally substituted with

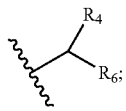

and $R_6$ is selected from the group consisting of H, halogen, hydroxyl, cyano, —O—C(O)—$C_1$-$C_6$ alkyl, $C_1$-$C_6$ alkyl, or $C_1$-$C_6$ alkoxy.

Also disclosed herein are compounds represented by the formula:

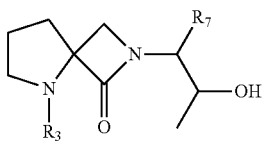

(II)

and pharmaceutically acceptable salts, stereoisomers, and N-oxides thereof, wherein $R_3$ is selected from the group consisting of H, $C_1$-$C_6$alkyl and a nitrogen protecting group; and $R_7$ is a 4- to 6-membered heteroaryl ring having 1, 2, or 3 heteroatoms selected from O, S, or N, optionally substituted on a free carbon by a substituent selected from the group consisting of:

halogen, $C_1$-$C_6$alkyl, hydroxyl, cyano, and phenyl.

Also provided herein are compounds represented by the formula:

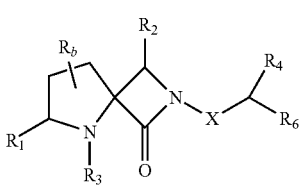

(III)

and pharmaceutically acceptable salts, stereoisomers, and N-oxides thereof, wherein $R_b$ is selected from the group consisting of H, halogen, hydroxyl, cyano or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

X is selected from the group consisting of phenyl, a 4- to 6-membered heteroaryl ring having 1, 2, or 3 heteroatoms selected from O, S, or N, or a 4- to 6-membered heterocyclyl ring having 1, 2, or 3 heteroatoms selected from O, S, or N, wherein

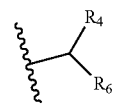

is present on a free carbon of X; and $R_6$ is selected from the group consisting of H, halogen, hydroxyl, cyano, —O—C(O)—$C_1$-$C_6$ alkyl, $C_1$-$C_6$ alkyl, or $C_1$-$C_6$ alkoxy.

Also provided herein are pharmaceutically acceptable compositions comprising a disclosed compound, and a pharmaceutically acceptable excipient. For example, such compositions may be suitable for oral or intravenous administration to a patient.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic, in a patient in need thereof is provided. Such methods may comprise administering to the patient a pharmaceutically effective amount of a disclosed compound or pharmaceutically acceptable salts, stereoisomers, N-oxides, and hydrates thereof.

In some embodiments, a contemplated method includes treating depression. For example, depression may include one or more of major depressive disorder, dysthymic disorder, psychotic depression, postpartum depression, seasonal affective disorder, bipolar disorder, mood disorder, or depression caused by a chronic medical condition. In other embodiments, a contemplated method may treat schizophrenia. Such schizophrenia may be, for example, paranoid type schizophrenia, disorganized type schizophrenia, catatonic type schizophrenia, undifferentiated type schizophrenia, residual type schizophrenia, post-schizophrenic depression, or simple schizophrenia.

BRIEF DESCRIPTION OF THE DRAWINGS

FIG. 1 shows the potentiation of [$^3$H]MK-801 binding in the presence of Compound Y.

DETAILED DESCRIPTION

This disclosure is generally directed to compounds that are capable of modulating NMDA, e.g., NMDA antagonists or partial agonists, and compositions and/or methods of using the disclosed compounds.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_2$-$C_6$alkenyl, and $C_3$-$C_4$ alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, alkoxys of 1-6 or 2-6 carbon atoms, referred to herein as $C_1$-$C_6$ alkoxy, and $C_2$-$C_6$ alkoxy, respectively. Exemplary alkoxy groups include, but are not limited to methoxy, ethoxy, isopropoxy, etc.

The term "alkenyloxy" used herein refers to a straight or branched alkenyl group attached to an oxygen (alkenyl-O). Exemplary alkenoxy groupd include, but are not limited to, groups with an alkenyl group of 3-6 carbon atoms, (also e.g. referred to as $C_3$-$C_6$ alkenyloxy). Exemplary "alkenoxy" groups include, but are not limited to allyloxy, butenyloxy, etc.

The term "alkynyloxy" used herein refers to a straight or branched alkynyl group attached to an oxygen (alkynyl-O)). Exemplary alkynyloxy groups include, but are not limited to, $C_3$-$C_6$ alkynyloxy, e.g., propynyloxy.

The term "alkyl" as used herein refers to a saturated straight or branched hydrocarbon, such as a straight or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc. The term "haloalkyl" as used herein refers to a saturated straight or branched alkyl groups, in which one or more hydrogen atoms of the alkyl group are replaced with one or more independently selected halogens. The term "haloalkyl" encompasses alkyl groups in which all of hydrogen atoms of the alkyl group are replaced independently selected halogens (sometimes referred to as "perhalo" alkyl groups. Exemplary haloalkyl groups include, but are not limited to, $CH_2F$, $CH_2CH_2Cl$, $CF_3$, $CHFCH_2Cl$.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$ alkynyl, and $C_3$-$C_6$ alkynyl, respectively. Exemplary alkynyl groups include, but are not limited to, ethynyl, propynyl, butynyl, pentynyl, hexynyl, methylpropynyl, etc.

The term "bridged cycloalkyl", as used herein, is defined as a monocyclic 4- to 7-membered cycloalkyl group in which two non-adjacent atoms are linked by a $CH_2$ or $CH_2CH_2$ group. A "bridged cycloalkyl" may be fused to one or more phenyl, partially unsaturated, or saturated rings. Examples of bridged carbocyclic groups include but are not limited to bicyclo[2.2.1]heptane, bicyclo[2.2.2]octane, bicyclo[2.2.2]octene etc.

The term "carbonyl" as used herein refers to the radical —C(O)—. The term "cyano" as used herein refers to the radical —CN. The term "nitro" refers to the radical —NO$_2$. The term "H" refers to hydrogen.

The term "cycloalkoxy" as used herein refers to a cycloalkyl group attached to an oxygen (cycloalkyl-O—).

The term "cycloalkyl" as used herein refers to a monocyclic saturated or partically unsaturated hydrocarbon group of for example 3-6, or 4-6 carbons, referred to herein, e.g., as "$C_{3-6}$ cycloalkyl" or "$C_{4-6}$ cycloalkyl," and derived from a cycloalkane. Exemplary cycloalkyl groups include, but are not limited to, cyclohexyl, cyclohexenyl, cyclopentyl, cyclobutyl, cyclopropyl or cyclopentyl.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furyl, thienyl, pyrrolyl, thiazolyl, oxazolyl, isothiazolyl, isoxazolyl, imidazolyl, pyrazolyl, triazolyl, oxadiazolyl (e.g., 1,2,4-oxadiazolyl or 1,3,4-oxadiazolyl), pyridyl, and pyrimidinyl.

The terms "heterocyclyl" or "heterocyclic group" are art-recognized and refer to saturated or partially unsaturated 4- to 7-membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited pyrrolidinyl, piperidinyl, morpholino, thiomorpholino, and piperazinyl.

The term "heterocyclylalkoxy" as used herein refers to a heterocyclyl-alkyl-O— group.

The term "heterocyclyloxyalkyl" refers to a heterocyclyl-O-alkyl-group.

The term "heterocycloxy" refers to a heterocyclyl-O— group. The term "cycloalkyloxy" refers to a cycloalkyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

The term "nitrogen protecting group" or "amino protecting group" is art-recognized and as used herein refers to a chemical moiety that is covalently linked to a nitrogen atom of an amino (primary or secondary) group and that temporarily blocks the reactivity of the amino group during a synthetic step and is selectively removed once the synthetic step is complete. Nitrogen protecting groups include, for example, 9-Fluorenylmethyloxycarbonyl (Fmoc), tert-butoxycarbonyl (Boc), carbobenzyloxycarbonyl (Cbz), p-methoxybenzyloxycarbonyl, acetyl, trifluoroacetyl, benzoyl, phthalimido, benzyl (Bn), p-methoxybenzyl, p-methoxyphenyl, 3,4-dimethoxybenzyl, triphenylmethyl, benzylidene, and p-toluenesulfonyl (Ts). In some embodiments, the nitrogen protecting group can have one of the following formulas: —C(O)OR$_{31}$ or —C(O)R$_{32}$ as defined herein. In certain embodiments, R$_{31}$ is selected from the group consisting of: C$_1$-C$_6$ alkyl; C$_1$-C$_6$ haloalkyl; C$_2$-C$_6$ alkenyl; C$_2$-C$_6$ alkynyl; C$_3$-C$_{10}$ cycloalkyl, wherein the C$_3$-C$_{10}$ cycloalkyl is optionally substituted with from 1-3 independently selected C$_1$-C$_3$ alkyl; —CH$_2$—C$_3$-C$_{10}$ cycloalkyl wherein the C$_3$-C$_{10}$ cycloalkyl is optionally substituted with from 1-3 independently selected C$_1$-C$_3$ alkyl; —CH$_2$-phenyl, wherein the phenyl is optionally substituted with from 1-2 substituents independently selected from C$_1$-C$_3$ alkyl, C$_1$-C$_3$ haloalkyl, C$_1$-C$_3$ alkoxy, C$_1$-C$_3$ haloalkoxy, nitro, halo, SO$_2$Me, cyano, and —OC(O)CH$_3$; and —CH$_2$-pyridyl. In certain embodiments, R$_{32}$ is selected from the group consisting of: H; C$_1$-C$_6$ alkyl; C$_1$-C$_6$ haloalkyl; phenyl, wherein the phenyl is optionally substituted with from 1-2 substituents independently selected from C$_1$-C$_3$ alkyl, C$_1$-C$_3$ haloalkyl, C$_1$-C$_3$ alkoxy, C$_1$-C$_3$ haloalkoxy, nitro, halo, SO$_2$Me, cyano, and —OC(O)CH$_3$; and pyridyl.

As used in the present disclosure, the term "partial NMDA receptor agonist" generally refers to a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment e.g., of pain or depression is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in lessening a symptom of depression.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, Classics in *Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$ $^{18}F$ and $^{36}Cl$, respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Compounds

Disclosed compounds include those represented by formula I:

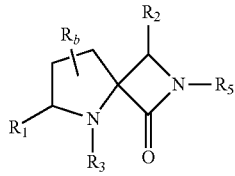

and pharmaceutically acceptable salts, stereoisomers, and N-oxides thereof, wherein $R_b$ is selected from the group consisting of H, halogen, hydroxyl, cyano or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

$R_5$ is X or —$C_1$-$C_6$ alkylene-X, wherein X is selected from the group consisting of phenyl, a 4- to 6-membered heteroaryl ring having 1, 2, or 3 heteroatoms selected from O, S, or N, or a 4- to 6-membered heterocyclyl ring having 1, 2, or 3 heteroatoms selected from O, S, or N, and wherein $R_5$ is optionally substituted with

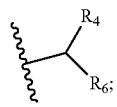

and $R_6$ is selected from the group consisting of H, halogen, hydroxyl, cyano, —O—C(O)—$C_1$-$C_6$ alkyl, $C_1$-$C_6$ alkyl, or $C_1$-$C_6$ alkoxy;

or, in other embodiments, the variables set forth in formula (I) are defined as follows:

$R_b$ is selected from the group consisting of H, halogen, hydroxyl, cyano or $C_1$-$C_6$ alkyl (e.g., H);

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

$R_5$ is X or —$C_1$-$C_6$ alkylene-X, wherein X is selected from the group consisting of:

(i) phenyl;

(ii) heteroaryl including from 5 to 6 ring atoms wherein 1, 2, or 3 of the ring atoms are independently selected from the group consisting of N, NH, N(C1-C3 alkyl), O, and S; and (iii) heterocyclyl including from 3 to 6 ring atoms wherein 1, 2, or 3 of the ring atoms are independently selected from the group consisting of N, NH, N(C1-C3 alkyl), O, and S; wherein $R_5$ is optionally substituted with

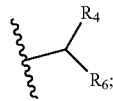

and $R_6$ is selected from the group consisting of H, halogen, hydroxyl, cyano, —O—C(O)—$C_1$-$C_6$ alkyl, $C_1$-$C_6$ alkyl, or $C_1$-$C_6$ alkoxy.

In certain embodiments, $R_1$ is H.

In certain embodiments, $R_2$ is H.

In certain embodiments, $R_3$ is H.

In other embodiments, $R_3$ is a nitrogen protecting group. In certain embodiments, $R_3$ has formula —C(O)O$R_{31}$, wherein $R_{31}$ is selected from the group consisting of: $C_1$-$C_6$ alkyl; $C_1$-$C_6$ haloalkyl; $C_2$-$C_6$ alkenyl; $C_2$-$C_6$ alkynyl; $C_3$-$C_{10}$ cycloalkyl, wherein the $C_3$-$C_{10}$ cycloalkyl is optionally substituted with from 1-3 independently selected $C_1$-$C_3$ alkyl; —CH$_2$—$C_3$-$C_{10}$ cycloalkyl wherein the $C_3$-$C_{10}$ cycloalkyl is optionally substituted with from 1-3 independently selected $C_1$-$C_3$ alkyl; —CH$_2$-phenyl, wherein the phenyl is optionally substituted with from 1-2 substituents independently selected from $C_1$-$C_3$ alkyl; $C_1$-$C_3$ haloalkyl; $C_1$-$C_3$ alkoxy; $C_1$-$C_3$ haloalkoxy; nitro; halo; SO$_2$Me, cyano; and —OC(O)CH$_3$; and —CH$_2$-pyridyl. In certain embodiments, $R_{31}$ is $C_1$-$C_6$ alkyl (e.g., ten-butyl). In other embodiments, $R_3$ has formula —C(O)$R_{32}$, wherein $R_{32}$ is selected from the group consisting of: H; $C_1$-$C_6$ alkyl; $C_1$-$C_6$ haloalkyl; phenyl, wherein the phenyl is optionally substituted with from 1-2 substituents independently selected from $C_1$-$C_3$ alkyl; $C_1$-$C_3$ haloalkyl; $C_1$-$C_3$ alkoxy; $C_1$-$C_3$ haloalkoxy; nitro; halo; SO$_2$Me, cyano; and —OC(O)CH$_3$; and pyridyl. In certain embodiments, $R_{32}$ is $C_1$-$C_6$ alkyl (e.g., —CH$_3$ or iso-propyl).

In certain embodiments, $R_4$ is $C_1$-$C_6$ alkyl. In some embodiments, $R_4$ is methyl.

In certain embodiments, $R_b$ is H.

In certain embodiments, $R_5$ is X, and wherein X is a 5- to 6-membered heteroaryl ring selected from the group consisting of azetidine, pyrrolidine, pyrazolidine, pyridine, pyrimidine, isooxazolidine, imidazolidine, oxazolidine, thiazolidine, and isothiazolidine. In other embodiments, $R_5$ is

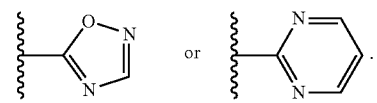

In certain other embodiments, $R_5$ is X, and wherein X is optionally substituted with

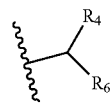

(sometimes referred to herein as "—CH($R_4$)($R_6$)").

In some embodiments, $R_5$ is X. In certain embodiments, X is heteroaryl including from 5 to 6 ring atoms wherein 1, 2, or 3 of the ring atoms are independently selected from the group consisting of N, NH, N($C_1$-$C_3$ alkyl), O, and S. For example, X can be selected from the group consisting of 1,2,4-oxadiazolyl, 1,3,4-oxadiazolyl, pyridyl, and pyrimidinyl. In certain embodiments, $R_5$ (here, X as defined anywhere herein) is substituted with —CH($R_4$)($R_6$). In certain embodiments, $R_4$ is $C_1$-$C_6$ alkyl (e.g., $R_4$ is methyl). In certain embodiments, $R_6$ is selected from the group consisting of hydroxyl, —O—C(O)—$C_1$-$C_6$ alkyl, and $C_1$-$C_6$ alkoxy (e.g., $R_6$ is hydroxyl). Embodiments in which $R_5$ is X can include one or more of the following features: $R_1$ is H or methyl; $R_2$ is H or methyl; $R_3$ is H, —C(O)O$R_{31}$, or —C(O)$R_{32}$; when present, $R_4$ is $C_1$-$C_6$ alkyl (e.g., $R_4$ is methyl), and $R_6$ is selected from the group consisting of hydroxyl, —O—C(O)—$C_1$-$C_6$ alkyl, and $C_1$-$C_6$ alkoxy (e.g., $R_6$ is hydroxyl); $R_b$ is H.

In some embodiments, $R_5$ is —$C_1$-$C_6$ alkylene-X (e.g., —$C_1$-$C_2$ alkylene-X or —$C_1$ alkylene-X). In certain embodiments, X is heteroaryl including from 5 to 6 ring atoms wherein 1, 2, or 3 of the ring atoms are independently selected from the group consisting of N, NH, N($C_1$-$C_3$ alkyl), O, and S. For example, X can be selected from the group consisting of 1,2,4-oxadiazolyl, 1,3,4-oxadiazolyl, pyridyl, and pyrimidinyl. In certain embodiments, $R_5$ is substituted on either the X portion or the alkylene chain portion with —CH($R_4$)($R_6$). In certain of these embodiments, $R_5$ is substituted on the alkylene portion with —CH($R_4$)($R_6$), and $R_5$ can have, for example, the formula —CH(CH$R_4R_6$)—X. In certain embodiments, $R_4$ is $C_1$-$C_6$ alkyl (e.g., $R_4$ is methyl). In certain embodiments, $R_6$ is selected from the group consisting of hydroxyl, —O—C(O)—$C_1$-$C_6$ alkyl, and $C_1$-$C_6$ alkoxy (e.g., $R_6$ is hydroxyl). Embodiments in which $R_5$ is —$C_1$-$C_6$ alkylene-X can include one or more of the following features: $R_1$ is H or methyl; $R_2$ is H or methyl; $R_3$ is H, —C(O)O$R_{31}$, or —C(O)$R_{32}$; when present, $R_4$ is $C_1$-$C_6$ alkyl (e.g., $R_4$ is methyl), and $R_6$ is selected from the group consisting of hydroxyl, —O—C(O)—$C_1$-$C_6$ alkyl, and $C_1$-$C_6$ alkoxy (e.g., $R_6$ is hydroxyl); $R_b$ is H.

In certain embodiments, $R_6$ is hydroxyl.

In some embodiments, a disclosed compound includes those delineated in Table 1 and/or the Examples, e.g., one having the formula:

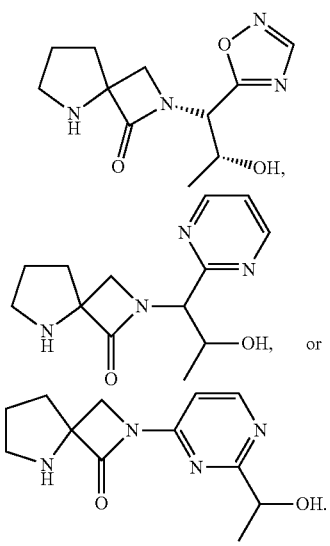

Disclosed compounds also include compounds represented by formula II:

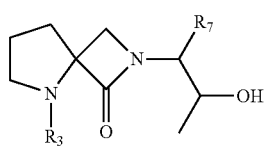

(II)

and pharmaceutically acceptable salts, stereoisomers, and N-oxides thereof, wherein $R_3$ is selected from the group consisting of H, $C_1$-$C_6$alkyl and a nitrogen protecting group; and $R_7$ is a 4- to 6-membered heteroaryl ring having 1, 2, or 3 heteroatoms selected from O, S, or N, optionally substituted on a free carbon by a substituent selected from the group consisting of: halogen, $C_1$-$C_6$alkyl, hydroxyl, cyano, and phenyl.

Also disclosed are compounds represented by formula III:

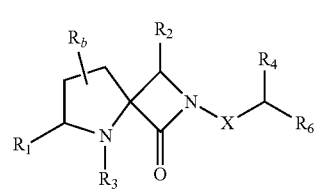

(III)

and pharmaceutically acceptable salts, stereoisomers, and N-oxides thereof, wherein $R_b$ is selected from the group consisting of H, halogen, hydroxyl, cyano or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

X is selected from the group consisting of phenyl, a 4- to 6-membered heteroaryl ring having 1, 2, or 3 heteroatoms selected from O, S, or N, or a 4- to 6-membered heterocyclyl ring having 1, 2, or 3 heteroatoms selected from O, S, or N, wherein

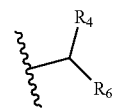

is present on a free carbon of X; and $R_6$ is selected from the group consisting of H, halogen, hydroxyl, cyano, —O—C(O)—$C_1$-$C_6$ alkyl, $C_1$-$C_6$ alkyl, or $C_1$-$C_6$ alkoxy.

In certain embodiments, $R_1$ is H.
In certain embodiments, $R_2$ is H.
In some embodiments, $R_3$ is H.
In certain embodiments, $R_4$ is $C_1$-$C_6$ alkyl. In other embodiments, $R_4$ is methyl.
In some embodiments, $R_b$ is H.
In certain embodiments, X is

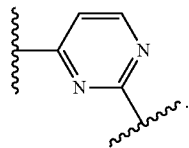 [SMILES: *c1ccnc(*)n1]

In some embodiments, $R_6$ is hydroxyl.

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50, between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds. In some instances, chemical formulas contain the descriptor "—(R)—" or "—(S)—" that is further attached to solid wedge or dashed wedge. This descriptor is intended to show a methine carbon (CH) that is attached to three other substituents and has either the indicated R or S configuration (see, e.g., Table 1).

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50})$:$(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound may be formulated with one or more additional compounds that enhance the solubility of the compound.

Methods

Methods for treating a condition in a patient in need thereof by administering a therapeutically effective dose of a compound described herein are provided. In some embodiments, the condition may be a mental condition. For example, a mental illness may be treated. In another aspect, a nervous system condition may be treated. For example, a condition that affects the central nervous system, the peripheral nervous system, and/or the eye may be treated. In some embodiments, neurodegenerative diseases may be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, migraine, AIDS dementia, Huntington's chorea, Parkinson's disease, early stage Alzheimer's disease, and Alzheimer's disease are contemplated.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions contemplated herein. Psychotic disorders such as schizoaffective disorders, delusional disorders, brief psychotic disorders, shared psychotic disorders, and psychotic disorders with delusions or hallucinations may also be treated using the compositions contemplated herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only.

Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In another embodiment, methods for treating delusions (e.g., "non-bizarre") that may be present in, for example, delusional disorder are provided.

Also provided are methods for treating social withdrawal in conditions including, but not limited to, social anxiety disorder, avoidant personality disorder, and schizotypal personality disorder.

In some embodiments, methods are provided for treating neuropathic pain. The neuropathic pain may be acute or chronic. In some cases, the neuropathic pain may be associated with a condition such as herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain. Methods for enhancing pain relief and for providing analgesia to a patient are also contemplated.

Further contemplated methods include a method of treating autism and/or an autism spectrum disorder in a patient need thereof, comprising administering an effective amount of a compound to the patient. In an embodiment, a method for reducing the symptoms of autism in a patient in need thereof is contemplated, comprising administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRAS, GFAP, GRIN2A, PDYN, and PENK. In another embodiment, a method of modulating synaptic plasticity in a patient suffering from a synaptic plasticity related disorder is provided, comprising administering to the patient an effective amount of a compound.

In another embodiment, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound may provide neuroprotective properties to a Alzheimer's patient in need thereof, for example, may provide a therapeutic effect on later stage Alzheimer's—associated neuronal cell death.

In a further embodiment, a method of treating depression comprising administering a compound described herein is provided. In some embodiments, the treatment may relieve depression or a symptom of depression without affecting behavior or motor coordination and without inducing or promoting seizure activity. Exemplary depression conditions that are expected to be treated according to this aspect of the invention include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering from a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound may be administered to a patient to treat a particular episode (e.g., a severe episode) of a condition contemplated herein.

Also contemplated herein are combination therapies comprising a compound in combination with one or more other active agents. For example, a compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only, and are not intended to limit the scope of the disclosure.

Table 1 below shows some exemplary compounds of the disclosure and provides physiochemical characteristics of the compounds.

TABLE 1

| Compound | Structure | Molecular Weight (Da) | cLogP | tPSA |
|---|---|---|---|---|
| Compound X | 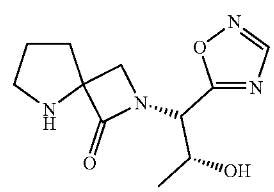 | 252 | −1.14 | 91.5 |
| Compound Y | 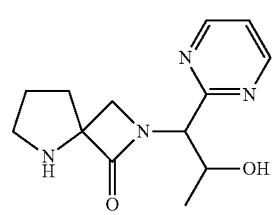 [SMILES: CC(O)C(c1ncccn1)N1CC2(CCCN2)C1=O] | 262 | −0.57 | 78.35 |
| Compound Z | 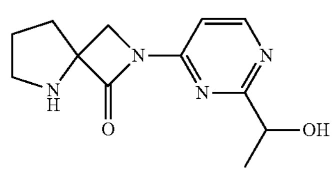 [SMILES: CC(O)c1nccc(N2CC3(CCCN3)C2=O)n1] | 248 | −0.15 | 78.35 |

TABLE 1-continued

| Compound | Structure | Molecular Weight (Da) | cLogP | tPSA |
|---|---|---|---|---|
| C-16 | 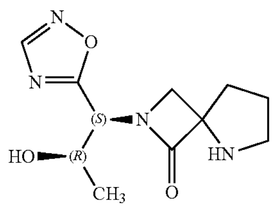 | 252.2697 | −1.1382 | 91.49 |
| C-4 | 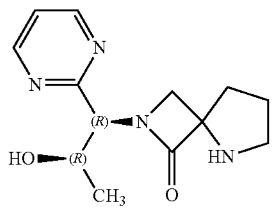 | 262.3076 | −0.57075 | 78.35 |
| C-15 | 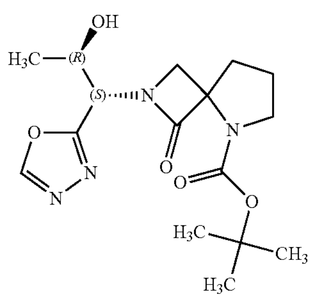 | 352.3856 | 0.144989 | 109 |
| C-20 | 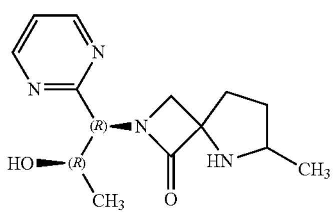 | 276.3342 | −0.160256 | 78.35 |
| C-36 | 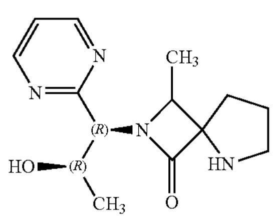 | 276.3342 | −0.160256 | 78.35 |
| C-33 | 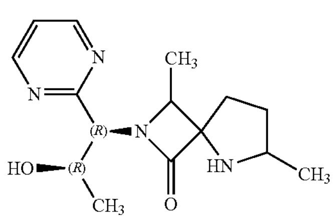 | 290.3608 | 0.250239 | 78.35 |

TABLE 1-continued

| Compound | Structure | Molecular Weight (Da) | cLogP | tPSA |
|---|---|---|---|---|
| C-10 | 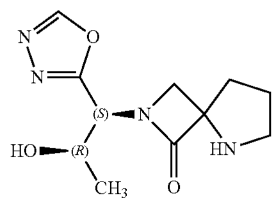 | 252.2697 | −1.83479 | 91.49 |
| C-9 | 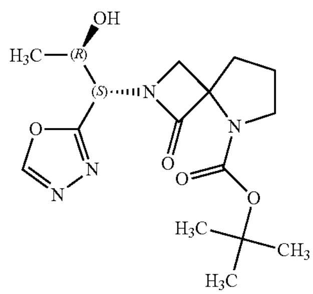 | 352.3856 | −0.551597 | 109 |
| C-3 | 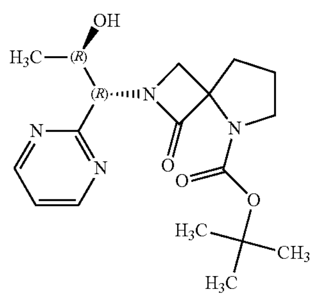 | 362.4234 | 0.672806 | 95.86 |
| C-23 | 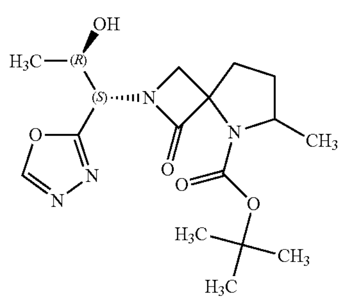 | 366.4121 | −0.135022 | 109 |
| C-19 | 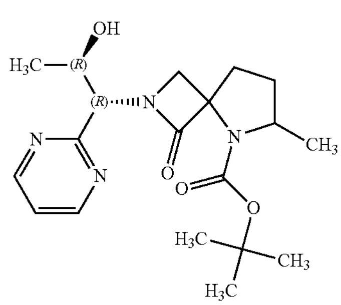 | 376.45 | 1.0833 | 95.86 |

TABLE 1-continued

| Compound | Structure | Molecular Weight (Da) | cLogP | tPSA |
|---|---|---|---|---|
| C-26 | 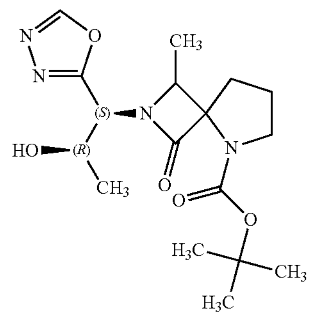 | 366.4121 | −0.135022 | 109 |
| C-29 | 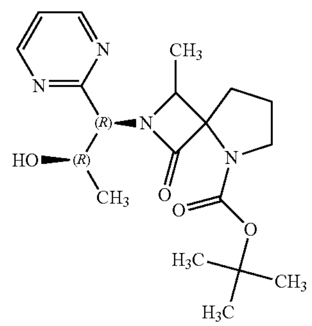 | 376.45 | 1.0833 | 95.86 |
| C-32 | 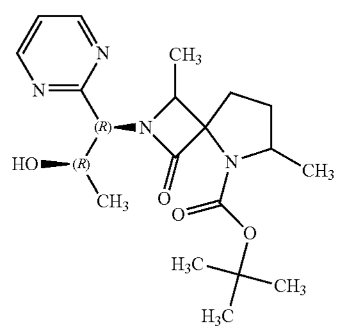 | 390.4766 | 1.4938 | 95.86 |
| C-11 | 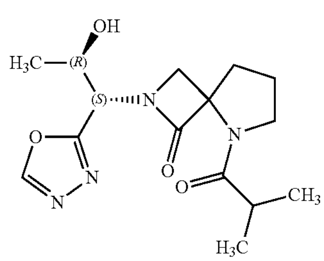 | 322.3596 | −0.981326 | 99.77 |
| C-5 | 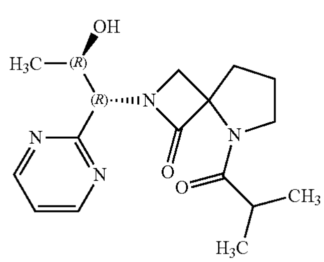 | 332.3975 | 0.335914 | 86.63 |

TABLE 1-continued
| Compound | Structure | Molecular Weight (Da) | cLogP | tPSA |
|---|---|---|---|---|
| C-37 | 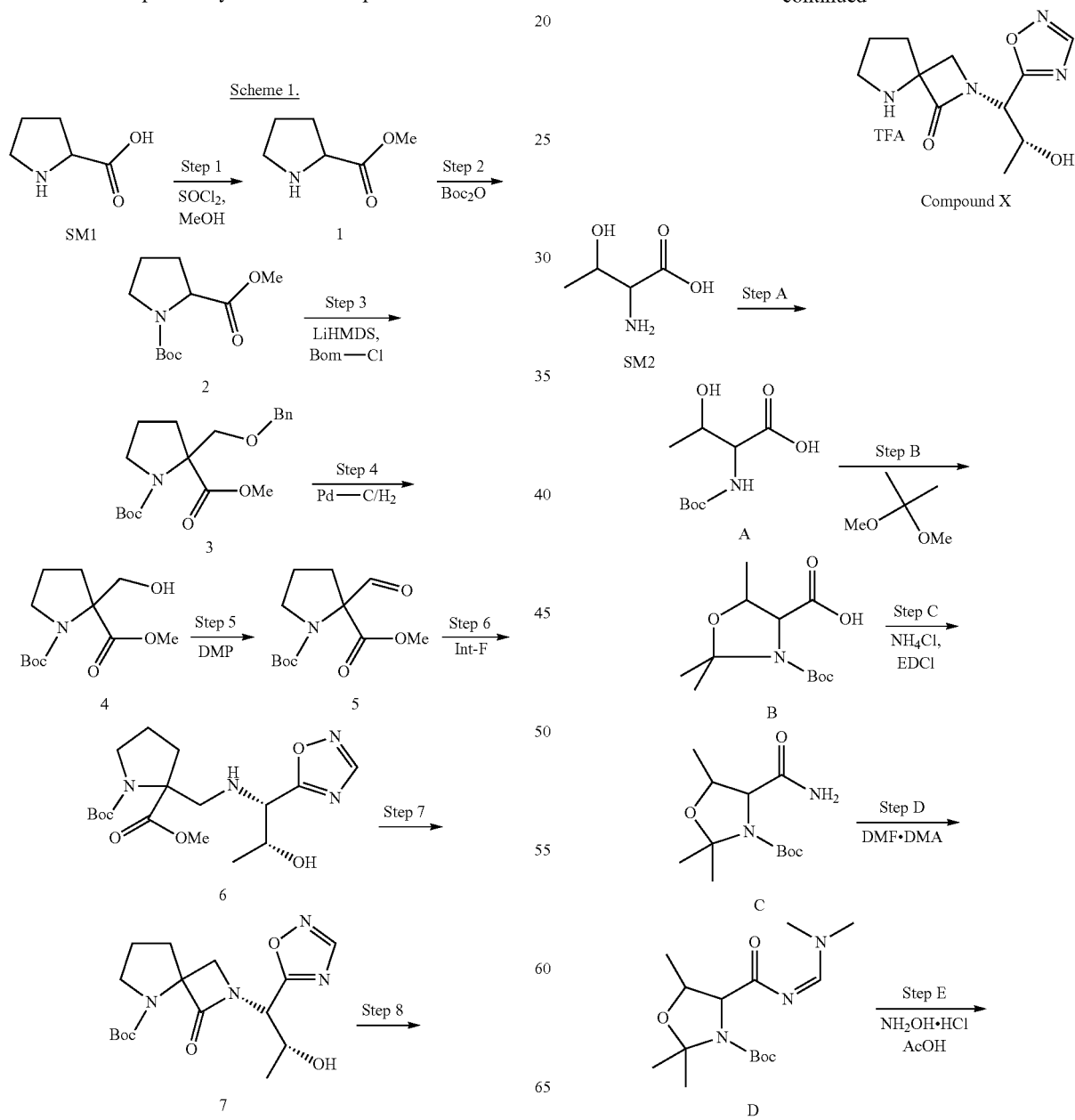 | 346.424 | 0.746408 | 86.63 |
Example 1—Synthesis of Compound X

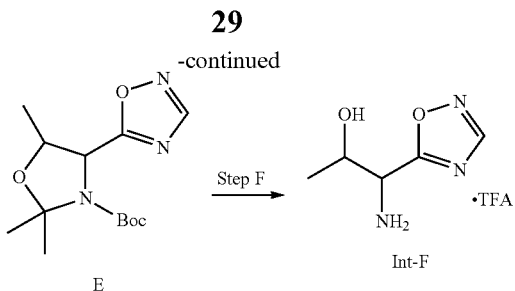

Synthesis of 2-((tert-butoxycarbonyl)amino)-3-hydroxybutanoic acid (A)

To a stirring solution of 2-amino-3-hydroxybutanoic acid (SM2) (10 g, 83.9 mmol) in 1,4-dioxane/water (100 mL, 1:1)) was added NaHCO$_3$ (21.1 g, 0.25 mol) followed by Boc-anhydride (21.9 mL, 0.101 mol) at 0° C. The reaction mixture was stirred at RT for 16 h. After consumption of the starting material (by TLC), the reaction mixture was diluted with water and washed with EtOAc. The aqueous layer was acidified using citric acid solution (pH ~3-4) and then extracted with CH$_2$Cl$_2$ (2×150 mL). The separated organic extracts were dried over anhydrous Na$_2$SO$_4$, filtered and concentrated under vacuum to afford A (15 g, crude). This material was directly used for the next step without further purification.

Synthesis of 3-(tert-butoxycarbonyl)-2,2,5-trimethyloxazolidine-4-carboxylic acid (B)

To a stirring solution of A (15 g, 59.28 mmol) in THF (150 mL) was added PPTS (1.47 g, 5.92 mmol) followed by 2,2-dimethoxy propane (21.79 mL, 0.17 mol) at 0° C. under N$_2$ atmosphere. The reaction mixture was stirred at RT for 16 h. The reaction mixture was again heated to reflux for 6 h. The reaction mixture was diluted with aqueous NaHCO$_3$ solution and washed with EtOAc. The aqueous layer was acidified using citric acid solution (pH ~2) and extracted with CH$_2$Cl$_2$ (2×100 mL). The organic layer was washed with brine, dried over anhydrous Na$_2$SO$_4$ and concentrated under vacuum to afford B (18 g, crude).

$^1$H-NMR: (400 MHz, DMSO-d$_6$): δ 13.25 (br s, 1H), 4.11-4.05 (m, 1H), 3.79 (d, 1H), 1.50 (s, 3H), 1.67 (s, 3H), 1.45 (s, 9H), 1.29 (d, 3H).

Synthesis of tert-butyl 4-carbamoyl-2,2,5-trimethyloxazolidine-3-carboxylate (C)

To a stirring solution of B (18 g, 69.4 mmol) in CH$_2$Cl$_2$ (180 mL) was added HOBt (14.16 g, 0.104 mol), EDCI.HCl (19.88 g, 0.104 mol) followed by NH$_4$Cl (5.56 g, 0.104 mol) and DIPEA (31.9 mL, 0.173 mol) at 0° C. The reaction mixture was stirred at RT for 16 h. After consumption of the starting material (by TLC), the reaction mixture was washed with aqueous citric acid, NaHCO$_3$ followed by brine. The organic layer was dried over anhydrous Na$_2$SO$_4$ and concentrated under reduced pressure. The resulting crude material was purified by silica gel column chromatography eluting with 2% MeOH/CH$_2$Cl$_2$ to afford C (13 g, 72.5%).

$^1$H-NMR: (400 MHz, DMSO-d$_6$): δ 7.51 (br s, 1H), 7.14 (br s, 1H), 3.97-3.95 (m, 1H), 3.71 (d, 1H), 1.51 (s, 6H), 1.34 (s, 9H), 1.24 (d, 3H).

LCMS (ESI): 159.1 [(M$^+$+1)-Boc]

Synthesis of (Z)-tert-butyl 4-(((dimethylamino)methylene)carbamoyl)-2,2,5-trimethyloxazolidine-3-carboxylate (D)

A solution of C (13 g, 50.3 mmol) in DMF.DMA (130 mL) was stirred at reflux temperature for 3 h under N$_2$ atmosphere. After consumption of the starting material (by TLC), the reaction mixture was concentrated under reduced pressure to afford D (15.7 g, crude). This crude material was directly taken for the next step without further purification.

Synthesis of tert-butyl 2,2,5-trimethyl-4-(1,2,4-oxadiazol-5-yl)oxazolidine-3-carboxylate (E)

To a stirring solution of D (15.7 g, 50.09 mmol) in ethanol (157 mL) was added hydroxylamine hydrochloride (6.96 g, 0.10 mol) under N$_2$ atmosphere. The reaction mixture was heated to reflux and stirred for 2 h. After consumption of the starting material (by TLC), acetic acid (28.6 mL, 0.50 mol) was added to the reaction mixture and then refluxed for 16 h. Solvents from the reaction mixture were evaporated under vacuum. The resulting crude material was purified by silica gel column chromatography eluting with 10% EtOAc/Hexane to afford E (4.5 g, 32%).

$^1$H-NMR: (400 MHz, DMSO-d$_6$): δ 6.35 (s, 2H), 4.61 (d, 1H), 4.22-4.15 (m, 1H), 1.55 (s, 6H), 1.37 (s, 2H), 1.25 (d, 3H), 1.21 (s, 6H).

LCMS (ESI): 284 [M$^+$+1]

Mass (m/z): 283 [M$^+$]

Synthesis of 1-amino-1-(1,2,4-oxadiazol-5-yl)propan-2-ol (Int-F)

To a stirring solution of E (5 g, 17.6 mmol) in water (25 mL) was added trifluoroacetic acid (25 mL). The reaction mixture was stirred at RT for 5 h. After consumption of the starting material (by TLC), the reaction mixture was concentrated under vacuum. The residue was dissolved in water and neutralized with aqueous NaHCO$_3$. The solvents from the reaction mixture were evaporated under vacuum and extracted with 5% MeOH/CH$_2$Cl$_2$ (4×150 mL). The organic layer was concentrated under reduced pressure to afford Int-F (2.5 g, crude).

$^1$H-NMR: (400 MHz, D$_2$O): δ 8.84 (s, 1H), 4.05 (d, 1H), 3.98-3.95 (m, 1H), 3.67 (s, 1H), 3.58 (d, 1H), 1.15 (d, 3H), 1.12 (d, 3H).

LCMS (ESI): 144.1 [M$^+$+1]

Synthesis of methyl pyrrolidine-2-carboxylate (1)

To a stirring solution of pyrrolidine-2-carboxylic acid (SM1) (100 g, 0.87 mol) in methanol (800 mL) was added thionyl chloride (76.9 mL, 1.04 mol) slowly drop wise at 0° C. The reaction mixture was heated to reflux for 12 h. After consumption of the starting material (by TLC), the reaction was concentrated under vacuum. Obtained residue was washed with n-Hexane and distilled off the solvent to afford 1 (143.9 g, HCl salt).

$^1$H-NMR: (400 MHz, CDCl$_3$) (Rotamers): δ 3.89 (s, 3H), 3.68-3.62 (m, 2H), 3.59-3.47 (m, 2H), 2.49-2.37 (m, 1H), 2.27-2.05 (m, 3H).

LCMS (ESI): 166 [M$^+$+1]

Synthesis of 1-tert-butyl 2-methyl pyrrolidine-1,2-dicarboxylate (2)

To a stirring solution of 1 (35 g, 0.22 mol) in CH$_2$Cl$_2$ (175 mL) were added Et$_3$N (90 mL, 0.65 mol) followed by Boc-anhydride (56.9 mL, 0.26 mol) at 0° C. The reaction mixture was stirred at RT for 16 h. After consumption of the starting material (by TLC), the reaction was diluted with water (100 mL) and extracted with $CH_2Cl_2$ (2×100 mL). The organic layer was washed with water, brine, dried over $Na_2SO_4$ and concentrated. Obtained crude material was purified by silica gel column chromatography eluting with 30% EtOAc/Hexane to afford 2 (41 g, 95%).

$^1$H-NMR: (400 MHz, $CDCl_3$) (Rotamers): δ 4.25-4.21 (m, 1H), 3.75 (s, 3H), 3.57-3.26 (m, 2H), 2.29-2.10 (m, 1H), 1.99-1.75 (m, 3H), 1.45 (s, 9H).

LCMS (ESI): 130 [($M^+$+1)-Boc]

Synthesis of 1-tert-butyl 2-methyl 2-((benzyloxy)methyl)pyrrolidine-1,2-dicarboxylate To a stirring solution of 2 (100 g, 0.43 mol) in THF (800 mL) was added LiHMDS (873 mL, 0.87 mol) at −78° C. and stirred for 1 h. To this BOM-chloride (93.2 mL, 0.65 mol) was added drop wise at −78° C. and stirred for 2 h at −20° C. After consumption of the starting material (by TLC), the reaction was quenched with $NH_4Cl$ at 0° C. The separated organic layer was washed with water, dried over $Na_2SO_4$ and concentrated to afford 3 (180 g, crude). This material was directly taken for the next step without further purification.

LCMS (ESI): 250 [($M^+$+1)-Boc]

Synthesis of 1-tert-butyl 2-methyl 2-(hydroxymethyl)pyrrolidine-1,2-dicarboxylate (4)

To a stirring solution of 3 (74 g, 0.21 mol) in methanol (740 mL) was added 10% Pd/C (50% wet, 14.8 g) under $N_2$ atmosphere and stirred for 6 h under $H_2$ atmosphere (balloon pressure). The reaction mixture was filtered through celite pad and concentrated under reduced pressure to afford 4 (45 g, 82%) as crude.

Synthesis of 1-tert-butyl 2-methyl 2-formylpyrrolidine-1,2-dicarboxylate (5)

To a stirring solution of 4 (10 g, 38.5 mmol) in $CH_2Cl_2$ (100 mL) was added Dess-martin periodinane (19.6 g, 46.27 mmol) at 0° C. under $N_2$ atmosphere and stirred for 3 h. After consumption of the starting material (determined by TLC), the reaction was quenched with aqueous $NaHCO_3$ solution and extracted with $CH_2Cl_2$ (2×100 mL). The organic layer was dried over anhydrous $Na_2SO_4$ and concentrated under vacuum. The resulting crude material was purified by column chromatography eluting with 10% EtOAc/Hexane to afford 5 (7 g, 70.5%).

Synthesis of 1-tert-butyl 2-methyl 2-(4(1S, 2R)-2-hydroxy-1-(1,2,4-oxadiazol-5-yl)propyl)amino) methyl)pyrrolidine-1, 2-dicarboxylate (6)

To a stirring solution of 5 (3 g, 11.6 mmol) in MeOH (30 mL) was added sodium acetate (1.91 g, 23.3 mmol) followed by Int-F (3.6 g, 13.9 mmol). The reaction mixture was heated to reflux for 1 h. The reaction mixture was slowly cooled to RT-0° C., to this sodium cyanoborohydride (1.465 g, 23.3 mmol) was added, and stirring was continued for another 6 h at RT. After consumption of the starting material (determined by TCL), methanol from the reaction was evaporated under reduced pressure and the residue was diluted with water and extracted with EtOAc (2×50 mL). The separated organic layer was dried over anhydrous $Na_2SO_4$ and concentrated under reduced pressure. The resulting crude material was purified by silica gel column chromatography eluting with 40% EtOAc/Hexane to afford 6 (2.5 g, 56%).

LCMS m/z: 385 [$M^l$+1]

Synthesis of tert-butyl 2-((1S, 2R)-2-hydroxy-1-(1, 2,4-oxadiazol-5-yl)propyl)-1-oxo-2,5-diazaspiro[3.4] octane-5-carboxylate (7)

To a stirring solution of 6 (1.5 g, 3.90 mmol) in THF (30 mL) was cooled to 0° C. and added t-BuMgCl (1M in THF, 15.6 mL, 15.6 mmol) and stirred for 15 min. After consumption of the starting material (by TLC), the reaction mixture was quenched with aqueous $NH_4Cl$ solution and diluted with water. Aqueous layer was extracted with EtOAc (2×25 mL). The separated organic layer was dried over anhydrous $Na_2SO_4$ and concentrated under reduced pressure. The resulting crude material was purified by silica gel column chromatography eluting with 150% EtOAc/$CH_2Cl_2$ to afford 7 (0.15 g, 11%).

$^1$H-NMR: (400 MHz, DMSO-d6): δ 9.02 (s, 1H), 5.15 (s, 1H), 4.37-4.32 (m, 1H), 3.95 (d, 1H), 3.66-3.60 (m, 1H), 3.36-3.30 (m, 1H), 2.29-2.09 (m, 2H), 1.87-1.82 (m, 2H), 1.55 (s, 9H), 1.27 (d, 3H).

LCMS (ESI) m/z: 351 [$M^+$−1]

UPLC Purity: 96%

Synthesis of 2-((1S, 2R)-2-hydroxy-1-(1,2,4-oxadiazol-5-yl)propyl)-2,5-diazaspiro[3.4]octan-1-one (Compound X)

To a stirring solution of 7 (0.4 g, 1.13 mmol) in $CH_2Cl_2$ (4 mL) was added TFA (0.43 mL) at 0° C. and stirred at RT for 30 min. The reaction mixture was concentrated under vacuum. The resulting crude material was purified by prep-HPLC to afford Compound X (65 mg) as TFA salt.

$^1$H-NMR: (400 MHz, DMSO-d6): δ 9.89 (br s, 1H), 9.08 (s, 1H), 5.46 (d, 1H), 5.31 (s, 1H), 4.37-4.35 (m, 1H), 3.99 (d, 1H), 3.81 (d, 1H), 3.42-3.35 (m, 2H), 2.35-2.18 (m, 2H), 2.10-2.03 (m, 2H), 1.24 (d, 3H).

LCMS (ESI) m/z: 253.4 [$M^+$+1]

Prep-HPLC Purity: 95%

Example 2—Synthesis of Compound Y

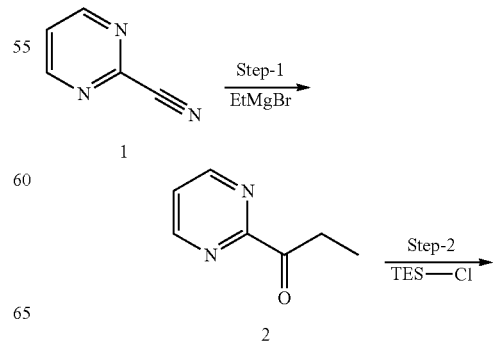

Scheme 2.

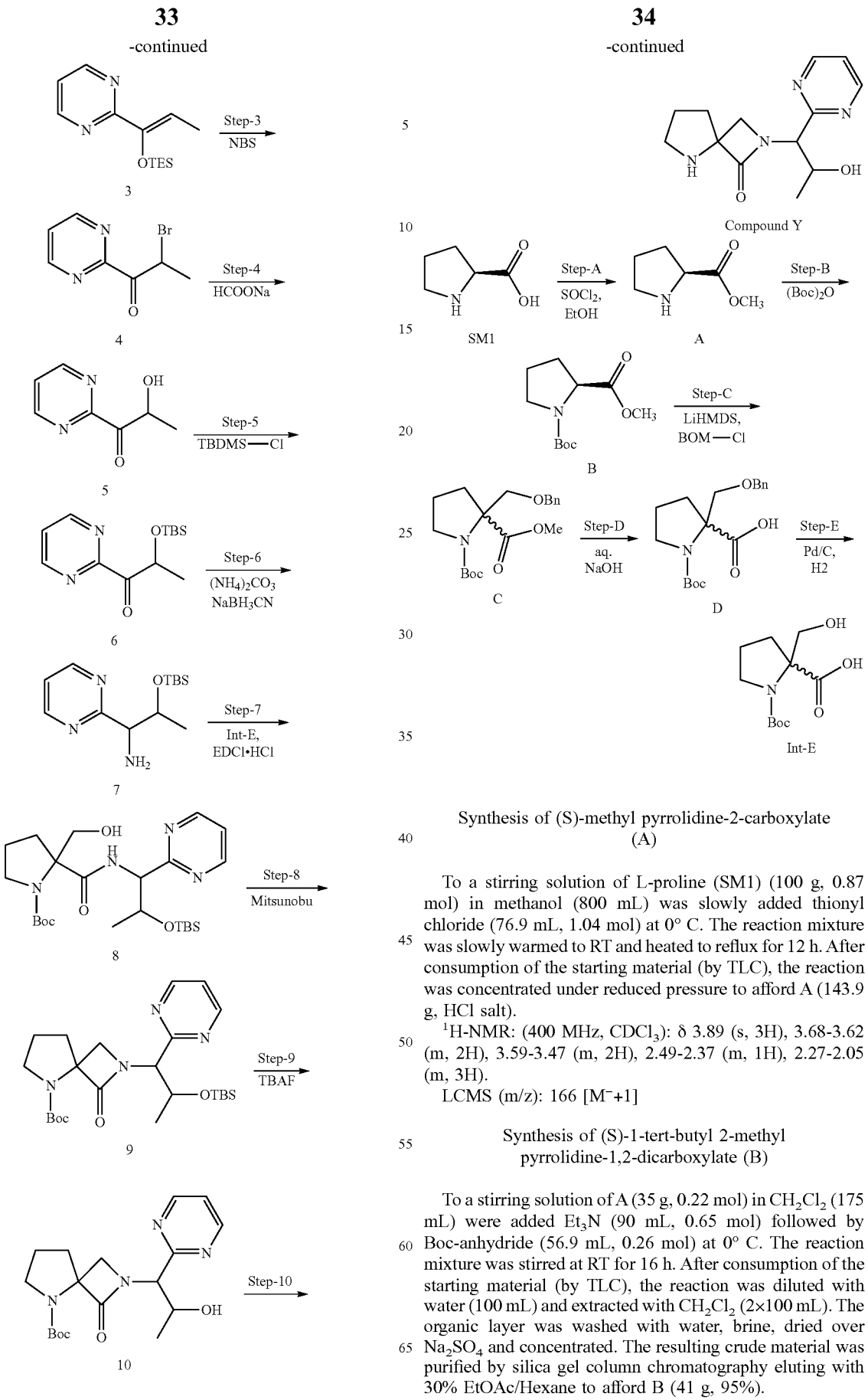

Synthesis of (S)-methyl pyrrolidine-2-carboxylate (A)

To a stirring solution of L-proline (SM1) (100 g, 0.87 mol) in methanol (800 mL) was slowly added thionyl chloride (76.9 mL, 1.04 mol) at 0° C. The reaction mixture was slowly warmed to RT and heated to reflux for 12 h. After consumption of the starting material (by TLC), the reaction was concentrated under reduced pressure to afford A (143.9 g, HCl salt).

$^1$H-NMR: (400 MHz, CDCl$_3$): δ 3.89 (s, 3H), 3.68-3.62 (m, 2H), 3.59-3.47 (m, 2H), 2.49-2.37 (m, 1H), 2.27-2.05 (m, 3H).

LCMS (m/z): 166 [M$^-$+1]

Synthesis of (S)-1-tert-butyl 2-methyl pyrrolidine-1,2-dicarboxylate (B)

To a stirring solution of A (35 g, 0.22 mol) in CH$_2$Cl$_2$ (175 mL) were added Et$_3$N (90 mL, 0.65 mol) followed by Boc-anhydride (56.9 mL, 0.26 mol) at 0° C. The reaction mixture was stirred at RT for 16 h. After consumption of the starting material (by TLC), the reaction was diluted with water (100 mL) and extracted with CH$_2$Cl$_2$ (2×100 mL). The organic layer was washed with water, brine, dried over Na$_2$SO$_4$ and concentrated. The resulting crude material was purified by silica gel column chromatography eluting with 30% EtOAc/Hexane to afford B (41 g, 95%).

¹H-NMR: (400 MHz, CDCl₃): δ 4.25-4.21 (m, 1H), 3.75 (s, 3H), 3.57-3.26 (m, 2H), 2.29-2.10 (m, 1H), 1.99-1.75 (m, 3H), 1.45 (s, 9H).
LCMS (m/z): 130 [(M⁺+1)-Boc]

Synthesis of 1-tert-butyl 2-methyl 2-((benzyloxy) methyl)pyrrolidine-1,2-dicarboxylate (C)

To a stirring solution of B (100 g, 0.43 mol) in THF (800 mL) was added LiHMDS (873 mL, 0.87 mol) at −78° C. and stirred for 1 h. To this BOM-chloride (93.2 mL, 0.65 mol) was added drop wise at −78° C. and stirred for 2 h at −20° C. After consumption of the starting material (by TLC), the reaction was quenched with sat. NH₄Cl solution at 0° C. The separated organic layer was washed with water, dried over Na₂SO₄ and concentrated to afford C (180 g, crude). This material was directly taken for the next step without further purification.
LCMS (m/z): 250 [(M⁺+1)-Boc]

Synthesis of 2-((benzyloxy)methyl)-1-(tert-butoxycarbonyl)pyrrolidine-2-carboxylic acid (D)

To a stirring solution of C (100 g, 0.28 mol) in methanol (200 mL) was added 2N NaOH solution (300 mL) at RT. The reaction mixture was heated to reflux for 4 h. After consumption of the starting material (by TLC), the solvent from the reaction was evaporated under reduced pressure and diluted with EtOAc (100 mL). The aqueous layer was acidified using citric acid solution and extracted with CH₂Cl₂ (2×250 mL). The separated organic layer was washed with water, dried over Na₂SO₄ and concentrated to afford D (60 g, 63%).
¹H-NMR: (400 MHz, CDCl₃): δ 7.37-7.32 (m, 5H), 4.61 (s, 2H), 4.05-3.88 (m, 2H), 3.65-3.42 (m, 2H), 2.54-2.46 (m, 2H), 1.95 (br s, 2H), 1.57 (s, 9H).
LCMS (m/z): 334 [M⁻−1]

Synthesis of 1-(tert-butoxycarbonyl)-2-(hydroxymethyl)pyrrolidine-2-carboxylic acid (Int-E)

To a stirring solution of D (10 g, 29.81 mmol) in methanol (300 mL) was added 50% wet 10% Pd/C (5 g) at RT and stirred for 24 h under H₂ atmosphere (balloon pressure). After consumption of the starting material (by TLC), the reaction mixture was filtered through a pad of celite and the pad was washed with methanol. The filtrate was concentrated under reduced pressure to afford Int-E (6 g, 82%).
¹H-NMR: (400 MHz, DMSO-d₆): δ 12.55 (br m, 1H), 3.99 (d, 1H), 3.88 (d, 1H), 7.65-7.60 (m, 1H), 3.51-3.45 (m, 1H), 3.39-3.34 (m, 1H), 2.32-2.14 (m, 1H), 1.98-1.69 (m, 3H), 1.39 (s, 9H).

Synthesis of 1-(pyrimidin-2-yl)propan-1-one (2)

To a stirring solution of 1 (15 g, 0.14 mol) in THF (150 mL) was added ethylmagnesium bromide (1M in THF) (171.4 mL, 0.17 mol) at 0° C. under nitrogen atmosphere slowly over a period of 15 min. After being stirred for 30 min, the reaction mixture was quenched with aqueous NH₄Cl solution and the aqueous layer was extracted with EtOAc. The separated organic layer was dried over anhydrous Na₂SO₄, filtered and concentrated under reduced pressure to obtain crude product, which was purified by silica gel column chromatography eluting with 50% EtOAc/hexane to afford 2 (8.5 g, 44%).

¹H-NMR: (400 MHz, CDCl₃): δ 8.95 (d, 2H), 7.47 (t, 1H), 3.26 (q, 2H), 1.25 (t, 3H).

Synthesis of (Z)-2-(1-((tert-butyldimethylsilyl)oxy) prop-1-en-1-yl)pyrimidine (3)

To a stirring solution of 2 (8.5 g, 62.5 mmol) in THF (170 mL) was added LiHMDS (1M in THF) (93.7 mL, 93.7 mmol) and stirred for 1 h. To this was added TES-Cl (12.5 mL, 75 mmol) at 0° C. under N₂ atmosphere and further stirred for 1 h. After consumption of the starting material (by TLC), the reaction was quenched with aqueous NH₄Cl solution and extracted with EtOAc. The separated organic layer was dried over anhydrous Na₂SO₄, filtered and concentrated under reduced pressure to afford 3 (10 g, 64%). The resulting crude material was directly used for the next step without further purification.

Synthesis of 2-bromo-1-(pyrimidin-2-yl)propan-1-one (4)

To a stirring solution of 3 (10 g, 0.04 mol) in THF:H₂O (100 mL, 4:1) was added NBS (5.6 g, 0.05 mol) at RT and stirred for 1 h. After consumption of the starting material (by TLC), the reaction mixture was concentrated under reduced pressure and obtained residue was diluted with EtOAc and washed with water. The separated organic layer was dried over anhydrous Na₂SO₄, filtered and concentrated under reduced pressure to obtain crude product, which was purified by silica gel column chromatography eluting with 30% EtOAc/hexane to afford 4 (6.5 g, 75.5%).
¹H-NMR: (400 MHz, CDCl₃): δ 8.97 (d, 2H), 7.52 (t, 1H), 5.92 (q, 1H), 2.79 (s, 1H), 1.99 (d, 3H).

Synthesis of 2-hydroxy-1-(pyrimidin-2-yl)propan-1-one (5)

To a stirring solution of 4 (6.5 g, 0.03 mol) in MeOH (65 mL) was added sodium formate (10.28 g, 0.15 mol) and heated to reflux for 8 h. After consumption of the starting material (by TLC), the reaction mixture was cooled to RT and solvent was removed under reduced pressure. The resulting crude material was purified by silica gel column chromatography eluting with 2% MeOH/CH₂Cl₂ to afford 5 (3.5 g, 76%).
¹H-NMR: (400 MHz, CDCl₃): δ 9.01 (d, 2H), 7.52 (t, 1H), 5.92 (q, 1H), 3.73 (br s, 1H), 3.41 (s, 1H), 2.78 (s, 2H), 1.55 (d, 3H).

Synthesis of 2-((tert-butyldimethylsilyboxy)-1-(pyrimidin-2-yl)propan-1-one (6)

To a stirring solution of 5 (3.5 g, 23 mmol) in CH₂Cl₂ (70 mL) was added imidazole (3.91 g, 57 mmol) followed by DMAP (281 mg, 2.30 mmol) at RT. The reaction mixture was cooled to 0° C., tow which TBS-Cl (5.18 g, 0.03 mol) was added and stirred at RT for 4 h. After consumption of the starting material (by TLC), the reaction mixture was diluted with CH₂Cl₂ and washed with water. The separated organic layer was dried over anhydrous Na₂SO₄, filtered and concentrated under reduced pressure to obtain a crude product, which was purified by silica gel column chromatography eluting with 20% EtOAc/hexane to afford 6 (3 g, 49%).
¹H-NMR: (400 MHz, CDCl₃: δ 8.93 (d, 2H), 7.45 (t, 1H), 5.59 (q, 1H), 1.52 (d, 3H), 0.89 (s, 9H), 0.09 (s, 6H).

Synthesis of 2-((tert-butyldimethylsilyboxy)-1-(pyrimidin-2-yl)propan-1-amine (7)

To a stirring solution of 6 (3.0 g, 11.27 mmol) in MeOH (60 mL) was added sodium acetate (1.84 g, 22.55 mmol) followed by ammonium carbonate (8.85 g, 56.3 mmol) and acetic acid (0.64 mL, 11.27 mmol) at RT. The reaction mixture was heated to reflux for 1 h, added NaCNBH$_3$ (1.41 g, 22.5 mmol) and continued reflux for another 6 h. After consumption of the starting material (by TLC), the reaction mixture was cooled to RT and volatiles were evaporated. Obtained residue was diluted with water and extracted with EtOAc. The separated organic layer was dried over anhydrous Na$_2$SO$_4$, filtered and concentrated under reduced pressure to get crude product, which was purified by silica gel column chromatography eluting with 2% MeOH/CH$_2$Cl$_2$ to afford 7 (2 g, 66.4%).
$^1$H-NMR: (400 MHz, DMSO-d$_6$): δ 8.91 (d, 1H), 8.85 (d, 1H), 7.48 (t, 1H), 5.71 (br m, 2H), 4.24 (t, 1H), 4.05 (d, 1H), 1.29 (d, 1H), 1.12 (d, 2H), 0.74 (s, 9H), 0.03 (s, 3H), 0.02 (s, 2H), 0.01 (s, 1H).
LCMS (m/z): 268 [M$^-$+1]

Synthesis of tert-butyl 2-((2-((tert-butyldimethylsilyboxy)-1-(pyrimidin-2-yl)propyl)carbamoyl)-2-(hydroxymethyl)pyrrolidine-1-carboxylate (8)

To a stirring solution of Int-E (2 g, 8.16 mmol) in CH$_2$Cl$_2$ (60 mL) was added compound 7 (2.39 g, 8.97 mmol), EDCI.HCl (2.33 g, 12.2 mmol) followed by HOBt (1.66 g, 12.24 mmol) and DIPEA (4.5 mL, 24.4 mmol) at 0° C. The reaction mixture was warmed to RT and stirred for 16 h. After consumption of the starting material (by TLC), the reaction mixture was diluted with CH$_2$Cl$_2$. The separated organic layer was washed with aqueous NaHCO$_3$ solution followed by aqueous NH$_4$Cl. The organic layer was dried over anhydrous Na$_2$SO$_4$, filtered and concentrated under reduced pressure to get crude product, which was purified by silica gel column chromatography eluting with 70% EtOAc/hexane to afford 8 (2.3 g, 57.5%).
$^1$H-NMR: (400 MHz, DMSO-d$_6$): δ 8.91 (d, 1H), 8.68 (d, 2H), 7.41 (br s, 1H), 5.74 (br t, 1H), 5.07-4.89 (m, 1H), 4.15-4.10 (m, 1H), 3.97-3.92 (m, 1H), 3.45-3.41 (m, 1H), 1.79-1.74 (m, 2H), 1.43-1.39 (m, 4H), 1.29-1.21 (m, 6H), 1.12 (d, 5H), 0.71 (s, 9H), 0.12 (t, 1H), 0.09 (s, 2H), 0.08 (s, 1H), 0.04 (s, 2H).
LCMS (m/z): 495.5 [M$^+$+1]
Mass: 495.5 [M$^+$+1]

Synthesis of tert-butyl 2-(2-((tert-butyldimethylsilthoxy)-1-(pyrimidin-2-yl)propyl)-1-oxo-2,5-diazaspiro[3.4]octane-5-carboxylate (9)

To a stirring solution of 8 (2.3 g, 4.65 mmol) in THF (23 mL) was added TPP (1.34 g, 5.12 mmol) followed by DTAD (1.6 g, 6.98 mmol) at 0° C. The reaction mixture was warmed to RT and stirred for 16 h. After consumption of the starting material (by TLC), the reaction mixture was concentrated under reduced pressure to get crude product, which was purified by silica gel column chromatography eluting with 25% EtOAc/hexane to afford 9 (1.2 g, 54.2%).
LCMS (m/z): 477.4 [M$^+$+1]
$^1$H-NMR: (400 MHz, DMSO-d$_6$): δ 8.82 (d, 2H), 7.49 (t, 1H), 4.72 (d, 1H), 4.31 (q, 1H), 3.62 (br s, 2H), 3.25-3.19 (m, 1H), 2.24-2.05 (m, 2H), 1.85-1.81 (m, 2H), 1.42 (br s, 1H), 1.25 (t, 3H), 0.92 (s, 8H), 0.75 (s, 9H), 0.02 (s, 3H).

Synthesis of tert-butyl 2-(2-hydroxy-1-(pyrimidin-2-yl)propyl)-1-oxo-2,5-diazaspiro[3.4]octane-5-carboxylate (10)

To a stirring solution of 9 (1.0 g, 2.10 mmol) in THF (20 mL) was added TBAF (1M in THF) (6.3 mL, 6.30 mmol) at 0° C. under N$_2$ atmosphere and stirred for 1 h. After consumption of the starting material (by TLC), the reaction mixture was quenched with ice water and extracted with EtOAc. The separated organic layer was dried over anhydrous Na$_2$SO$_4$, filtered and concentrated under reduced pressure to obtain crude product, which was purified by silica gel column chromatography eluting with 5% MeOH/CH$_2$Cl$_2$ to afford 10 (0.35 g, 46%).
$^1$H-NMR: (400 MHz, DMSO-d$_6$): δ 8.81 (d, 2H), 7.49 (t, 1H), 4.81 (d, 1H), 4.65 (d, 1H), 4.25-4.20 (m, 1H), 3.64-3.51 (m, 2H), 3.34 (s, 1H), 3.25-3.20 (m, 1H), 2.25-2.20 (m, 2H), 1.87-1.82 (m, 2H), 1.19 (d, 3H), 0.97 (s, 9H).
LCMS (m/z): 363.3 [M$^+$+1]

Synthesis of 2-(2-hydroxy-1-(pyrimidin-2-yl)propyl)-2,5-diazaspiro[3.4]octan-1-one (Compound Y)

To a stirring solution of 10 (0.3 g, 0.82 mmol) in CH$_2$Cl$_2$ (6 mL) was added molecular sieves (0.3 g) followed by BF$_3$-etherate (0.31 mL, 2.48 mmol) at 0° C. and stirred at RT for 1 h. After consumption of the starting material (by TLC), the reaction mixture was filtered and obtained residue was dissolved in MeOH and washed with CH$_2$Cl$_2$. The volatiles were evaporated under reduced pressure to obtain crude product, which was purified by silica gel column chromatography eluting with 8% MeOH/CH$_2$Cl$_2$ to afford Compound Y (0.12 g, 55%).
$^1$H-NMR: (400 MHz, DMSO-d$_6$): δ 8.81 (d, 2H), 7.49 (t, 1H), 4.81 (d, 1H), 4.65 (d, 1H), 4.25-4.20 (m, 1H), 3.64-3.51 (m, 2H), 3.12-3.01 (m, 2H), 2.15-2.10 (m, 2H), 1.87-1.82 (m, 2H), 1.19 (d, 3H).
LCMS (m/z): 263.1 [M$^+$+1]

Preparation of Key Intermediates, Schemes I-1 to I-7

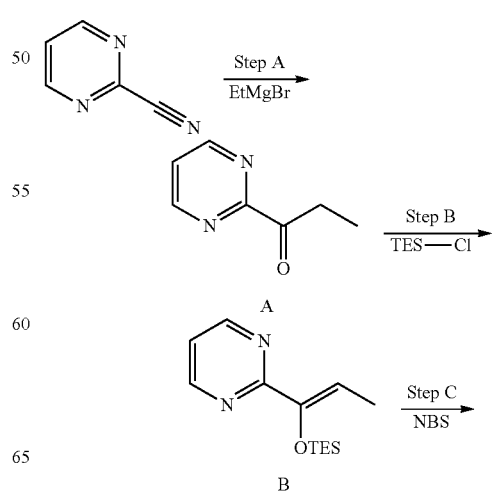

Scheme I-1

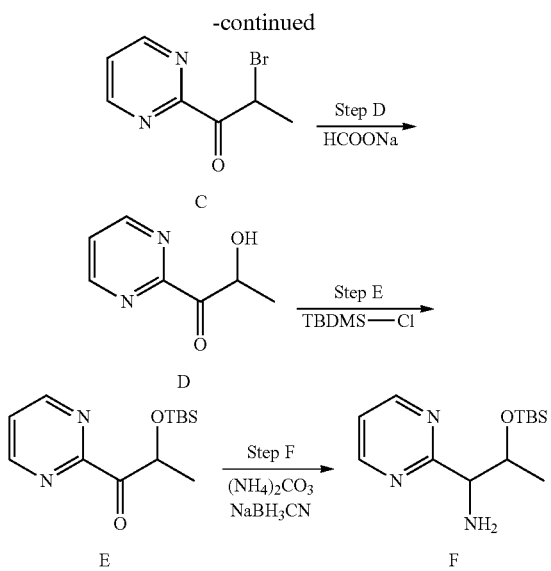

Synthesis of 1-(pyrimidin-2-yl)propan-1-one, A

Referring to Scheme I-1, to a stirring solution of pyrimidine-2-carbonitrile (25 g, 238 mmol) in THF (180 mL) was added ethyl magnesium bromide (1M in THF, 37.9 g, 285 mmol) at 0° C. and stirred for 2 h at RT. After completion of starting material (by TLC), the reaction mixture was diluted with saturated ammonium chloride solution and EtOAc (150 mL). The separated organic layer was washed with brine solution (2×100 mL). The extracted organic layer was dried over anhydrous $Na_2SO_4$, filtered and concentrated under reduced pressure to afford crude material which was purified by column chromatography eluting 30% EtOAc/hexane to afford A (18.3 g, 57%) as an off-white solid.

$^1$H-NMR: (400 MHz, DMSO-$d_6$): δ 9.00 (d, J=5.2 Hz, 2H), 7.70 (t, J=4.8 Hz, 1H), 3.20-3.15 (m, 2H), 1.09 (t, J=7.2 Hz, 3H).

LCMS m/z: 137 [M$^+$+1].

Synthesis of (Z)-2-(1-((triethylsilyl)oxy)prop-1-en-1-yl)pyrimidine (B)

To a stirring solution of A (14 g, 103 mmol) in dry THF (140 mL) was added LiHMDS (1M in THF, 206 mL, 206 mmol) slowly at 0° C. and stirred for 30 min. After added chloro triethylsilane (24.8 g, 165 mmol) in THF (50 mL) dropwise at 0° C. and stirred 1 h. After completion of starting material (by TLC), the reaction mixture was diluted with saturated ammonium chloride solution (100 mL) and EtOAc (150 mL). The separated organic layer was washed with brine solution (2×100 mL). The organic layer was dried over anhydrous $Na_2SO_4$, filtered and concentrated under reduced pressure to afford crude material which was purified by column chromatography eluting 20% EtOAc/hexane to afford B (23 g, 89.4%) as yellow thick syrup.

$^1$H-NMR: (400 MHz, DMSO-$d_6$): δ 8.75 (d, J=4.8 Hz, 2H), 7.32 (t, J=4.8 Hz, 1H), 6.36-6.31 (m, 1H), 1.77 (d, J=7.2 Hz, 3H), 0.95-0.87 (m, 9H), 0.71-0.65 (m, 6H).

Synthesis of 2-bromo-1-(pyrimidin-2-yl)propan-1-one (C)

To a stirring solution of B (23 g, 92 mmol) in THF/$H_2O$ (184 mL/46 mL) were added N-bromosuccinamide (18 g, 101 mmol) slowly at 0° C. and stirred for 3 h at RT. After completion of starting material (by TLC), the reaction mixture was diluted with $H_2O$ and EtOAc (100 ml/150 mL). The separated organic layer was washed with hypo solution (2×100 mL) followed by brine solution (2×100 mL). The organic layer was dried over anhydrous $Na_2SO_4$, filtered and concentrated under reduced pressure to afford crude material which was purified by column chromatography eluting 15% EtOAc/hexane to afford C (11.5 g, 58%) as yellow thick syrup.

$^1$H-NMR: (400 MHz, DMSO-$d_6$): δ 9.06 (d, J=4.8 Hz, 2H), 7.75 (t, J=4.8 Hz, 1H), 5.97-5.92 (m, 1H), 1.83 (d, J=6.4 Hz, 3H).

Synthesis of 2-hydroxy-1-(pyrimidin-2-yl)propan-1-one (D)

To a stirring solution of C (11.5 g, 53.4 mmol) in MeOH (80 mL) was added sodium formate (14.5 g, 214 mmol) and stirred the reaction mass at 80° C. for 6 h. After completion of reaction (by TLC), the reaction mixture was evaporated under reduced pressure to give crude product, which was purified by column chromatography eluting 50% EtOAc/n-hexane to afford D (5.0 g, 61.6%) as colorless liquid.

$^1$H-NMR: (400 MHz, DMSO-$d_6$): δ 8.73 (d, J=5.2 Hz, 2H), 7.55 (t, J=4.8 Hz, 1H), 5.28-5.26 (m, 1H), 1.24 (d, J=6.4 Hz, 1H), 0.99 (d, J=6.4 Hz, 3H)

Synthesis of (2((tert-butyldimethylsilyl)oxy)-(pyrimidin-2-yl)propan-1-one (E)

To a stirring solution of D (5 g, 32.8 mmol) in DCM (50 mL) were added imidazole (5.5 g, 82.2 mmol), DMAP (800 mg, 0.65 mmol) at 0° C. and stirred for 10 min. After added TBDMS-Cl (7.38 g, 49.2 mmol) at 0° C. and stirred at RT for 12 h. After completion of starting material (by TLC), diluted the reaction mass with $H_2O$ (50 mL). The separated organic layer was washed with brine solution (2×50 mL), The organic layer was dried over anhydrous $Na_7SO_4$, filtered and concentrated under reduced pressure to afford crude material which was purified by column chromatography eluting 20% EtOAc/hexane to afford E (6 g, 68.8%) as an off-white solid.

$^1$H-NMR: (400 MHz, CDCl$_3$): δ 9.00 (d, J=5.2 Hz, 2H), 7.71 (t, J=4.8 Hz, 1H), 5.47-5.42 (m, 1H), 1.35 (d, J=6.8 Hz, 3H), 0.79 (s, 9H), 0.05 (s, 6H).

Synthesis of (2-((tert-butyldimethylsilyl)oxy)-1-(pyrimidin-2-yl)propan-1-amine (F)

To a stirring solution of E (6 g, 22.5 mmol) in MeOH (50 mL) were added sodium acetate (3.69 g, 45.1 mmol), ammonium carbonate (21 g, 135 mmol), AcOH (1.28 mL, 22.5 mmol) at RT and stirred the reaction mixture at 90° C. for 2 h. The temperature of the reaction was cooled to RT and added sodium cyanoborohydride (2.84 g, 45.1 mmol) slowly and stirred at 90° C. for 6 h. After completion of reaction (by TLC), evaporated MeOH under reduced pressure. The crude residue was diluted with water (20 mL) and extracted with DCM (2×50 mL). The organic layer was dried over anhydrous $Na_2SO_4$, filtered and concentrated under reduced pressure to afford crude material was purified by column chromatography eluting 5% MeOH/DCM to afford F (4.2 g, 69.6%) as semi solid.

$^1$H-NMR: (400 MHz, CDCl$_3$): δ 8.83 (d, J=4.8 Hz, 2H), 7.40 (t, J=5.2 Hz, 1H), 4.13 (t, J=6.4 Hz, 2H), 3.90 (d, J=6.4 Hz, 2H), 1.12 (d, J=6.4 Hz, 3H), 0.70 (s, 9H), 0.02 (s, 6H).

Scheme I-2

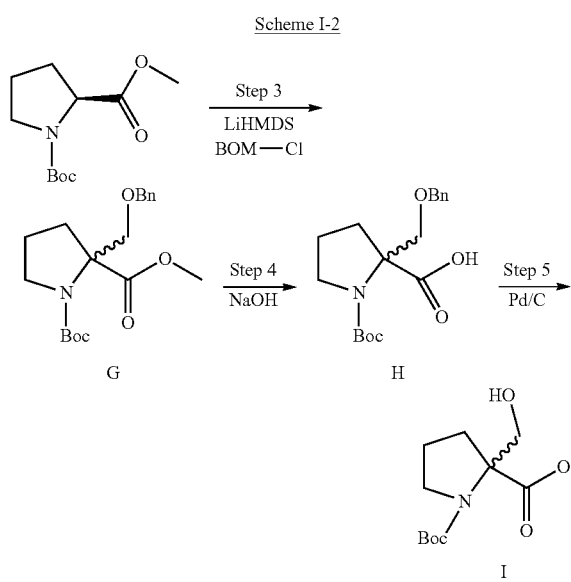

Synthesis of 1-tert-butyl 2-methyl 2-((benzyloxy)methyl)pyrrolidine-1,2-dicarboxylate (G)

To a stirring solution of t-BOC proline methyl ester (25 g, 109 mmol) in THF (250 mL) was added LiHMDS (240 mL, 240 mmol) at −20° C. and stirred for 2 h. To this BOM-chloride (23 mL, 163 mmol) was added drop wise at −30° C. and stirred for 2 h. After consumption of the starting material (by TLC), the reaction was quenched with aqueous NH$_4$Cl solution (100 mL) and extracted with EtOAc (2×200 mL). The combined organic layer was washed with water (2×150 mL) followed by brine solution (2×100 mL). The organic layer was dried over Na$_2$SO$_4$ and concentrated to obtain crude compound which was purified by column chromatography by eluting 10% EtOAC/n-hexane to afford compound G (30 g, 79%) as thick syrup.

$^1$H-NMR: (500 MHz, DMSO-d$_6$): δ 7.36-7.22 (m, 5H), 4.59-4.48 (m, 2H), 4.02-3.88 (m, 1H), 3.63 (s, 3H), 3.49-3.35 (m, 2H), 3.34-3.30 (m, 1H), 2.31-2.23 (m, 1H), 2.04-1.89 (m, 2H), 1.82-1.78 (m, 1H).

LCMS (m/z): 249.4 [(M$^+$+1)-Boc].

Synthesis of 2-((benzyloxy)methyl)-1-(tert-butoxycarbonyl)pyrrolidine-2-carboxylic acid (H)

To a stirring solution of compound G (30 g, 86 mmol) in methanol (70 mL) was added NaOH solution (6.88 g in 70 mL H$_2$O) at RT. The reaction mixture was heated to 70° C. for 16 h. After consumption of the starting material (by TLC), the solvent from the reaction was evaporated under reduced pressure and diluted with EtOAc (2×200 mL). The separated aqueous layer was acidified using citric acid solution (pH ~3) and extracted with EtOAc (2×250 mL). The combined organic layer was dried over Na$_2$SO$_4$ and concentrated to afford crude which was triturated with n-hexane to obtain compound H (25 g, 86.8%) as off-white solid.

$^1$H-NMR: (400 MHz, DMSO-d$_6$): δ 12.35 (br s, 1H), 7.37-7.29 (m, 5H), 4.56-4.48 (m, 2H), 4.06-4.00 (m, 1H), 3.92-3.89 (m, 1H), 3.66-3.45 (m, 1H), 3.37-3.28 (m, 1H), 2.31-2.20 (m, 1H), 2.05-1.97 (m, 1H), 1.87-1.75 (m, 2H), 1.38 (s, 9H).

LCMS (m/z): 335.3 [M$^1$+1].

Synthesis of 1-(tert-butoxycarbonyl)-2-(hydroxymethyl)pyrrolidine-2-carboxylic acid (I)

To a stirring solution of compound H (25 g, 74 mmol) in methanol (150 mL) was added 50% wet 10% Pd/C (7 g) at RT and stirred for 10 h under H$_2$ atmosphere. After consumption of the starting material (by TLC), the reaction mixture was filtered through a pad of celite and the pad was washed with methanol (100 mL). Obtained filtrate was concentrated under reduced pressure to afford compound I (15 g, 82.8%) as white solid.

$^1$H-NMR: (400 MHz, DMSO-d$_6$): δ 4.66 (br s, 1H), 3.96-3.83 (m, 1H), 3.63-3.59 (m, 1H), 3.49-3.41 (m, 1H), 3.34-3.25 (m, 1H), 2.30-2.17 (m, 1H), 1.95-1.72 (m, 3H), 1.38 (s, 9H).

Scheme I-3

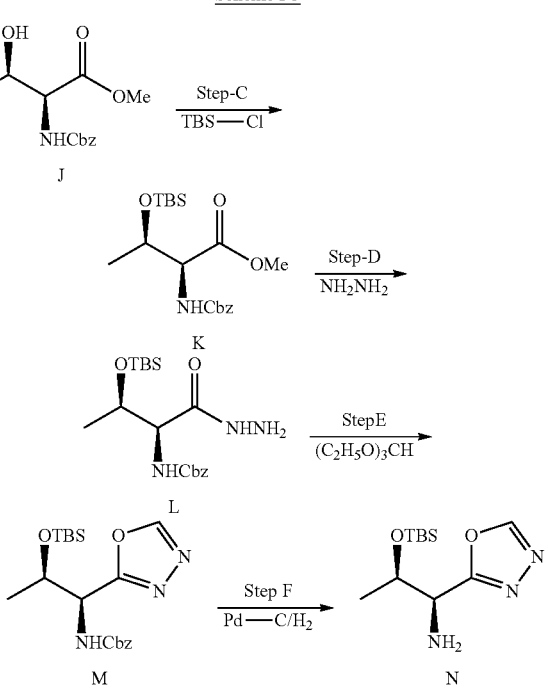

Synthesis of (2S, 3R)-methyl 2-4(benzyloxy)carbonyl)amino)-3-((tert-butyldimethylsilyl)oxy)butanoate (K)

Referring to Scheme I-3, to a stirring solution of J (50 g, 187 mmol) in DMF (400 mL) were added DIPEA (86 mL, 468 mmol) TBDMS-Cl (3166 mL, 224 mmol) at 0° C. and stirred at RT for 12 h. After completion of starting material (by TLC), diluted the reaction mass with EtOAc (500 ml). The separated organic layer was washed with (2×200 mL) of Water followed by brine solution (2×100 mL). The organic layer was dried over anhydrous Na$_2$SO$_4$, filtered and concentrated under reduced pressure to afford crude material was purified by column chromatography eluting 10% EtOAc/hexane to afford K (50 g, 70.1%) as colorless syrup.

$^1$H-NMR: (400 MHz, CDCl$_3$): δ 7.39-7.32 (m, 5H), 5.43 (d, J=9.6 Hz, 1H), 5.14 (s, 2H), 4.45-4.43 (m, 1H), 4.29-4.26 (m, 1H), 3.72 (s, 3H), 1.21 (d, J=6.0 Hz, 3H), 0.83 (s, 9H), 0.09 (s, 6H).

LCMS m/z: 382.2 [M$^+$+1].

Synthesis of benzyl((2S, 3R)-3-((tert-butyldimethyl-silyl)oxy)-1-hydrazinyl-1-oxobutan-2-yl)carbamate (L)

A solution of K (50 g, 131 mmol) in EtOH (400 mL) was added hydrazine hydrate (32.8 g, 656 mmol), at RT and after stirred at 90° C. for 24 h. After completion of starting material (by TLC), evaporated ethanol under reduced pressure. The crude residue was diluted with water (100 mL) and EtOAc (500 mL). After the separated organic layer was washed with (2×100 mL) of water followed by brine solution (1×100 mL). Dried over anhydrous $Na_2SO_4$, filtered and concentrated under reduced pressure. Obtained crude material was purified by column chromatography by eluting with 20% EtOAc/hexane to afford L (25 g, 50%) as colorless thick syrup. $^1$H-NMR: (400 MHz, DMSO-$d_6$): δ 9.10 (s, 1H), 7.36-7.30 (m, 5H), 6.83 (d, J=9.6 Hz, 1H), 5.02 (s, 2H), 4.19 (s, 2H), 4.05-4.02 (m, 1H), 3.97-3.93 (m, 1H), 1.05 (d, J=6.0 Hz, 3H), 0.81 (s, 9H), 0.01 (s, 6H).

Synthesis of benzyl((1S, 2R)-2-((tert-butyldimethyl-silyl)oxy)-1-(1,3,4-oxadiazol-2-yl)propyl)carbamate (M)

A solution of L (25 g, 65.6 mmol) in triethyl orthoformate (250 mL) was added p-TSA (catalytic, 250 mg) at RT and after stirred at 80° C. for 3 h. After completion of starting material (by TLC), evaporated triethyl orthoformate under reduced pressure. The crude residue was purified by column chromatography eluting 10% EtOAc/hexane to afford M (15 g, 58%) as thick syrup.

$^1$H-NMR: (500 MHz, DMSO-$d_6$): δ 9.22 (s, 1H), 7.85 (d, J=9.5 Hz, 1H), 7.36-7.31 (m, 5H), 5.05 (s, 2H), 4.96-4.93 (m, 1H), 4.25 (t, J=6.0 Hz, 1H), 1.23 (d, J=6.0 Hz, 3H), 0.80 (s, 9H), 0.10 (s, 6H).
LCMS m/z: 392.4 [M$^+$+1].

Synthesis of (1S, 2R)-2-((tert-butyldimethylsilyl)oxy)-1-(1,3,4-oxadiazol-2-yl)propan-1-amine (N)

To a stirring solution of M (15 g, 38.3 mmol) in methanol (200 mL) was added 50% wet 10% Pd/C (5 g) and stirred under $H_2$ atmosphere (balloon pressure) for 4 h at RT. The reaction mixture was filtered through a pad of celite and triturated with methanol (100 mL). The filtrate was concentrated under reduced pressure to afford N (10 g, crude) as thick syrup.

$^1$H-NMR: (500 MHz, DMSO-$d_6$): δ 9.15 (s, 1H), 4.11 (t, J=5.0 Hz, 1H), 4.03 (d, J=2.0 Hz, 1H), 2.05 (br s, 2H), 1.17 (d, J=6.0 Hz, 3H), 0.76 (s, 9H), 0.02 (s, 6H).
LCMS m/z: 258.3 [M$^+$+1].

Scheme I-4

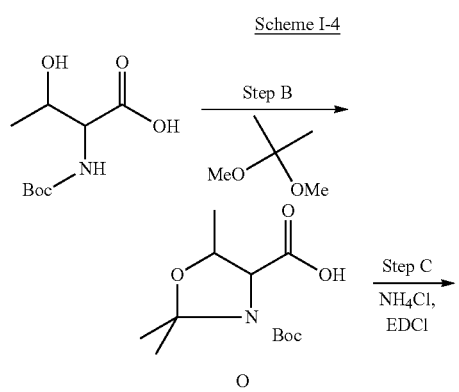

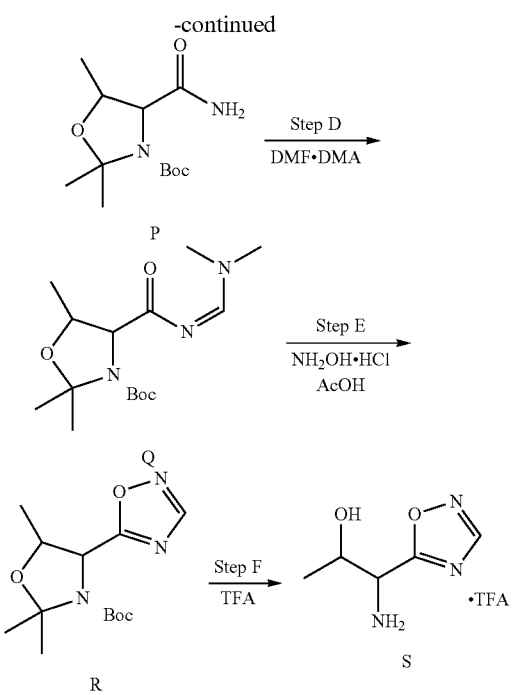

Synthesis of 3-(tert-butoxycarbonyl)-2,2,5-trimethyloxazolidine-4-carboxylic acid (O)

To a stirring solution of N—BOC threonine (15 g, 59.28 mmol) in THF (150 mL) was added PPTS (1.47 g, 5.92 mmol) followed by 2,2-dimethoxy propane (21.79 mL, 0.17 mol) at 0° C. under $N_2$ atmosphere. The reaction mixture was stirred at RT for 16 h. The reaction mixture was again heated to reflux for 6 h. The reaction mixture was diluted with aqueous $NaHCO_3$ solution and washed with EtOAc (1×100 mL). Aqueous layer was acidified using citric acid solution (pH ~2) and extracted with $CH_2Cl_2$ (2×100 mL). The organic layer was washed with brine, dried over anhydrous $Na_2SO_4$ and concentrated under vacuum to afford compound O (18 g, crude).

$^1$H-NMR: (400 MHz, DMSO-$d_6$): δ 13.25 (br s, 1H), 4.11-4.05 (m, 1H), 3.79 (d, 1H), 1.50 (s, 3H), 1.67 (s, 3H), 1.45 (s, 9H), 1.29 (d, 3H).

Synthesis of tert-butyl 4-carbamoyl-2,2,5-trimethyl-oxazolidine-3-carboxylate (P)

To a stirring solution of compound O (18 g, 69.4 mmol) in $CH_2Cl_2$ (180 mL) was added HOBt (14.16 g, 0.104 mol), EDCI.HCl (19.88 g, 0.104 mol) followed by $NH_4Cl$ (5.56 g, 0.104 mol) and DIPEA (31.9 mL, 0.173 mol) at 0° C. The reaction mixture was stirred at RT for 16 h. After consumption of the starting material (by TLC), the reaction mixture was washed with aqueous citric acid, $NaHCO_3$ followed by brine. Organic layer was dried over anhydrous $Na_2SO_4$ and concentrated under reduced pressure to give crude; which was purified by silica gel column chromatography eluting with 2% MeOH/$CH_2Cl_2$ to afford compound P (13 g, 72.5%).

$^1$H-NMR: (400 MHz, DMSO-$d_6$): δ 7.51 (br s, 1H), 7.14 (br s, 1H), 3.97-3.95 (m, 1H), 3.71 (d, 1H), 1.51 (s, 6H), 1.34 (s, 9H), 1.24 (d, 3H).
LCMS (ESI): 159.1 [(M$^+$+1)-Boc]

Synthesis of (Z)-tert-butyl 4-(((dimethylamino)methylene)carbamoyl)-2,2,5-trimethyloxazolidine-3-carboxylate (O)

A solution of compound P (13 g, 50.3 mmol) in DMF.DMA (130 mL) was stirred at reflux temperature for 3 h under N₂ atmosphere. After consumption of the starting material (by TLC), the reaction mixture was concentrated under reduced pressure to afford compound Q (15.7 g, crude). This crude material was directly taken for the next step without further purification.

Synthesis of tert-butyl 2,2,5-trimethyl-4-(1,2,4-oxadiazol-5-yl)oxazolidine-3-carboxylate To a stirring solution of compound Q (15.7 g, 50.09 mmol) in ethanol (157 mL) was added hydroxylamine hydrochloride (6.96 g, 0.10 mol) under N₂ atmosphere. The reaction mixture was heated to reflux and stirred for 2 h. After consumption of the starting material (by TLC), acetic acid (28.6 mL, 0.50 mol) was added to the reaction mixture and then refluxed for 16 h. The solvents from the reaction mixture was evaporated under vacuum to give crude; which was purified by silica gel column chromatography eluting with 10% EtOAc/Hexane to afford compound R (4.5 g, 32%).

¹H-NMR: (400 MHz, DMSO-d₆): δ 6.35 (s, 2H), 4.61 (d, 1H), 4.22-4.15 (m, 1H), 1.55 (s, 6H), 1.37 (s, 2H), 1.25 (d, 3H), 1.21 (s, 6H).

LCMS (ESI): 284 [M+1]

Mass (m/z): 283 [M⁻]

Synthesis of 1-amino-1-(1,2,4-oxadiazol-5-yl)propan-2-ol (S)

To a stirring solution of compound R (5 g, 17.6 mmol) in water (25 mL) was added trifluoroacetic acid (25 mL). The reaction mixture was stirred at RT for 5 h. After consumption of the starting material (by TLC), the reaction mixture was concentrated under vacuum. The residue was dissolved in water and neutralized with aqueous NaHCO₃. The solvent from the reaction mixture was evaporated under vacuum and extracted with 5% MeOH/CH₂Cl₂ (3×100 mL). The organic layer was concentrated under reduced pressure to afford compound S (2.5 g, crude).

¹H-NMR: (400 MHz, D₂O): δ 8.84 (s, 1H), 4.05 (d, 1H), 3.98-3.95 (m, 1H), 3.67 (s, 1H), 3.58 (d, 1H), 1.15 (d, 3H), 1.12 (d, 3H).

LCMS (ESI): 144.1 [Mⁱ+1]

Scheme I-5

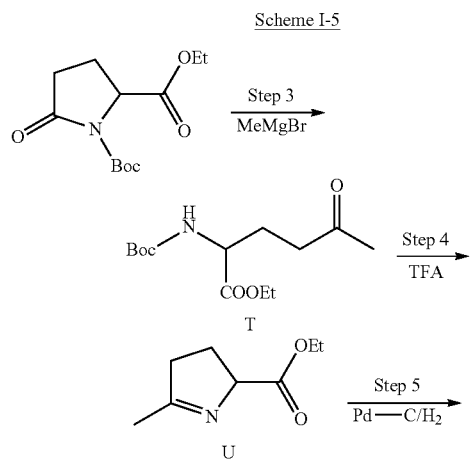

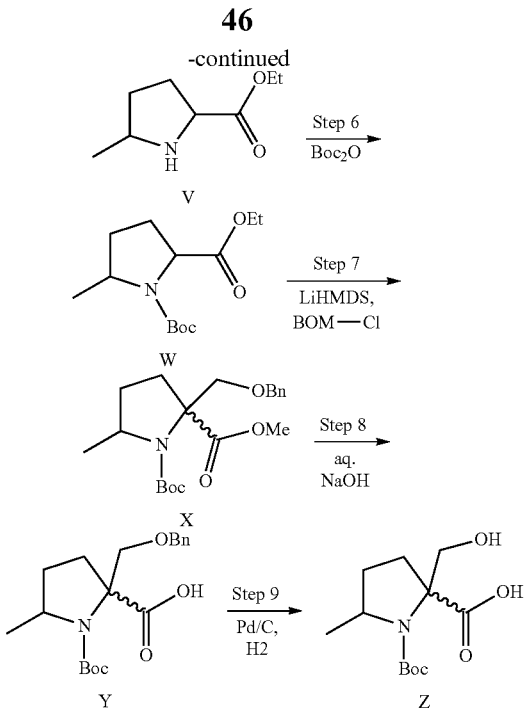

Synthesis of ethyl 2-((tert-butoxycarbonyl)amino)-5-oxohexanoate (T)

To a stirring solution of 1-tert-butyl 2-ethyl 5-oxopyrrolidine-1,2-dicarboxylate (12 g, 46.6 mmol) in THF (120 mL) under inert atmosphere was added MeMgBr (3M in ether) (20.2 mL, 60.6 mmol) at 0° C. and stirred for 2 h. After consumption of the starting material (by TLC), the reaction mixture was quenched with aqueous NH₄Cl solution and the aqueous layer was extracted with EtOAc (2×200 mL). The combined organic extracts were dried over anhydrous Na₂SO₄ and concentrated under reduced pressure. The crude residue obtained was purified by silica gel column chromatography eluting with 20% EtOAc/Hexane to afford compound T (10 g, 79%).

¹H-NMR: (400 MHz, CDCl₃): δ 5.14 (br s, 1H), 4.23 (q, 2H), 2.62-2.47 (m, 2H), 2.17 (s, 4H), 1.91-1.82 (m, 1H), 1.45 (s, 10H), 1.26 (t, 3H).

Synthesis of ethyl 5-methylpyrrolidine-2-carboxylate (V)

To a stirring solution of compound T (10 g, 36.7 mmol) in CH₂Cl₂ (50 mL) was added TFA (14.89 mL, 194.6 mmol) at 0° C. After being stirred for 2 h at RT, the reaction mixture was concentrated under reduced pressure to get compound U. Obtained material was dissolved in ethanol (100 mL) and 10% Pd/C (50% wet, 3 g) under N₂ atmosphere. The reaction mixture was stirred under H₂ atmosphere (balloon pressure) for 16 h. The reaction mixture was filtered through a pad of celite and filtrate was concentrated under reduced pressure to afford compound V (15 g, crude). This material was directly taken for the next step without further purification.

¹H-NMR: (500 MHz, DMSO-d₆): 4.4 (m, 1H), 4.2 (m, 2H), 3.6 (m, 1H), 2.3 (m, 1H), 2.1 (m, 2H), 1.6 (m, 1H), 1.3 (d, 3H), 1.2 (t, 3H).

LCMS m/z: 158.1 [M⁺+1].

Synthesis of 1-tert-butyl 2-ethyl 5-methylpyrrolidine-1,2-dicarboxylate (W)

To a stirring solution of compound V (30 g, 191 mmol) in CH$_2$Cl$_2$ (150 mL) was added DMAP (23.3 g, 191 mmol) followed by Et$_3$N (79.8 mL, 573 mmol) and Boc-anhydride (104 mL, 477 mmol) at 0° C. The reaction mixture was stirred at RT for 16 h. The reaction mixture was diluted with CH$_2$Cl$_2$ (50 mL) and washed with water (2×150 mL) followed by brine. The separated organic layer was dried over anhydrous Na$_2$SO$_4$ and concentrated under vacuum. Obtained crude material was purified by column chromatography eluting with 6% EtOAc/Hexane to afford compound W (12 g, 82%) as pale yellow liquid.

$^1$H-NMR: (500 MHz, DMSO-d$_6$): δ 4.13-3.86 (m, 4H), 2.15 (d, J=3.5 Hz, 1H), 1.99-1.82 (m, 2H), 1.52 (t, J=4.5 Hz, 1H), 1.38 (s, 9H), 1.24 (t, J=5.5 Hz, 3H), 1.16 (d, J=6.5 Hz, 3H)

LCMS (m/z): 258 [(M$^-$+1).

Synthesis of 1-tert-butyl 2-ethyl 2-((benzyloxy)methyl)-5-methylpyrrolidine-1,2-dicarboxylate (X)

To a stirring solution of compound W (8.0 g, 31.12 mmol) in THF (70 mL) was added LiHMDS (59 mL, 41.72 mmol) at −78° C. and stirred for 2 h. To this BOM-chloride (6.56 mL, 41.72 mmol) was added drop wise and stirred for 2 h at −30° C. After consumption of the starting material (by TLC), the reaction was quenched with aqueous NH$_4$Cl solution (20 mL) and extracted with DCM (30 mL). The separated organic layer was dried over Na$_2$SO$_4$ and concentrated to afford crude material was purified by column chromatography eluting with 10% EtOAc/Hexane to afford compound X (11 g, 94.2%) as pale yellow liquid.

$^1$H-NMR: (500 MHz, DMSO-d$_6$): δ 7.33-7.25 (m, 5H), 4.38 (d, J=10.5 Hz, 2H), 4.08-3.98 (m, 1H), 3.88 (d, J=9.5 Hz, 2H), 2.20-2.08 (m, 2H), 1.38 (s, 9H), 1.37-1.29 (m, 4H), 1.19 (t, J=7.5 Hz, 3H), 1.14-1.10 (m, 3H).

LCMS (m/z): 378 (M$^+$+1).

Synthesis of 2-((benzyloxy)methyl)-1-(tert-butoxycarbonyl)-5-methylpyrrolidine-2-carboxylic acid (Y)

To a stirring solution of compound X (11 g, 29.17 mmol) in CH$_3$OH/THF (22 mL/20 mL) were added 2N NaOH solution (33 mL) at RT. The reaction mixture was heated to 65° C. for 8 h. After consumption of the starting material (by TLC), the solvent from the reaction was evaporated under reduced pressure and diluted with EtOAc (50 mL). The aqueous layer was acidified using citric acid solution and extracted with CH$_2$Cl$_2$ (2×100 mL). The separated organic layer was washed with water (1×50 mL), dried over Na$_2$SO$_4$ and concentrated to afford compound Y (8 g, 80%).

$^1$H-NMR: (400 MHz, DMSO-d$_6$): δ 12.58 (s, 1H), 7.34-7.28 (m, 5H), 4.54-4.47 (m, 2H), 4.05-3.87 (m, 2H), 3.70-3.62 (m, 1H), 2.28-2.08 (m, 3H), 1.46-1.37 (m, 1H), 1.28 (s, 9H).

LCMS (m/z): 350 [M$^+$+1].

Synthesis of 1-(tert-butoxycarbonyl)-2-(hydroxymethyl)-5-methylpyrrolidine-2-carboxylic acid (Z)

To a stirring solution of compound Y (8 g, 1.45 mmol) in methanol (40 mL) was added 50% wet Pd/C (4 g) under N$_2$ atmosphere. The reaction mixture was stirred under H$_2$ atmosphere (balloon pressure) at RT for 16 h. After consumption of the starting material (by TLC), the reaction mixture was filtered through a pad of celite and the pad was washed with methanol. Obtained filtrate was concentrated under reduced pressure to afford crude compound which was triturated with n-pentane to obtained compound Z (4.5 g, 75.2%) as white solid.

$^1$H-NMR: (500 MHz, DMSO-d$_6$): δ 12.37 (br s, 1H), 4.61 (br s, 1H), 3.95-3.85 (m, 3H), 2.18-2.06 (m, 3H), 1.44-1.41 (m, 1H), 1.38 (s, 9H), 1.09 (d, J=6.0 Hz, 3H); LCMS (ESI): 260 [M$^+$+1]

Scheme I-6

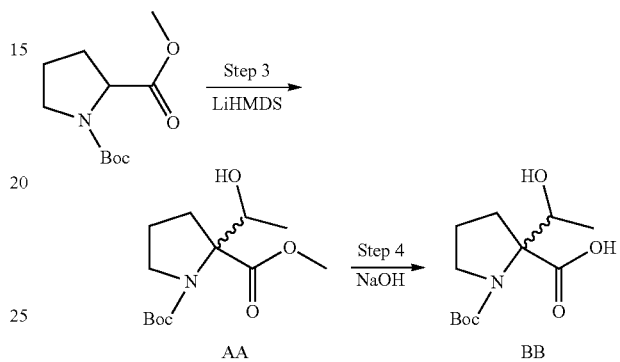

Synthesis of 1-(tert-butyl) 2-methyl 2-(1-hydroxyethyl)pyrrolidine-1,2-dicarboxylate (AA)

To a stirring solution of N—BOC proline methyl ester (30 g, 131 mmol) in THF (100 mL) was added LiHMDS (323 mL, 327 mmol) at −20° C. and stirred for 30 min. To this acetaldehyde (12.3 mL, 196 mmol) was added drop wise at −20° C. and stirred for 2 h. After consumption of the starting material (by TLC), the reaction was quenched with aqueous NH$_4$Cl solution (100 mL) and extracted with EtOAc (2×200 mL). The combined organic layer was washed with brine solution (2×150 mL). The organic layer was dried over Na$_2$SO$_4$ and concentrated to obtain crude compound which was purified by column chromatography by eluting 10% EtOAc/n-hexane to afford compound AA (30 g, 83.8%) as thick syrup.

$^1$H-NMR: (400 MHz, CDCl$_3$): δ 5.82 (d, J=10.0 Hz, 1H), 4.71-4.11 (m, 1H), 3.76 (s, 3H), 3.66-3.57 (m, 1H), 3.45-3.36 (m, 1H), 2.51-2.46 (m, 1H), 2.33-2.24 (m, 1H), 2.04-1.97 (m, 1H), 1.95-1.83 (m, 1H), 1.49 (s, 9H), 1.20-1.11 (m, 3H).

LCMS (m/z): 274.3 [M$^+$+1].

Synthesis of 1-(tert-butoxycarbonyl)-2-(1-hydroxyethyl)pyrrolidine-2-carboxylic acid (BB)

To a stirring solution of compound AA (30 g, 109 mmol) in methanol (50 mL) was added NaOH solution (8.72 g in 10 mL H$_2$O, 218 mmol) at RT. The reaction mixture was heated to 70° C. for 12 h. After consumption of the starting material (by TLC), the solvent from the reaction was evaporated under reduced pressure and diluted with DCM (200 mL). The separated aqueous layer was acidified using citric acid solution (pH ~3) and extracted with DCM (2×250 mL). The combined organic layer was washed with brine solution (1×100 mL). The organic layer was dried over Na$_2$SO$_4$ and concentrated to afford compound BB (9.5 g, 33.6%) as brown solid.

$^1$H-NMR: (400 MHz, DMSO-d$_6$): δ 4.53-4.45 (m, 1H), 3.59-3.48 (m, 1H), 3.25-3.19 (m, 1H), 2.33-2.16 (m, 1H), 1.90-1.78 (m, 3H), 1.38 (s, 9H), 0.95 (d, J=6.4 Hz, 3H).

LCMS (m/z): 258.2 [M$^-$−1].

Scheme I-7

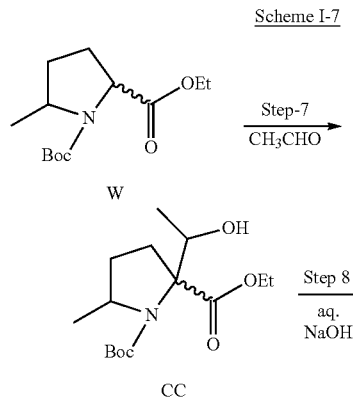

Synthesis of 1-tert-butyl 2-ethyl 2-(1-hydroxyethyl)-5-methylpyrrolidine-1,2-dicarboxylate (CC)

To a stirring solution of compound W (18.0 g, 70 mmol) in THF (200 mL) was added LiHMDS (84 mL, 84 mmol) drop wise at −20° C. and stirred for 30 min. To this acetaldehyde (4.2 mL, 77 mmol) was added drop wise and stirred for 45 min at −20° C. After consumption of the starting material (by TLC), the reaction was quenched with aqueous NH$_4$Cl solution (100 mL) and extracted with EtOAc (2×150 mL). The separated organic layer was dried over Na$_2$SO$_4$ and concentrated to afford crude material was purified by column chromatography eluting with 30% EtOAc/Hexane to afford compound CC (15 g, 71.4%) as colorless syrup.

$^1$H-NMR: (500 MHz, DMSO-d$_6$): δ 7.33-7.25 (m, 5H), 4.38 (d, J=10.5 Hz, 2H), 4.08-3.98 (m, 1H), 3.88 (d, J=9.5 Hz, 2H), 2.20-2.08 (m, 2H), 1.38 (s, 9H), 1.37-1.29 (m, 4H), 1.19 (t, J=7.5 Hz, 3H), 1.14-1.10 (m, 3H);

LCMS (m/z): 378 (M$^+$+1)

Synthesis of 1-(tert-butoxycarbonyl)-2-(1-hydroxyethyl)-5-methylpyrrolidine-2-carboxylic acid (DD)

To a stirring solution of compound CC (15 g, 49 mmol) in CH$_3$OH/THF (10 mL/40 mL) were added NaOH (3.98 g, 99 mmol) in water (10 mL) at RT. The reaction mixture was heated to 70° C. for 16 h. After consumption of the starting material (by TLC), the solvent from the reaction was evaporated under reduced pressure and acidified by using citric acid (pH ~4). The aqueous layer was extracted with EtOAc (2×200 mL). The combined organic layer was dried over Na$_2$SO$_4$ and concentrated to obtained crude compound, which was purified by column chromatography eluting 40% EtOAc to afford compound DD (4 g, 29.4%) as brown syrup.

$^1$H-NMR: (500 MHz, DMSO-d$_6$): δ 12.15 (br s, 2H), 4.54-4.50 (m, 1H), 4.03-4.02 (m, 1H), 2.17-1.77 (m, 3H), 1.41(s, 9H), 1.39-1.09 (m, 3H), 0.99-0.94 (m, 3H).

LCMS (m/z): 272.4 [M$^-$−1].

Scheme 1

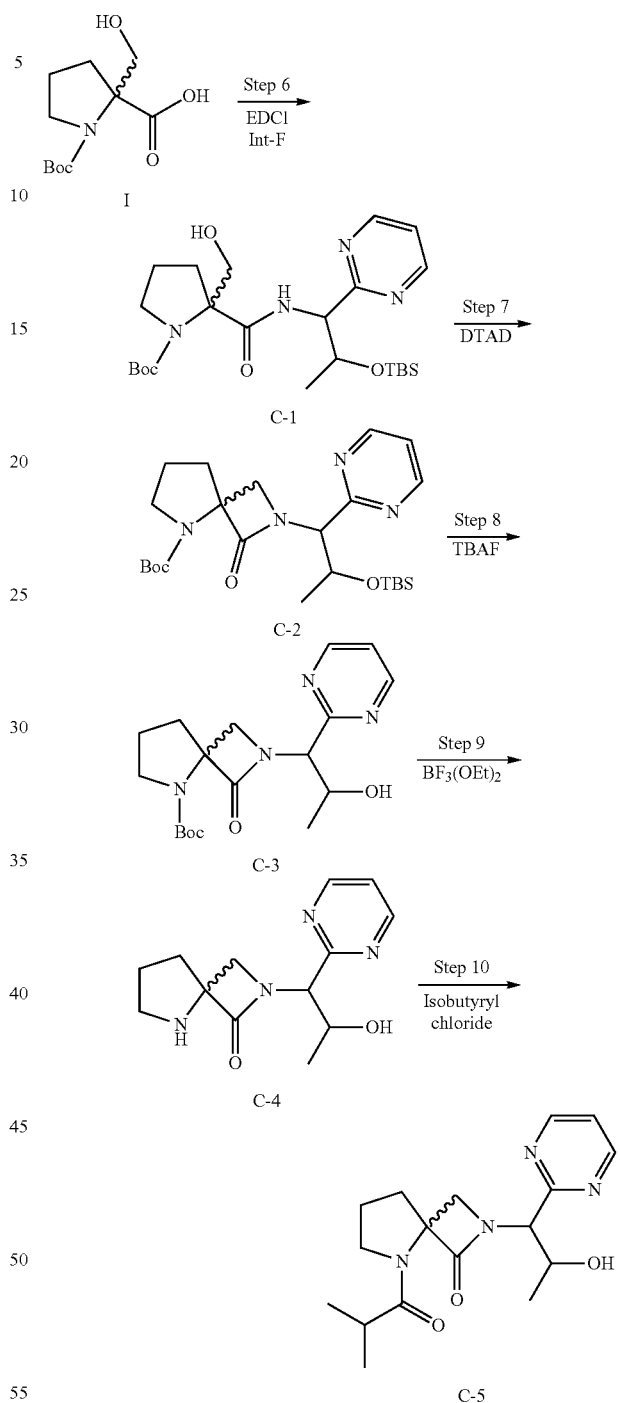

Synthesis of tert-butyl2-((2-((tert-butyldimethylsilyboxy)-1-(pyrimidin-2-ybpropyl)carbamoyl)-2-(hydroxymethyl)pyrrolidine-1-carboxylate(C-1)

Referring to Scheme 1, to a stirring solution of I (2 g, 8.16 mmol) in CH$_2$Cl$_2$ (60 mL) was added intermediate F (2.39 g, 8.97 mmol), EDCI.HCl (2.33 g, 12.2 mmol) followed by HOBt (1.66 g, 12.24 mmol) and DIPEA (4.5 mL, 24.4 mmol) at 0° C. The reaction mixture was warmed to RT and stirred for 16 h. After consumption of the starting material (by TLC), the reaction mixture was diluted with $CH_2Cl_2$. The separated organic layer was washed with aqueous $NaHCO_3$ solution followed by aqueous $NH_4Cl$. The organic layer was dried over anhydrous $Na_2SO_4$, filtered and concentrated under reduced pressure to get crude product, which was purified by silica gel column chromatography eluting with 70% EtOAc/hexane to afford compound C-1 (2.3 g, 57.5%).

$^1$H-NMR: (400 MHz, DMSO-$d_6$): δ 8.91 (d, 1H), 8.68 (d, 2H), 7.41 (br s, 1H), 5.74 (br t, 1H), 5.07-4.89 (m, 1H), 4.15-4.10 (m, 1H), 3.97-3.92 (m, 1H), 3.45-3.41 (m, 1H), 1.79-1.74 (m, 2H), 1.43-1.39 (m, 4H), 1.29-1.21 (m, 6H), 1.12 (d, 5H), 0.71 (s, 9H), 0.12 (t, 1H), 0.09 (s, 2H), 0.08 (s, 1H), 0.04 (s, 2H).

LCMS (m/z): 495.5 [M$^l$+1].

Synthesis of tert-butyl 2-(2-((tert-butyldimethylsilyboxy)-1-(pyrimidin-2-yl)propyl)-1-oxo-2,5-diazaspiro[3.4]octane-5-carboxylate(C-2)

To a stirring solution of compound C-1 (2.3 g, 4.65 mmol) in THF (23 mL) was added TPP (1.34 g, 5.12 mmol) followed by DTAD (1.6 g, 6.98 mmol) at 0° C. The reaction mixture was warmed to RT and stirred for 16 h. After consumption of the starting material (by TLC), the reaction mixture was concentrated under reduced pressure to get crude product, which was purified by silica gel column chromatography eluting with 25% EtOAc/hexane to afford compound C-2 (1.2 g, 54.2%).

$^1$H-NMR: (400 MHz, DMSO-$d_6$): δ 8.82 (d, 2H), 7.49 (t, 1H), 4.72 (d, 1H), 4.31 (q, 1H), 3.62 (br s, 2H), 3.25-3.19 (m, 1H), 2.24-2.05 (m, 2H), 1.85-1.81 (m, 2H), 1.42 (br s, 1H), 1.25 (t, 3H), 0.92 (s, 8H), 0.75 (s, 9H), 0.02 (s, 3H).

LCMS (m/z): 477.4 [M$^+$+1].

Synthesis of tert-butyl 2-(2-hydroxy-1-(pyrimidin-2-yl)propyl)-1-oxo-2,5 diazaspiro[3.4]octane-5-carboxylate (C-3)

To a stirring solution of compound C-2 (1.0 g, 2.10 mmol) in THF (20 mL) was added TBAF (1M in THF) (6.3 mL, 6.30 mmol) at 0° C. under $N_2$ atmosphere and stirred for 1 h. After consumption of the starting material (by TLC), the reaction mixture was quenched with ice water and extracted with EtOAc. The separated organic layer was dried over anhydrous $Na_2SO_4$, filtered and concentrated under reduced pressure to obtain crude product, which was purified by silica gel column chromatography eluting with 5% MeOH/$CH_2Cl_2$ to afford compound C-3 (0.35 g, 46%).

$^1$H-NMR: (400 MHz, DMSO-$d_6$): δ 8.81 (d, 2H), 7.49 (t, 1H), 4.81 (d, 1H), 4.65 (d, 1H), 4.25-4.20 (m, 1H), 3.64-3.51 (m, 2H), 3.34 (s, 1H), 3.25-3.20 (m, 1H), 2.25-2.20 (m, 2H), 1.87-1.82 (m, 2H), 1.19 (d, 3H), 0.97 (s, 9H).

LCMS (m/z): 363.3 [M$^+$+1].

Synthesis of tert-butyl 2-(2-hydroxy-1-(pyrimidin-2-yl)propyl)-1-oxo-2,5-diazaspiro[3.4]octane-5-carboxylate (C-4)

To a stirring solution of compound C-3 (200 mg, 0.42 mmol) in THF (5 mL) was added TBAF (1M in THF) (0.84 mL, 0.84 mmol) at 0° C. under $N_2$ atmosphere and stirred for 2 h. After consumption of the starting material (by TLC), the reaction mixture was concentrated under reduced pressure to obtain crude product, which was purified by silica gel column chromatography eluting with 2% MeOH/$CH_2Cl_2$ to afford C-4 (125 mg, 82.2%).

$^1$H-NMR: (400 MHz, CD$_3$OD): 8.78 (t, J=3.2 Hz, 2H), 7.42-7.38 (m, 1H), 4.92-4.87 (m, 1H), 4.79-4.56 (m, 1H), 4.43-4.38 (m, 1H), 4.33-3.97 (m, 1H), 3.88-3.80 (m, 1H), 3.48-3.44 (m, 1H), 3.40-3.30 (m, 1H), 2.31-2.12 (m, 2H), 1.96-1.84 (m, 2H), 1.42 (s, 9H), 1.32-1.28 (m, 3H);

LCMS (m/z): 363.3 [M$^+$+1].
HPLC: 94.5%.

Synthesis of 2-(2-hydroxy-1-(pyrimidin-2-yl)propyl)-2,5-diazaspiro[3.4]octan-1-one (C-5)

To a stirring solution of compound C-4 (0.3 g, 0.82 mmol) in $CH_2Cl_2$ (6 mL) was added molecular sieves (0.3 g) followed by BF$_3$-etherate (0.31 mL, 2.48 mmol) at 0° C. and stirred at RT for 1 h. After consumption of the starting material (by TLC), the reaction mixture was filtered and obtained residue was dissolved in MeOH and washed with $CH_2Cl_2$. The volatiles were evaporated under reduced pressure to obtain crude product, which was purified by silica gel column chromatography eluting with 8% MeOH/$CH_2Cl_2$ to afford C-5 (0.12 g, 55%).

$^1$H-NMR: (400 MHz, DMSO-$d_6$): δ 8.81 (d, 2H), 7.49 (t, 1H), 4.81 (d, 1H), 4.65 (d, 1H), 4.25-4.20 (m, 1H), 3.64-3.51 (m, 2H), 3.12-3.01 (m, 2H), 2.15-2.10 (m, 2H), 1.87-1.82 (m, 2H), 1.19 (d, 3H).

LCMS (m/z): 263.1 [M$^+$+1].

Synthesis of 2-(2-hydroxy-1-(pyrimidin-2-yl)propyl)-5-isobutyryl-2, 5-diazaspiro[3.4]octan-1-one (C-6)

To a stirring solution of compound C-5 (500 mg, 1.9 mmol) in DCM (10 mL) was added TEA (0.79 mL, 5.72 mmol) followed by isobutyryl chloride (241 mg, 2.28 mmol) at 0° C. under $N_2$ atmosphere and stirred for 2 h at RT. After consumption of the starting material (by TLC), the reaction mixture was diluted with water (10 mL) and extracted with $CH_2Cl_2$ (2×15 mL). The combined organic layer was washed with citric acid solution (1×20 mL). The separated organic layer was dried over anhydrous $Na_2SO_4$, filtered and concentrated under reduced pressure. Obtained crude material was purified by silica gel column chromatography eluting 2% MeOH/DCM to afford C-6 (85 mg, 13.4%) as white solid.

$^1$H-NMR: (400 MHz, CD$_3$OD): δ 4.91-4.75 (m, 1H), 4.46-4.40 (m, 1H), 3.99-3.85 (m, 1H), 3.70-3.64 (m, 1H), 3.60-3.45 (m, 3H), 2.80-2.69 (m, 1H), 2.29-2.22 (m, 2H), 2.07-1.96 (m, 2H), 1.45-1.33 (m, 3H), 1.16-1.10 (m, 3H), 1.06-1.01 (m, 3H).

Scheme 2

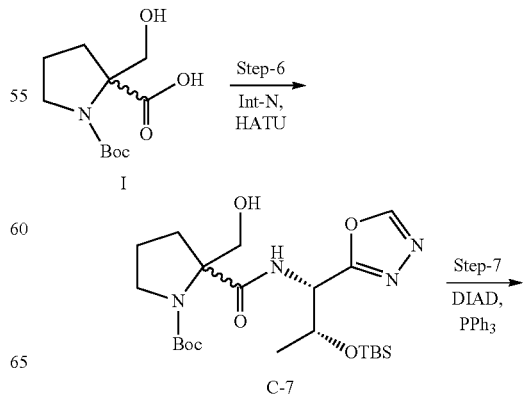

Synthesis of tert-butyl 2-(((1R, 2S)-2-((tert-butyldimethylsilyl)oxy)-1-(1,3,4-oxadiazol-2-yl)propyl)carbamoyl)-2-(hydroxymethyl)pyrrolidine-1-carboxylate (C-8)

To a stirring solution of triphenylphosphine (4.05 g, 15.4 mmol) in THF (30 mL) was added DIAD (3.03 g, 15.4 mmol) at RT and stirred for 15 min. After added compound C-7 (3 g, 6.19 mmol) in (20 mL) THF slowly and reaction mixture was stirred at RT for 3 h. After consumption of the starting material (by TLC), the reaction was concentrated under reduced pressure. The crude material was triturated with 30% Ether/n-hexane (2×50 mL). The filtered organic solvent was concentrated and crude residue was purified by column chromatography by eluting 30% EtOAc/n-hexane to afford compound C-8 (2 g, 69.4%) as thick syrup.

$^1$H-NMR: (400 MHz, DMSO-$d_6$): δ 9.28 (s, 1H), 5.30-5.21 (m, 1H), 4.84-4.81 (m, 1H), 4.49-4.29 (m, 1H), 4.05-3.91 (m, 1H), 3.65-3.61 (m, 1H), 3.39-3.24 (m, 1H), 2.23-2.12 (m, 2H), 1.81-1.76 (m, 2H), 1.41 (s, 9H), 1.20-1.14 (m, 3H), 0.75 (s, 9H), −0.22 (s, 6H);

Mass (ESI): m/z 467.6 [M$^+$+1]

Synthesis of tert-butyl 2-((1R, 2S)-2-hydroxy-1-(1,3,4-oxadiazol-2-yl)propyl)-1-oxo-2,5-diazaspiro[3.4]octane-5-carboxylate (C-9)

To a stirring solution of compound C-8 (2 g, 4.29 mmol) in THF (20 mL) was added TBAF (4.3 mL, 6.43 mmol) slowly at 0° C. and stirred at RT for 30 min. After completion of reaction (by TLC), the reaction mixture was evaporated under reduced pressure. The crude residue was purified by column chromatography by eluting 70% EtOAc/n-hexane to afford C-9 (400 mg, 26.5%) as white solid.

$^1$H-NMR: (400 MHz, DMSO-$d_6$): 9.29 (s, 1H), 5.30-5.21 (m, 1H), 5.08-4.95 (m, 1H), 4.08-4.03 (m, 1H), 3.91-3.71 (m, 1H), 3.75-3.71 (m, 1H), 3.65-3.52 (m, 1H), 3.36-3.22 (m, 1H), 2.22-2.09 (m, 2H), 1.83-1.77 (m, 2H), 1.41 (s, 9H), 1.10-1.04 (m, 3H);

LCMS: 353.4;
HPLC: 99.82%.

Synthesis of 2-((1R, 2S)-2-hydroxy-1-(1,3,4-oxadiazol-2-yl)propyl)-2,5-diazaspiro[3.4]octan-1-one (C-10)

To a stirring solution of compound C-9 (500 mg, 1.07 mmol) in DCM (5 mL) was added BF$_3$(OEt)$_2$ (0.26 mL, 2.14 mmol) slowly at 0° C. and stirred at RT for 30 min. After completion of reaction (by TLC), the reaction mixture was evaporated under reduced pressure. The crude residue was triturated with di ethylether/n-pentane (5 mL/5 mL) to obtain solid, C-10, which was taken into the next step without further purification.

Synthesis of 2-((1R, 2S)-2-hydroxy-1-(1,3,4-oxadiazol-2-yl)propyl)-5-isobutyryl-2,5-diazaspiro[3,4]octan-1-one (C-11)

To a stirring solution of compound C-10 (700 mg, 2.77 mmol) in DCM (10 mL) was added TEA (0.94 mL, 6.92 mmol), SM-3 (440 mg, 4.15 mmol) at 0° C. and stirred to RT for 1 h. After completion of reaction (by TLC), diluted with water (20 mL). The organic layer was washed with brine solution (1×50 mL). The organic layer was dried over anhydrous Na$_2$SO$_4$, filtered and concentrated under reduced pressure. The crude residue was purified by column chro-

Synthesis of tert-butyl 2-(((1R, 2S)-2-((tert-butyldimethylsilyl)oxy)-1-(1,3,4-oxadiazol-2-yl)propyl)carbamoyl)-2-(hydroxymethyl)pyrrolidine-1-carboxylate (C-7)

To a stirring solution of compound I (2.1 g, 8.57 mmol) in CH$_2$Cl$_2$ (20 mL) were added DIPEA (3.81 mL, 21.4 mmol), intermediate F (2.64 g, 10.28 mmol), HATU (3.90 g, 10.28 mmol) at 0° C. and stirred to RT for 16 h. After consumption of the starting material (by TLC), the reaction mixture was diluted with water (30 mL). The organic layer was washed with citric acid (1×50 mL) followed by brine solution (1×50 mL). The organic layer was dried over anhydrous Na$_2$SO$_4$, filtered and concentrated under reduced pressure. Obtained crude material was purified by silica gel column chromatography eluting with 50% EtOAc/n-hexane to afford compound C-7 (3.5 g, 85.15%) as yellow thick syrup.

$^1$H-NMR: (400 MHz, DMSO-$d_6$): δ 9.24 (s, 1H), 8.17 (d, J=8.4 Hz, 1H), 5.82-5.54 (m, 1H), 4.36-4.28 (m, 1H), 4.12-4.00 (m, 1H), 3.93-3.66 (m, 1H), 3.43-3.39 (m, 1H), 2.69-2.66 (m, 2H), 2.02-1.94 (m, 2H), 1.78-1.68 (m, 2H), 1.40 (s, 9H), 1.23-1.15 (m, 3H), 0.75 (s, 9H), −0.08 (s, 6H);

Mass (ESI): m/z 484.7 [M$^+$+1]

matography followed by preparative HPLC purification to afford C-11 (150 mg, 16.8%) as white solid.

¹H-NMR: (400 MHz, DMSO-d₆): 9.26 (s, 1H), 5.24-5.04 (m, 1H), 5.03-4.93 (m, 1H), 4.27-3.91 (m, 1H), 3.90-3.64 (m, 1H), 3.49-3.45 (m, 3H), 2.73-2.61 (m, 1H), 2.17-2.14 (m, 2H), 2.10-2.06 (m, 2H), 1.25-1.07 (m, 3H), 0.95-0.93 (m, 6H).

LCMS m/z: 323.3.
HPLC: 97.89%.

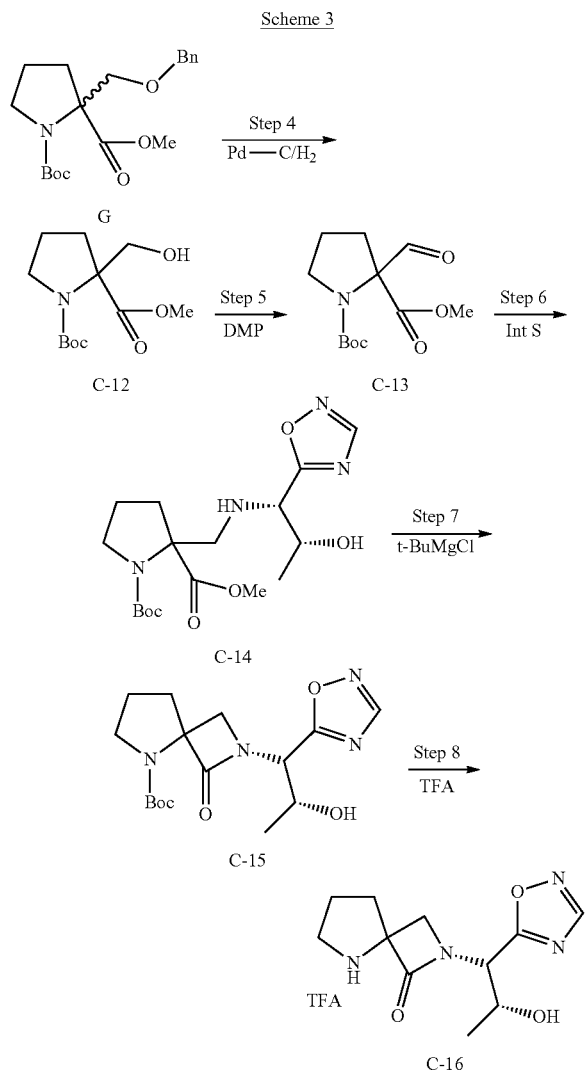

Synthesis of 1-tert-butyl 2-methyl 2-(hydroxymethyl)pyrrolidine-1,2-dicarboxylate(C-12)

To a stirring solution of compound G (74 g, 0.21 mol) in methanol (740 mL) was added 10% Pd/C (50% wet, 14.8 g) under N₂ atmosphere and stirred for 6 h under H₂ atmosphere (balloon pressure). The reaction mixture was filtered through celite pad and concentrated under reduced pressure to afford compound C-12 (45 g, 82%) as crude.

Synthesis of 1-tert-butyl 2-methyl 2-formylpyrrolidine-1,2-dicarboxylate(C-13)

To a stirring solution of compound C-12 (10 g, 38.5 mmol) in CH₂Cl₂ (100 mL) was added Dess-Martin periodinane (19.6 g, 46.27 mmol) at 0° C. under N₂ atmosphere and stirred for 3 h. After consumption of the starting material (by TLC), the reaction was quenched with aqueous NaHCO₃ solution and extracted with CH₂Cl₂ (2×100 mL). The organic layer was dried over anhydrous Na₂SO₄ and concentrated under vacuum. The crude was purified by column chromatography eluting with 10% EtOAc/Hexane to afford compound C-13 (7 g, 70.5%).

Synthesis of 1-tert-butyl 2-methyl 2-((((1S,2R)-2-hydroxy-1-(1,2,4-oxadiazol-5-yl)propyl)amino)methyl)pyrrolidine-1,2-dicarboxylate (C-14)

To a stirring solution of compound C-13 (3 g, 11.6 mmol) in MeOH (30 mL) was added sodium acetate (1.91 g, 23.3 mmol) followed by intermediate S (3.6 g, 13.9 mmol). The reaction mixture was heated to reflux for 1 h. The reaction mixture was slowly cooled to RT-0° C., to this sodium cyanoborohydride (1.465 g, 23.3 mmol) and stirring was continued for another 6 h at RT. After consumption of the starting material (by TCL), methanol from the reaction was evaporated under reduced pressure and the residue was diluted with water and extracted with EtOAc (2×50 mL). The separated organic layer was dried over anhydrous Na₂SO₄ and concentrated under reduced pressure to give crude; which was purified by silica gel column chromatography eluting with 40% EtOAc/Hexane to afford compound C-14 (2.5 g, 56%).

LCMS m/z: 385 [M⁺+1].

Synthesis of tert-butyl 2-((1S,2R)-2-hydroxy-1-(1,2,4-oxadiazol-5-yl)propyl)-1-oxo-2,5-diazaspiro[3,4]octane-5-carboxylate (C-15)

To a stirring solution of compound C-14 (1.5 g, 3.90 mmol) in THF (30 mL) was cooled to 0° C. and added t-BuMgCl (1M in THF, 15.6 mL, 15.6 mmol) and stirred for 15 min. After consumption of the starting material (by TLC), the reaction mixture was quenched with aqueous NH₄Cl solution and diluted with water. Aqueous layer was extracted with EtOAc (2×25 mL). The separated organic layer was dried over anhydrous Na₂SO₄ and concentrated under reduced pressure. Obtained crude material was purified by silica gel column chromatography eluting with 150% EtOAc/CH₂Cl₂ to afford C-15 (0.15 g, 11%).

¹H-NMR: (400 MHz, DMSO-d6): δ 9.02 (s, 1H), 5.15 (s, 1H), 4.37-4.32 (m, 1H), 3.95 (d, 1H), 3.66-3.60 (m, 1H), 3.36-3.30 (m, 1H), 2.29-2.09 (m, 2H), 1.87-1.82 (m, 2H), 1.55 (s, 9H), 1.27 (d, 3H).

LCMS (ESI) m/z: 351 [M⁺−1].
HPLC Purity: 96%.

Synthesis of 2-((1S,2R)-2-hydroxy-1-(1,2,4-oxadiazol-5-yl)propyl)-2,5-diazaspiro[3,4]octan-1-one (C-16)

To a stirring solution of C-15 (0.4 g, 1.13 mmol) in CH₂Cl₂ (4 mL) was added TFA (0.43 mL) at 0° C. and stirred at RT for 30 min. The reaction mixture was concentrated under vacuum. Obtained crude material was purified by prep-HPLC to afford C-16 (65 mg) as TFA salt.

¹H-NMR: (400 MHz, DMSO-d6): δ 9.89 (br s, 1H), 9.08 (s, 1H), 5.46 (d, 1H), 5.31 (s, 1H), 4.37-4.35 (m, 1H), 3.99 (d, 1H), 3.81 (d, 1H), 3.42-3.35 (m, 2H), 2.35-2.18 (m, 2H), 2.10-2.03 (m, 2H), 1.24 (d, 3H).

LCMS (ESI) m/z: 253.4 [M⁺+1].
HPLC Purity: 95%.

Scheme 4

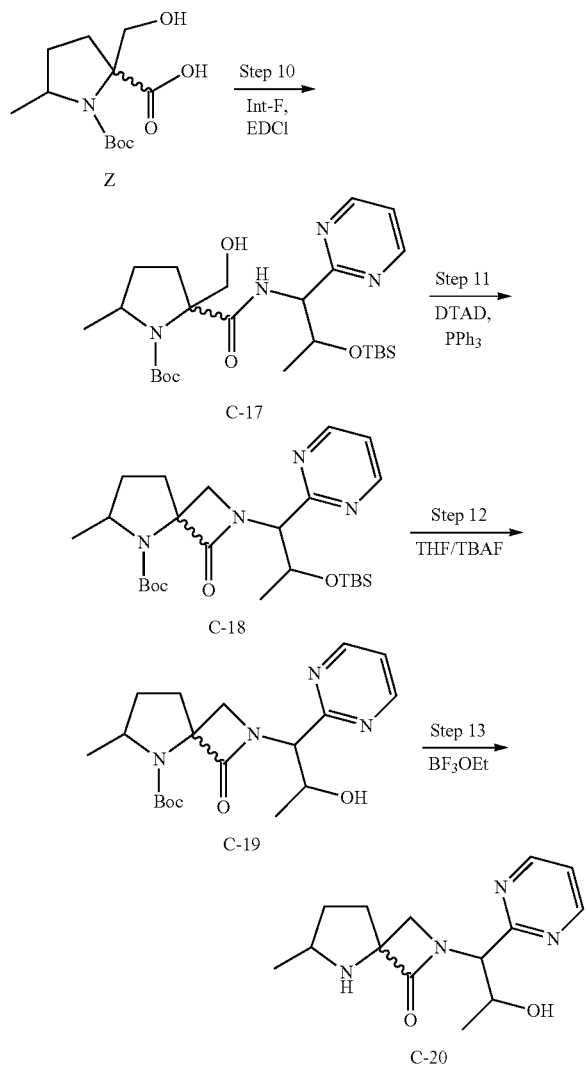

Synthesis of tert-butyl 2-((2-((tert-butyldimethylsilyl)oxy)-1-(pyrimidin-2-yl)propyl)carbamoyl)-2-(hydroxymethyl)-5-methylpyrrolidine-1-carboxylate (C-17)

To a stirring solution of compound Z (500 mg, 1.93 mmol) in DCM (10 mL) were added N,N-diisopropylethylamine (1.0 mL, 5.79 mmol), intermediate F (566 mg, 2.12 mmol), followed by EDCI (737 mg, 3.86 mmol), HOBT (521 mg, 3.86 mmol) at 0° C. and stirred at RT for 16 h. After consumption of the starting material (by TLC), the reaction mixture was diluted with water (20 mL). The separated organic layer was washed with saturated brine solution (1×30 mL). The separated organic layer was dried over anhydrous $Na_2SO_4$ and concentrated under reduced pressure to afford crude compound which was purified by column chromatography to obtained compound C-17 (300 mg, 30.6%) as pale yellow liquid.

$^1$H-NMR: (500 MHz, $CDCl_3$): δ 8.73-8.68 (m, 3H), 5.30 (s, 2H), 4.40-4.15 (m, 1H), 3.76-3.61 (m, 1H), 3.18-3.13 (m, 1H), 2.18-2.13 (m, 4H), 1.46 (s, 9H), 1.32 (d, J=5.5 Hz, 3H), 1.24 (d, J=6.5 Hz, 3H), 1.08 (d, J=6.5 Hz, 1H), 0.79 (s, 9H), 0.74 (t, J=10.5 Hz, 1H), 0.12 (s, 6H)

Synthesis of tert-butyl 2-(2-((tert-butyldimethylsilyl)oxy)-1-(pyrimidin-2-yl)propyl)-6-methyl-1-oxo-2,5-diazaspiro[3,4]octane-5-carboxylate (C-18)

To a stirring solution of triphenylphosphine (380 mg, 1.47 mmol) in dry THF (10 mL) was added DTAD (339 mg, 1.47 mmol) at RT and stirred for 10 min. After added compound C-17 (300 mg, 0.59 mmol) and the reaction mixture was stirred at RT for 16 h. After consumption of the starting material (by TLC), the reaction mixture was concentrated under reduced pressure. The crude material was purified by silica gel column chromatography eluting 30% EtOAc/hexane to afford compound C-18 (80 mg, 27.5%) as yellow liquid.

$^1$H-NMR: (400 MHz, $CDCl_3$): δ 7.73-7.64 (m, 3H), 5.26 (s, 2H), 4.30 (dd, J=4.4 Hz, 4.4 Hz, 1H), 4.17-4.12 (m, 1H), 2.76 (t, J=6.8 Hz, 1H), 2.32-2.28 (m, 2H), 2.05-2.00 (m, 2H), 1.49 (s, 9H), 1.45 (d, J=5.2 Hz, 3H), 1.42 (d, J=4.8 Hz, 3H), 0.89 (s, 9H), 0.15 (s, 6H).

Synthesis of tert-butyl 2-(2-hydroxy-1-(pyrimidin-2-yl)propyl)-6-methyl-1-oxo-2,5-diazaspiro[3,4]octane-5-carboxylate (C-19)

To a stirring solution of compound C-18 (700 mg, 1.42 mmol) in dry THF (10 mL) was added TBAF (744 mg, 2.85 mmol) at 0° C. The reaction mixture was stirred at RT for 3 h. After consumption of the starting material (by TLC), the reaction mixture was concentrated under reduced pressure. The crude material was purified by silica gel column chromatography eluting 80% EtOAc/hexane to afford C-19 (0.16 g, 30%) as yellow thick syrup.

$^1$H-NMR: (500 MHz, DMSO-$d_6$): δ 8.77 (d, J=5.0 Hz, 2H), 7.42 (t, J=4.5 Hz, 1H), 4.76-4.63 (m, 2H), 4.14-4.11 (m, 1H), 3.85-3.83 (m, 1H), 3.54-3.34 (m, 1H), 2.25-2.21 (m, 2H), 2.08-1.93 (m, 1H), 1.53-1.47 (m, 1H), 1.39 (s, 9H), 1.15 (d, J=6.0 Hz, 3H), 1.03-0.80 (m, 4H).

LCMS (ESI): 377.4 [M$^+$+1].

HPLC: 94.6% (both isomers).

Synthesis of 2-(2-hydroxy-1-(pyrimidin-2-yl)propyl)-6-methyl-2,5-diazaspiro[3,4]octan-1-one (C-20)

To a stirring solution of compound C-19 (260 mg, 0.69 mmol) in DCM (10 mL) was added 4A molecular sieves (70 mg), $BF_3OEt_2$ (0.08 mL) at 0° C. under $N_2$ atmosphere. The reaction mixture was stirred at RT for 30 min. After consumption of the starting material (by TLC), the reaction mixture was concentrated under reduced pressure to afford crude, which was purified by preparative HPLC method to afford C-20 (65 mg, 34%) as white solid.

$^1$H-NMR: (400 MHz, $D_2O$): δ 8.88-8.86 (m, 2H), 7.63-7.57 (m, 1H), 4.92-4.89 (m, 1H), 4.61-4.56 (m, 1H), 4.03-3.91 (m, 3H), 2.61-2.41 (m, 3H), 1.92-1.84 (m, 1H), 1.46 (d, J=6.8 Hz, 3H), 1.37 (d, J=4.8 Hz, 3H);

LCMS (ESI): 295.3 [M$^+$+$H_2O$].

HPLC: 91.2% (both enantiomers).

Scheme 5

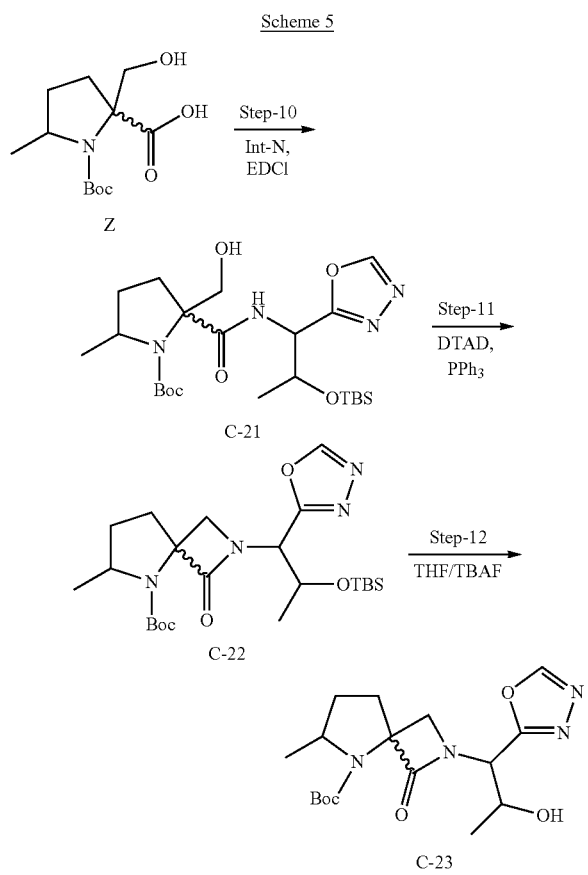

Synthesis of tert-butyl 2-((2-((tert-butyldimethylsilyl)oxy)-1-(1,3,4-oxadiazol-2-yl)propyl)carbamoyl)-2-(hydroxymethyl)-5-methylpyrrolidine-1-carboxylate (C-21)

To a stirring solution of compound Z (4 g, 15.4 mmol) in DCM (30 mL) were added N,N-diisopropylethylamine (8 mL, 46.33 mmol), intermediate N (4.74 g, 18.48 mmol) followed by HATU (7 g, 18.48 mmol) at 0° C. and stirred at RT for 12 h. After consumption of the starting material (by TLC), the reaction mixture was diluted with water (20 mL). The separated organic layer was washed with 10% citric acid solution (1×50 mL) followed by saturated brine solution (1×50 mL). The separated organic layer was dried over anhydrous $Na_2SO_4$ and concentrated under reduced pressure to afford crude compound which was purified by column chromatography eluting 30% EtOAc/n-hexane to obtained compound C-21 (5.5 g, 71.8%) as pale yellow liquid.

$^1$H-NMR: (500 MHz, DMSO-$d_6$): δ 9.25 (s, 1H), 5.50-5.41 (m, 1H), 5.19-5.06 (m, 2H), 4.38-4.36 (m, 1H), 4.05-3.90 (m, 3H), 2.69-1.98 (m, 2H), 1.39 (s, 9H), 1.37-1.26 (m, 2H), 1.23-1.16 (m, 6H), 0.76 (s, 9H), −0.01 (s, 6H).

Synthesis of tert-butyl 2-(2-((tert-butyldimethylsilyboxy)-1-(1,3,4-oxadiazol-2-yl)propyl)-6-methyl-1-oxo-2,5-diazaspiro[3,4]octane-5-carboxylate (C-22)

To a stirring solution of triphenylphosphine (5.5 g, 11.04 mmol) in THF (55 mL) was added DTAD (5.07 g, 22.05 mmol) at RT and stirred for 10 min. After added compound C-21 (5.5 g, 11.04 mmol) and the reaction mixture was stirred at RT for 16 h. After consumption of the starting material (by TLC), the reaction mixture was concentrated under reduced pressure. The crude material was purified by silica gel column chromatography eluting 30% EtOAc/hexane to afford compound C-22 (4 g, 75.4%) as yellow liquid.

$^1$H-NMR: (400 MHz, DMSO-$d_6$): δ 9.36 (s, 1H), 5.30-4.48 (m, 1H), 4.47-4.31 (m, 1H), 4.03-3.88 (m, 2H), 3.62-3.58 (m, 1H), 2.38-1.98 (m, 3H), 1.57-1.53 (m, 1H), 1.41 (s, 9H), 1.38-1.15 (m, 6H), 0.69 (s, 9H), −0.01 (s, 6H).

Synthesis tert-butyl 2-(2-hydroxy-1-(1,3,4-oxadiazol-2-yl)propyl)-6-methyl-1-oxo-2,5-diazaspiro[3,4]octane-5-carboxylate (C-23)

To a stirring solution of compound C-22 (3.5 g, 7.29 mmol) in THF (35 mL) was added TBAF (1M THF) (14.5 mL, 14.58 mmol) at 0° C. The reaction mixture was stirred at RT for 1 h. After consumption of the starting material (by TLC), the reaction mixture was concentrated under reduced pressure. The crude material was purified by silica gel column chromatography eluting 60% EtOAc/hexane to afford C-23 (800 mg, 30.7%) as an off-white solid.

$^1$H-NMR: (400 MHz, DMSO-$d_6$): δ 9.30 (s, 1H), 5.30-5.21 (m, 1H), 5.13-5.02 (m, 1H), 4.13-4.03 (m, 1H), 3.90-3.83 (m, 1H), 3.74-3.68 (m, 1H), 3.62-3.49 (m, 1H), 2.29 (m, 3H), 1.56-1.52 (m, 1H), 1.40 (s, 9H), 1.25-1.14 (m, 6H).

LCMS (ESI) (m/z): 377.4 [M$^+$+1].

HPLC: 95.38%.

Scheme 6

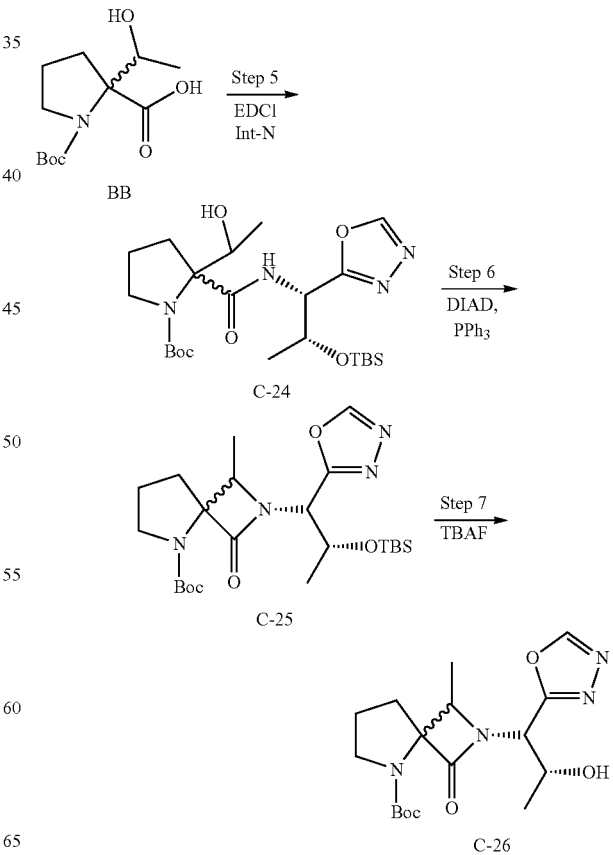

Synthesis of tort-butyl 2-(((1R, 2S)-2-((tert-butyldimethylsilyl)oxy)-1-(1,3,4-oxadiazol-2-yl)propyl)carbamoyl)-2-(1-hydroxyethyl)pyrrolidine-1-carboxylate (C-24)

To a stirring solution of compound BB (3 g, 11.5 mmol) in CH$_2$Cl$_2$ (30 mL) were added DIPEA (6 mL, 34.5 mmol), intermediate N (2.95 g, 11.5 mmol), HATU (5.24 g, 13.8 mmol) at 0° C. and stirred to RT for 12 h. After consumption of the starting material (by TLC), the reaction mixture was diluted with water (30 mL) and extracted with CH$_2$Cl$_2$ (50 mL). The combined organic layer was washed with citric acid (1×50 mL) followed by brine solution (1×50 mL). The organic layer was dried over anhydrous Na$_2$SO$_4$, filtered and concentrated under reduced pressure. Obtained crude material was purified by silica gel column chromatography eluting with 35% EtOAc/n-hexane to afford compound C-24 (3.6 g, 62.5%) as yellow thick syrup.

$^1$H-NMR: (500 MHz, DMSO-d$_6$): δ 9.26 (s, 1H), 8.74 (d, J=8.5 Hz, 2H), 5.30-5.12 (m, 1H), 4.61-4.58 (m, 1H), 4.38-4.35 (m, 2H), 3.57-3.54 (m, 1H), 2.68-1.98 (m, 2H), 1.97-1.69 (m, 2H), 1.40 (s, 9H), 1.19-1.00 (m, 6H), 0.85 (s, 6H), −0.25 (s, 9H).

Mass (ESI): m/z 497.6 [M$^-$−1].

Synthesis of tert-butyl 2-((1R, 2S)-2-((tert-butyldimethylsilyl)oxy)-1-(1,3,4-oxadiazol-2-yl)propyl)-1-methyl-3-oxo-2,5-diazaspiro[3,4]octane-5-carboxylate (C-25)

To a stirring solution of triphenylphosphine (3.6 g, 14.05 mmol) in THF (20 mL) was added DIAD (2.8 g, 14.05 mmol) at RT and stirred for 30 min. After added compound C-24 (3.5 g, 7.02 mmol) in (15 mL) THF slowly and reaction mixture was stirred at RT for 6 h. After consumption of the starting material (by TLC), the reaction was concentrated under reduced pressure. The crude material was purified by column chromatography by eluting 30% EtOAc/n-hexane to afford compound C-25 (3 g, 89.2%) as thick syrup.

$^1$H-NMR: (400 MHz, DMSO-d$_6$): δ 9.33 (s, 1H), 5.33-5.29 (m, 2H), 4.79-4.75 (m, 1H), 4.50-4.45 (m, 1H), 4.06-3.96 (m, 1H), 2.16-2.08 (m, 1H), 2.01-1.89 (m, 1H), 1.81-1.76 (m, 2H), 1.40 (s, 9H), 1.24-1.15 (s, 6H), 0.80 (s, 9H), −0.08 (s, 6H).

Mass (ESI): m/z 319.3 [M$^+$+1].

Synthesis of tert-butyl 2-((1R, 2S)-2-hydroxy-1-(1,3,4-oxadiazol-2-yl)propyl)-1-methyl-3-oxo-2,5-diazaspiro[3,4]octane-5-carboxylate (C-26)

To a stirring solution of compound C-25 (3 g, 6.25 mmol) in THF (25 mL) was added TBAF (12.5 mL, 12.5 mmol) at 0° C. and stirred for 30 min. After consumption of the starting material (by TLC), the reaction mixture was concentrated under reduced pressure. Obtained crude material was purified by silica gel column chromatography eluting with 60% EtOAc/n-hexane to afford C-26 (0.8 g, 35%) as white solid.

$^1$H-NMR: (400 MHz, DMSO-d$_6$): δ 9.29 (s, 1H), 5.28-5.15 (m, 1H), 5.08-4.89 (m, 1H), 4.43-4.35 (m, 1H), 3.97-3.79 (m, 1H), 3.65-3.40 (m, 1H), 3.31-3.25 (m, 1H), 2.15-2.00 (m, 2H), 1.93-1.86 (m, 1H), 1.80-1.68 (m, 1H), 1.40 (s, 9H), 1.18-1.04 (m, 6H).

Mass (ESI): m/z 367.4 [M$^+$+1].

HPLC: 95.85% (both isomers).

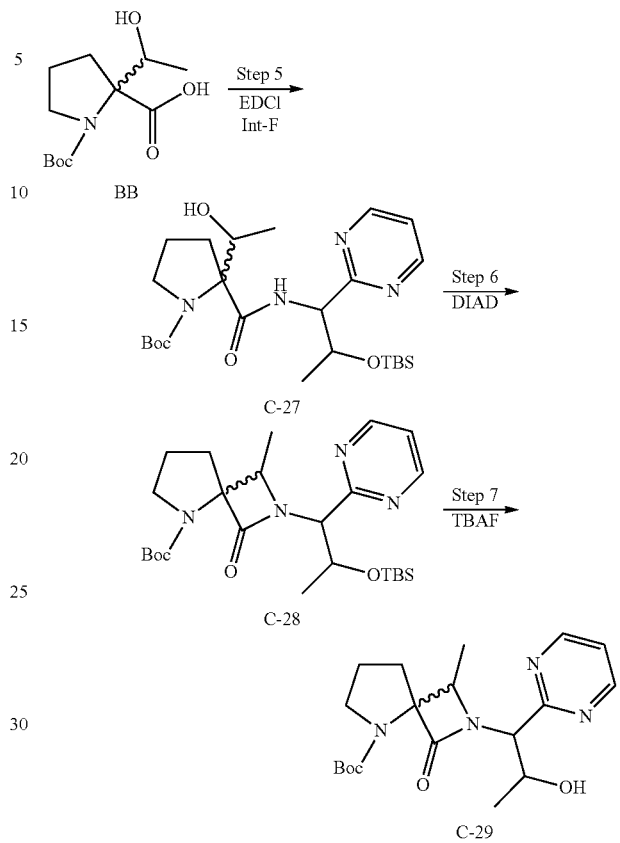

Scheme 7

Synthesis of tert-butyl 2((2-((tert-butyldimethylsilyl)oxy)-1-(pyrimidin-2-yl)propyl)carbamoyl)-2-(1-hydroxyethyl)pyrrolidine-1-carboxylate (C-27)

To a stirring solution of compound BB (200 mg, 0.77 mmol) in CH$_2$Cl$_2$ (20 mL) were added DIPEA (298 mg, 2.31 mmol), EDCI (221 mg, 1.15 mmol), HOBt (177 mg, 1.15 mmol) followed by intermediate F (206 mg, 0.77 mmol) at 0° C. and stirred for 16 h at RT. After consumption of the starting material (by TLC), the reaction mixture was concentrated under reduced pressure. Obtained crude material was purified by silica gel column chromatography eluting with 4% MeOH/DCM to afford compound C-27 (210 mg, 53.6%) as pale yellow thick syrup.

$^1$H-NMR: (500 MHz, DMSO-d$_6$): δ 8.77 (d, J=4.5 Hz, 2H), 7.40 (t, J=5.0 Hz, 1H), 4.95-4.92 (m, 2H), 4.21-4.05 (m, 2H), 3.34-3.25 (m, 2H), 3.20-3.12 (m, 1H), 1.81-1.63 (m, 4H), 1.48 (s, 9H), 1.12-1.06 (m, 3H), 0.99-0.85 (m, 3H), 0.70 (s, 9H), −0.06 (s, 6H);

LCMS (m/z): 509.4 [M$^+$+1]

Synthesis of tert-butyl 2-(2-((tert-butyldimethylsilyl)oxy)-1-(pyrimidin-2-yl)propyl)-1-methyl-3-oxo-2,5-diazaspiro[3,4]octane-5-carboxylate (C-28)

To a stirring solution of triphenylphosphine (206 mg, 0.78 mmol) in THF (6 mL) was added DIAD (179 mg, 0.78 mmol) at RT and stirred for 30 min. To this added compound C-27 (200 mg, 0.39 mmol) in (5 mL) THF slowly and reaction mixture was stirred at RT for 2 h. After consumption of the starting material (by TLC), the reaction was concentrated under reduced pressure. The crude material was triturated with diethylether/n-oentane (10 mL/10 mL). The filtered solvent was concentrated and purified by silica gel column chromatography eluting 30% EtOAc/n-hexane to afford compound C-28 (80 mg, 41.8%) as pale yellow liquid.

$^1$H-NMR: (400 MHz, DMSO-d$_6$): δ 8.81-8.77 (m, 2H), 7.72 (d, J=5.5 Hz, 1H), 4.92-4.80 (m, 1H), 4.70-4.65 (m, 2H), 4.46-4.20 (m, 1H), 3.30-3.16 (m, 1H), 1.86-1.65 (m, 2H), 1.64-1.43 (m, 2H), 1.40 (s, 9H), 1.20-1.01 (m, 3H), 0.92-0.85 (m, 3H), 0.74 (s, 9H), −0.06 (s, 6H);

LCMS (m/z): 491.4 [M$^1$+1].

Synthesis of tert-butyl 2-(2-hydroxy-1-(pyrimidin-2-yl)propyl)-1-methyl-3-oxo-2,5-diazaspiro[3,4]octane-5-carboxylate (C-29)

To a stirring solution of compound C-28 (450 mg, 0.91 mmol) in THF (10 mL) was added TBAF (1.8 mL, 1.83 mmol) in 5 mL THF at 0° C. and stirred to RT for 4 h. After consumption of the starting material (by TLC), the reaction was concentrated under reduced pressure. The crude material was purified by silica gel column chromatography eluting 2% MeOH/DCM followed by preparative HPLC purification to afford C-29 (100 mg, 29%) as a semi solid.

$^1$H-NMR: (400 MHz, CD$_3$OD): δ 8.82-8.79 (m, 2H), 8.78-7.43 (m, 1H), 4.94-4.89 (m, 1H), 4.63-4.44 (m, 1H), 3.99-3.73 (m, 1H), 3.56-3.36 (m, 2H), 2.29-2.22 (m, 2H), 1.99-1.73 (m, 2H), 1.40 (s, 9H), 1.24-1.20 (m, 3H), 1.13-1.05 (m, 3H).

LCMS(m/s): 377.5 [M$^+$+1].

HPLC: 94.4% (both isomers).

Scheme 9

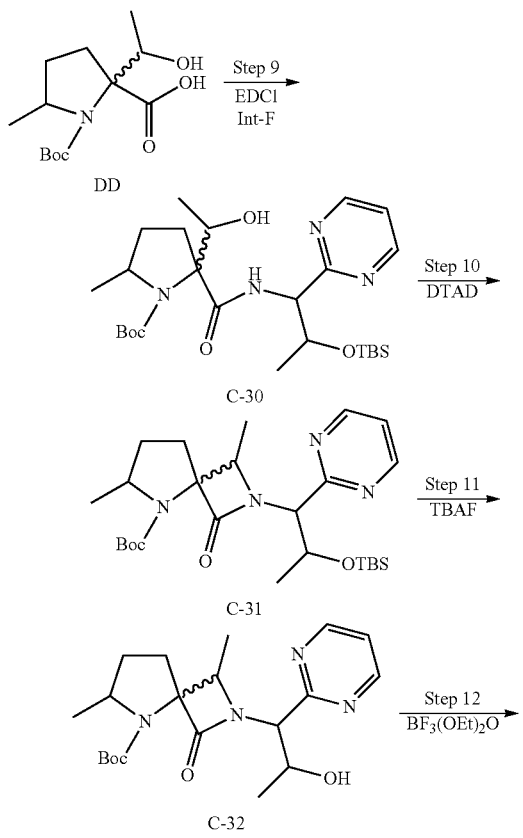

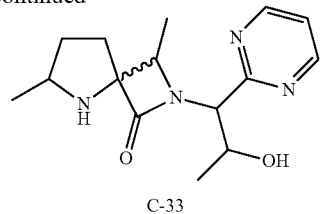

C-33

Synthesis of tert-butyl 2((2-((tert-butyldimethylsilyl)oxy)-1-(pyrimidin-2-yl)propyl)carbamoyl)-2-(1-hydroxyethyl)-5-methylpyrrolidine-1-carboxylate (C-30)

To a stirring solution of compound DD (500 mg, 1.83 mmol) in DCM (10 mL) were added N,N-diisopropylethylamine (0.84 mL, 4.57 mmol), intermediate F (586 mg, 2.19 mmol), followed by EDCI (296 mg, 2.19 mmol), HOBT (338 mg, 2.19 mmol) at 0° C. and stirred at RT for 16 h. After consumption of the starting material (by TLC), the reaction mixture was diluted with water (20 mL). The separated organic layer was washed with brine solution (1×20 mL). The separated organic layer was dried over anhydrous Na$_2$SO$_4$ and concentrated under reduced pressure to afford crude compound which was purified by column chromatography by eluting 2% MeOH/DCM to obtained compound C-30 (800 mg, 83.6%) as pale yellow liquid.

$^1$H-NMR: (500 MHz, DMSO-d$_6$): δ 8.78-8.75 (m, 2H), 7.42-7.39 (m, 1H), 5.01-4.92 (m, 1H), 4.21-4.09 (m, 1H), 4.05-4.02 (m, 2H), 1.98 (s, 2H), 1.44-1.31 (m, 7H), 1.29-1.11 (m, 10H), 1.02-0.96 (m, 4H), 0.70-0.63 (m, 9H), −0.25 (s, 3H), −0.32 (s, 3H).

LCMS (ESI): 523.6 [M$^+$+1].

Synthesis of tert-butyl 2-(2-((tert-butyldimethylsilyl)oxy)-1-(pyrimidin-2-yl)propyl)-1,6-dimethyl-3-oxo-2,5-diazaspiro[3,4]octane-5-carboxylate (C-31)

To a stirring solution of triphenylphosphine (1.23 g, 4.87 mmol) in dry THF (10 mL) was added DTAD (1.09 g, 4.77 mmol) as portion-wise and stirred for 15 min at RT. To this precipitated solution, added compound C-30 (1.0 g, 1.91 mmol) in dry THF (10 mL) slowly at RT and stirred for 16 h. After consumption of the starting material (by TLC), the reaction mixture was concentrated under reduced pressure. The crude material was triturated with n-pentane (20 mL) and filtered solid (TPPO). The filtrate was concentrated under reduced pressure to obtained crude compound was purified by silica gel column chromatography eluting 30% EtOAc/hexane to afford compound C-31 (400 mg, 41.4%) as yellow liquid.

$^1$H-NMR: (400 MHz, DMSO-d$_6$): δ 8.82-8.79 (m, 2H), 7.44-7.42 (m, 1H), 3.88-3.70 (m, 2H), 1.82-1.78 (m, 2H), 1.49-1.41 (m, 4H), 1.40 (s, 9H), 1.21-1.08 (m, 9H), 0.57 (s, 6H), −0.05 (s, 9H); LCMS (ESI): 505.5 [M$^+$+1].

Synthesis of tert-butyl 2-(2-hydroxy-1-(pyrimidin-2-yl)propyl)-1,6-dimethyl-3-oxo-2,5-diazaspiro[3,4]octane-5-carboxylate (C-32)

To a stirring solution of compound C-31 (220 mg, 0.43 mmol) in dry THF (3 mL) was added TBAF (227 mg) slowly at 0° C. and stirred at RT for 16 h. After consumption of the starting material (by TLC), the reaction mixture was concentrated under reduced pressure to afford crude, which was purified by silica gel column chromatography eluting 80% EtOAc/hexane to afford compound C-32 (150 mg, 88.2%) as yellow liquid.

¹H-NMR: (500 MHz, DMSO-d₆): δ 8.81-8.79 (m, 2H), 7.43-7.41 (m, 1H), 4.36-4.33 (m, 1H), 4.27-4.24 (m, 1H), 3.86-3.80 (m, 2H), 2.15-1.86 (m, 4H), 1.53-1.50 (m, 1H), 1.43 (s, 9H), 1.19-1.03 (m, 9H).

Synthesis of 2-(2-hydroxy-1-(pyrimidin-2-yl)propyl)-3,6-dimethyl-2, 5-diazaspiro[3,4]octan-1-one (C-33)

To a stirring solution of compound C-32 (120 mg, 0.25 mmol) in DCM (10 mL) was added molecular sieves (100 mg), BF₃(OEt)₂ (72 mg, 0.51 mmol) at 0° C. under N₂ atmosphere. The reaction mixture was stirred at RT for 10 min. After consumption of the starting material (by TLC), the obtained precipitate was triturated with n-pentane/diethylether (5 mL/5 mL) and the filtered solid was dried on vacuum to afford C-33 (80 mg, 89.8%) as white solid.

¹H-NMR: (400 MHz, D₂O): δ 8.90 (t, J=4.8 Hz, 2H), 7.64-7.60 (m, 1H), 4.72-4.62 (m, 2H), 4.24-4.15 (m, 1H), 4.08-4.00 (m, 1H), 2.60-2.32 (m, 3H), 2.02-1.91 (m, 1H), 1.55-1.51 (m, 3H), 1.48-1.45 (m, 3H), 1.39-1.25 (m, 3H).

LCMS (ESI): 581.3 [2M⁺+1].

Scheme 10

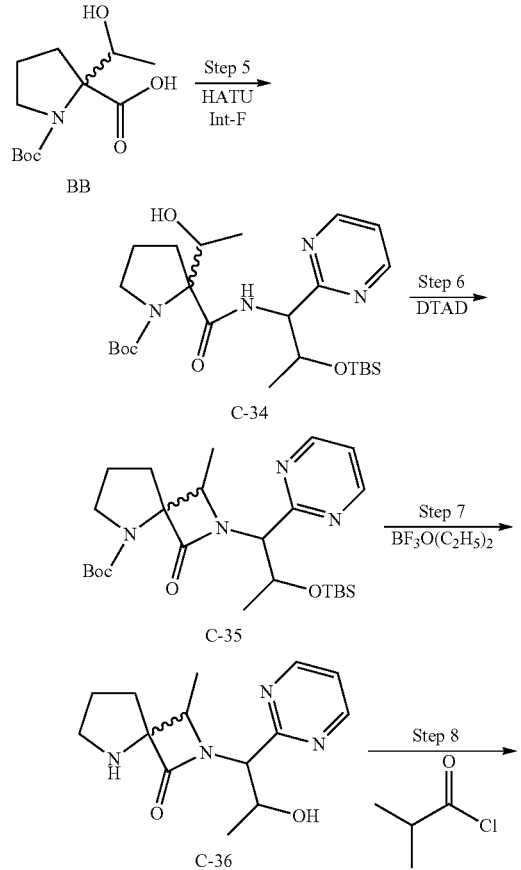

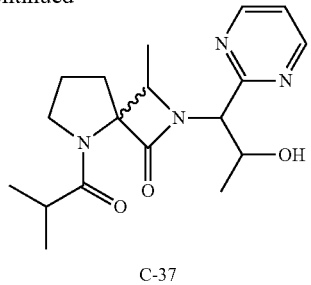

Synthesis of tert-butyl 2-((2-((tert-butyldimethylsilyl)oxy)-1-(pyrimidin-2-yl)propyl)carbamoyl)-2-(1-hydroxyethyl)pyrrolidine-1-carboxylate (C-34)

To a stirring solution of compound BB (2.5 g, 9.65 mmol) in CH₂Cl₂ (25 mL) were added DIPEA (5 mL, 28.95 mmol), intermediate F (2.57 g, 9.65 mmol) followed by HATU (4.4 g, 11.58 mmol) at 0° C. and stirred for 12 h at RT. After consumption of the starting material (by TLC), the reaction mixture was the reaction was diluted with water (20 mL). The separated organic layer was washed with citric acid solution (1×50 mL) followed by brine solution (1×50 mL). The organic layer was dried over anhydrous Na₂SO₄, filtered and concentrated under reduced pressure. Obtained crude material was purified by silica gel column chromatography eluting 50% EtOAc/n-hexane to afford compound C-34 (3.1 g, 63.2%) as an off-white solid.

¹H-NMR: (500 MHz, DMSO-d₆): δ 8.76 (d, J=13.5 Hz, 2H), 8.42 (d, J=9.0 Hz, 1H), 7.41 (d, J=9.0 Hz, 1H), 4.60-4.41 (m, 1H), 4.23-4.11 (m, 1H), 3.58-3.40 (m, 3H), 2.37-1.62 (m, 4H), 1.39 (s, 9H), 1.28-1.19 (m, 3H), 1.18-1.15 (m, 3H), 1.09 (s, 9H), −0.04 (s, 6H);

LCMS (ESI): m/z 509.7 [M⁺+1]

Synthesis of tert-butyl 2-(2-((tert-butyldimethylsilyl)oxy)-1-(pyrimidin-2-yl)propyl)-1-methyl-3-oxo-2,5-diazaspiro[3,4]octane-5-carboxylate (C-35)

To a stirring solution of triphenylphosphine (1.6 g, 6.29 mmol) in THF (15 mL) was added DIAD (1.44 g, 6.29 mmol) at RT and stirred for 30 min. To this added compound C-34 (1.6 g, 3.14 mmol) in (5 mL) THF slowly and reaction mixture was stirred at RT for 3 h. After consumption of the starting material (by TLC), the reaction was concentrated under reduced pressure. The crude material was triturated with diethyl ether/n-pentane (10 mL/10 mL). The filtered solvent was concentrated and purified by silica gel column chromatography eluting 20% EtOAc/n-hexane to afford compound C-35 (1 g, 65.3%) as pale yellow liquid.

¹H-NMR: (500 MHz, DMSO-d₆): δ 8.80 (d, J=14.5 Hz, 2H), 7.44 (d, J=9.0 Hz, 1H), 4.72-4.46 (m, 2H), 3.36-3.23 (m, 3H), 2.06-1.61 (m, 4H), 1.40 (s, 9H), 1.35-1.23 (m, 3H), 1.16-1.12 (m, 3H), 1.00 (s, 9H), −0.01 (s, 6H);

LCMS (ESI): m/z 491.4 [M⁺+1]

Synthesis of 2-(2-hydroxy-1-(pyrimidin-2-yl)propyl)-3-methyl-2,5-diazaspiro[3,4]octan-1-one (C-36)

To a stirring solution of compound C-35 (1 g, 2.04 mmol) in DCM (5 mL) was added BF₃O(C₂H₅)₂ (0.05 mL, 4.08 mmol) followed by molecular sieves (50 mg) at 0° C. and stirred to RT for 3 h. After consumption of the starting material (by TLC), the reaction was diluted with n-pentane and filtered the obtained solid. The filtered solid was purified by silica gel column chromatography eluting 5% MeOH/DCM to afford C-36 (180 mg, 32%) as an off-white solid.

$^1$H-NMR: (400 MHz, D$_2$O): δ 8.89 (d, J=4.8 Hz, 2H), 7.61 (t, J=4.8 Hz, 1H), 4.85-4.73 (m, 2H), 4.18-4.13 (m, 1H), 3.54-3.41 (m, 2H), 2.43-2.36 (m, 1H), 2.31-2.12 (m, 3H), 1.43-1.37 (m, 6H)

LCMS (ESI): m/z 277.3 [M$^+$+1];
HPLC: 98.85%.

Synthesis of 2-(2-hydroxy-1-(pyrimidin-2-yl)propyl)-5-isobutyryl-3-methyl-2,5-diazaspiro[3,4]octan-1-one (C-37)

To a stirring solution of compound C-36 (600 mg, 2.17 mmol) in CH$_2$Cl$_2$ (10 mL) was added TEA (1.05 mL, 7.59 mmol) at 0° C. After added isobutyryl chloride (253 mg, 2.39 mmol) slowly and stirred for 1 h at RT. After consumption of the starting material (by TLC), the reaction mixture was diluted with water (10 mL). The separated organic layer was washed with brine solution (1×50 mL). The organic layer was dried over anhydrous Na$_2$SO$_4$, filtered and concentrated under reduced pressure. Obtained crude material was purified by silica gel column chromatography eluting 3% MeOH/DCM followed by preparative HPLC purification to afford C-37 (120 mg, 16%) as an off-white solid.

$^1$H-NMR: (500 MHz, DMSO-d$_6$): δ 8.81 (d, J=7.5 Hz, 2H), 7.43 (d, J=11.5 Hz, 1H), 5.05-4.34 (m, 2H), 3.64-3.44 (m, 3H), 2.01-1.81 (m, 5H), 1.35-1.13 (m, 6H), 1.10-1.04 (m, 6H);

LCMS (ESI): m/z 347.4 [M$^+$+1]
HPLC: 91.1%

Preparation of Key Intermediates, Schemes I-8 to I-10

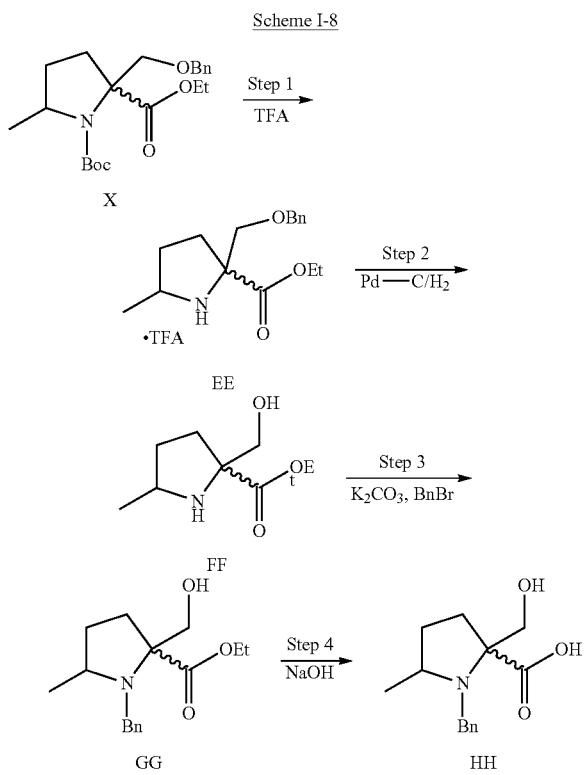

Synthesis of ethyl 2-((benzyloxy)methyl)-5-methyl-pyrrolidine-2-carboxylate (EE)

To a stirring solution of X (8.5 g, 22.51 mmol) in DCM (50 mL) was added TFA (8.6 mL, 112.58 mmol) at 0° C. The reaction mixture was stirred at RT for 4 h. After consumption of the starting material (by TLC), the reaction mixture was concentrated under reduced pressure to afford EE (14 g, crude) as pink liquid (TFA salt).

$^1$H-NMR: (400 MHz, DMSO-d$_6$): δ 9.71 (br s, 1H), 7.45-7.30 (m, 5H), 4.62 (s, 2H), 4.27-4.22 (m, 2H), 3.90-3.73 (m, 3H), 2.26-2.08 (m, 2H), 2.01-1.95 (m, 1H), 1.59-1.51 (m, 1H), 1.36-1.31 (m, 3H), 1.22-1.18 (m, 3H);

LCMS (ESI): m/z 278.36 [M$^+$+1]

Synthesis of ethyl 2-(hydroxymethyl)-5-methylpyrrolidine-2-carboxylate (FF)

To a stirring solution of EE (14 g (crude), 35.80 mmol) in methanol (100 mL) was added (50% wet) 10% Pd/C (5 g) under N$_2$ atmosphere. The reaction mixture was stirred under H$_2$ atmosphere (balloon pressure) at RT for 16 h. After consumption of the starting material (by TLC), the reaction mixture was filtered through a pad of celite and the pad was washed with methanol (100 mL). Obtained filtrate was concentrated under reduced pressure to afford FF (8 g, crude) as yellow syrup.

$^1$H-NMR: (400 MHz, DMSO-d$_6$): δ 9.52 (s, 1H), 8.74 (s, 1H), 4.28-4.20 (m, 2H), 3.94-3.69 (m, 3H), 2.22-2.16 (m, 2H), 2.13-1.92 (m, 1H), 1.60-1.53 (m, 1H), 1.32-1.18 (m, 6H);

LCMS (ESI): m/z 188.24 [M$^-$+1]

Synthesis of ethyl 1-benzyl-2-(hydroxymethyl)-5-methylpyrrolidine-2-carboxylate (GG)

To a stirring solution of FF (8 g, 26.57 mmol) in CH$_3$CN (50 mL) was added K$_2$CO$_3$ (11.02 g, 79.73 mmol) followed by benzyl bromide (3.78 mL, 31.89 mmol) at RT and stirred for 16 h. After consumption of the starting material, filtered the reaction mass through celite bed and filtrate was washed with EtOAc (250 mL). The filtrate was concentrated under reduced pressure to afford crude. Obtained crude material was purified by column chromatography eluting with 10% EtOAc/Hexane to afford GG (5 g, 68%) as brown syrup.

$^1$H-NMR: (500 MHz, DMSO-d$_6$): δ 7.33-7.15 (m, 5H), 5.17 (t, J=5.5 Hz, 1H), 4.75 (d, J=5.5 Hz, 1H), 4.50 (d, J=6.0 Hz, 1H), 4.14-3.93 (m, 2H), 3.93 (s, 2H), 3.81-3.60 (m, 1H), 3.13-3.09 (m, 1H), 2.20-2.17 (m, 1H), 1.99-1.88 (m, 2H), 1.40-1.36 (m, 3H), 1.14 (t, J=7.0 Hz, 3H)

LCMS (ESI): m/z 278.36 [M$^+$+1]

Synthesis of 1-benzyl-2-(hydroxymethyl)-5-methyl-pyrrolidine-2-carboxylic acid (HH)

To a stirring solution of GG (5 g, 18.05 mmol) in EtOH/H$_2$O (25 mL/25 mL) were added NaOH (1.44 g, 36.1 mg) at RT. The reaction mixture was heated to 100° C. for 2 h. After consumption of the starting material (by TLC), the solvent from the reaction was evaporated under reduced pressure and extracted with di ethylether (2×75 mL). The aqueous layer was acidified by using 1N HCl and extracted with 20% MeOH/CH$_2$Cl$_2$ (2×100 mL). The organic layer was dried over anhydrous Na$_2$SO$_4$, filtered and concentrated under reduced pressure to afford HH (3.5 g, 78%) as brown syrup.

¹H-NMR: (400 MHz, DMSO-d₆): δ 11.17 (s, 1H), 7.49-7.27 (m, 5H), 4.55 (d, J=14.0 Hz, 1H), 4.06 (d, J=14.4 Hz, 1H), 3.83 (s, 2H), 3.51-3.41 (m, 2H), 2.18-1.90 (m, 3H), 1.45-1.39 (m, 1H), 0.61-0.45 (m, 3H)
LCMS (ESI): m/z 250.13 [M⁺+1]

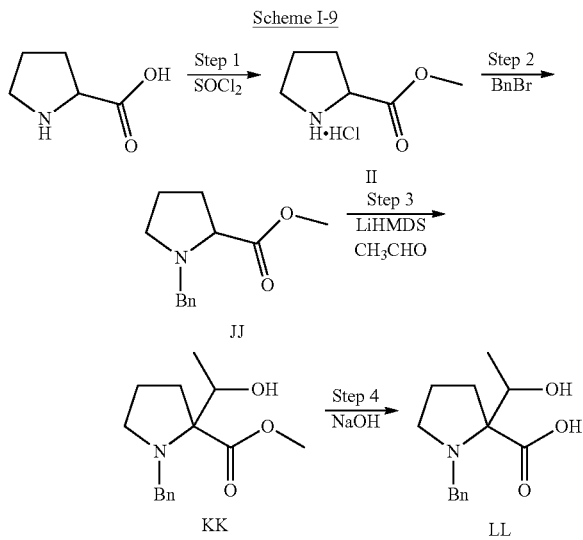

Synthesis of methyl pyrrolidine-2-carboxylate (II)

To a stirring solution of L-Proline (50 g, 434 mmol) in methanol was added thionyl chloride (37.5 ml, 521 mmol) at 0° C. and heated to 70° C. for 16 h. The reaction mixture was brought to RT and concentrated under vacuum to afford II as (70 g, 99%) as thick syrup (hydrochloride salt).
¹H-NMR: (500 MHz, DMSO-d₆): δ 4.15-4.13 (m, 1H), 3.65 (s, 3H), 3.35-3.30 (m, 2H), 2.23-2.15 (m, 1H), 1.86-1.78 (m, 3H), 1.41 (s, 9H)
LCMS (ESI): m/z 129 [M⁺+1]

Synthesis of methylbenzylprolinate (JJ)

To a stirring solution of compound II (18 g, 108 mmol) in DCM (200 mL) was added TEA (45.35 mL, 326 mmol) followed by benzyl bromide (15.5 mL, 130 mmol) at 0° C. and stirred at RT for 24 h. After completion of the reaction (by TLC) was diluted with water (75 mL) and EtOAc (500 mL). The organic layer was washed with water (2×100 mL), brine solution (2×50 mL). The organic layer was dried over anhydrous Na₂SO₄ and concentrated under vacuum. Obtained crude material was purified by column chromatography eluting with 10% EtOAc/Hexane to afford JJ (5 g, 21%) as oily liquid.
¹H-NMR: (400 MHz, DMSO-d₆): δ 7.32-7.22 (m, 5H), 3.86-3.80 (m, 1H), 3.58 (s, 3H), 3.48-3.24 (m, 2H), 2.85-2.80 (m, 1H), 2.38-2.32 (m, 1H), 2.10-1.98 (m, 1H), 1.85-1.69 (m, 3H)
LCMS (ESI): m/z 220.28 [M⁺+1]

Synthesis of methyl 1-benzyl-2-(1-hydroxyethyl)pyrrolidine-2-carboxylate (KK)

To a stirring solution of JJ (5 g, 22.80 mmol) in THF (50 mL) was added LiHMDS (46 mL, 45.60 mmol) dropwise at −20° C. and stirred for 45 min. To this acetaldehyde (2.33 mL, 45.60 mmol) was added drop wise and stirred for 3 h at −20° C. After consumption of the starting material (by TLC), the reaction was quenched with aqueous NH₄Cl solution (100 mL) and extracted with EtOAc (2×150 mL). The separated organic layer was washed with water (200 mL) and brine solution (200 mL). The separated organic layer was dried over Na₂SO₄ and concentrated to afford crude which was purified by column chromatography eluting with 10% EtOAc/Hexane to afford KK (3.5 g, 58%) as yellow syrup.
LCMS (ESI): m/z 264.3 [M¹+1]

Synthesis of 1-benzyl-2-(1-hydroxyethyl)pyrrolidine-2-carboxylic acid (LL)

To a stirring solution of KK (4.5 g, 17.11 mmol) in MeOH/THF/H₂O (10 mL/10 mL/10 mL) were added NaOH (1.02 g, 25.66 mmol) at RT. The reaction mixture was heated to 95° C. for 1 h. After consumption of the starting material (by TLC), the solvent was evaporated under reduced pressure. The aqueous layer was washed with EtOAc (100 mL). The separated aqueous layer was acidified by using 1N HCl (pH ~3). The aqueous layer was extracted with 20% MeOH/DCM (2×100 mL). The combined organic layer was dried over Na₂SO₄ and concentrated under reduced pressure to afford LL (2.7 g, 63%) as an off-white solid.
¹H-NMR: (400 MHz, DMSO-d₆): δ 7.31-7.13 (m, 5H), 3.87-3.78 (m, 2H), 3.61-3.57 (m, 1H), 2.75-2.64 (m, 2H), 1.90-1.78 (m, 2H), 1.69-1.65 (m, 1H), 1.53-1.43 (m, 1H), 1.06 (d, J=6.4 Hz, 3H);
LCMS (ESI): m/z 250.4 [M⁺−1]

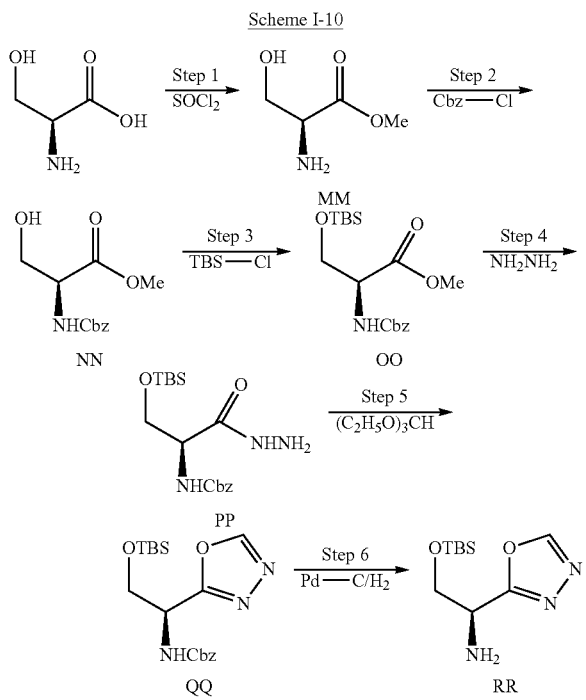

Synthesis of methyl L-serinate (MM)

To a stirring solution of L-serine (12 g, 114 mmol) in CH₃OH (100 mL) was added thionyl chloride (10 mL, 137 mmol) at 0° C. and stirred at 80° C. for 16 h. After completion of starting material (by TLC), the reaction mixture was concentrated under reduced pressure to afford MM (16 g, crude, HCl salt) as white solid. This material was directly used for the next step without further purification.

¹H-NMR: (400 MHz, DMSO-d₆): δ 8.61 (s, 2H), 4.50 (s, 1H), 4.20-4.16 (m, 1H), 3.82 (d, J=3.6 Hz, 2H), 3.73 (s, 3H).

Synthesis of methyl((benzyloxy)carbonyl)-L-serinate (NN)

To a stirring solution of MM (16 g, 103 mmol) in water/1,4 dioxane (130 mL/65 mL) were added added Na₂CO₃ (273 g, 257 mmol) at RT. After added Cbz-Cl (17.6 mL, 123 mmol) was added at 0° C. drop wise and stirred for 16 h at RT. After completion of starting material (by TLC), diluted the reaction mass with EtOAc (300 ml). The separated organic layer was dried over anhydrous Na₂SO₄, filtered and concentrated under reduced pressure to afford crude material which was purified by column chromatography to afford NN (23 g, 88%) as thick syrup.

¹H-NMR: (500 MHz, DMSO-d₆): δ 7.50 (d, J=8.0 Hz, 1H), 7.38-7.31 (m, 5H), 5.04 (s, 2H), 4.95-4.92 (m, 1H), 4.17-4.13 (m, 1H), 3.66 (s, 3H), 3.65-3.56 (m, 2H).
LCMS (ESI): m/z 254.2 [M⁺+1]

Synthesis of methyl N-((benzyloxy)carbonyl)-O-(tert-butyldimethylsilyl)-L-serinate (OO)

To a stirring solution of NN (23 g, 91 mmol) in DCM (700 mL) were added imidazole (12.37 g, 182 mmol), DMAP (2.22 g, 18.2 mmol) followed by TBDMS-Cl (20.4 g, 136 mmol) at 0° C. and stirred at RT for 16 h. After completion of starting material (by TLC), diluted the reaction mass with water (200 ml). The separated organic layer was washed with brine solution (2×200 mL). The organic layer was dried over anhydrous Na₂SO₄, filtered and concentrated under reduced pressure to afford crude material was purified by column chromatography eluting 20% EtOAc/hexane to afford OO (32 g, 97%) as thick syrup.

¹H-NMR: (400 MHz, DMSO-d₆): δ 7.56 (d, J=8.0 Hz, 1H), 7.38-7.30 (m, 5H), 5.07 (s, 2H), 4.24-4.19 (m, 1H), 3.81 (d, J=5.2 Hz, 2H), 3.63 (s, 3H), 0.84 (s, 9H), −0.04 (s, 6H)
LCMS (ESI): m/z 368.5 [Mⁱ+1]

Synthesis of benzyl (S)-(3-((tert-butyldimethylsilyboxy)-1-hydrazinyl-1-oxopropan-2-yl)carbamate (PP)

To a stirred solution of OO (20 g, 54.5 mmol) in methanol (120 mL) was added hydrazine hydrate (27 g, 545 mmol) at 0° C. and after stirred at 80° C. for 2 h. After completion of starting material (by TLC), ethanol was evaporated under reduced pressure. The crude residue was triturated with n-pentane (100 mL) to afford PP (17 g, 85%) as an off-white solid.

¹H-NMR: (500 MHz, DMSO-d₆): δ 9.17 (s, 1H), 9.10 (s, 1H), 7.35-7.14 (m, 5H), 5.02 (s, 2H), 4.48 (s, 2H), 4.16-4.07 (m, 2H), 3.73-3.58 (m, 1H), 0.81 (s, 9H), −0.04 (s, 6H).

Synthesis of benzyl 2R)-2-((tert-butyldimethylsilyl)oxy)-1-(1,3,4-oxadiazol-2-yl)propyl)carbamate (QQ)

A solution of PP (17 g, 46.3 mmol) in triethylorthoformate (68.5 g, 463 mmol) was added p-TSA (8.8 g, 4.63 mmol) at RT and after stirred at 80° C. for 2 h. After completion of starting material (by TLC), triethylorthoformate was evapo-rated under reduced pressure. The crude residue was purified by column chromatography eluting 10% EtOAc/hexane to afford QQ (5 g, 29%) as thick syrup.

¹H-NMR: (500 MHz, DMSO-d₆): δ 9.22 (s, 1H), 8.05 (d, J=7.5 Hz, 1H), 7.36-7.30 (m, 5H), 5.08 (s, 2H), 5.05-4.97 (m, 1H), 4.03-3.91 (m, 2H), 0.84 (s, 9H), 0.03 (s, 6H);
LCMS (ESI): m/z 378.5 [M⁺+1]

Synthesis of (S)-2-((tert-butyldimethylsilyl)oxy)-1-(1,3,4-oxadiazol-2-yl)ethan-1-amine (RR)

To a stirring solution of QQ (5 g, 13.2 mmol) in methanol (30 mL) was added 50% wet 10% Pd/C (1.2 g) and stirred under H₂ atmosphere (balloon pressure) for 2 h at RT. After completion of reaction, the reaction mixture was filtered through a pad of celite and triturated with methanol (20 mL). The filtrate was concentrated under reduced pressure to afford RR (2 g, 63%) as thick syrup.

¹H-NMR: (400 MHz, DMSO-d₆): δ 9.16 (s, 1H), 4.19-4.16 (m, 1H), 3.85-3.75 (m, 2H), 2.11 (s, 2H), 0.77 (s, 9H), −0.04 (s, 6H)
LCMS (ESI): m/z 244.3 [M⁺+1]

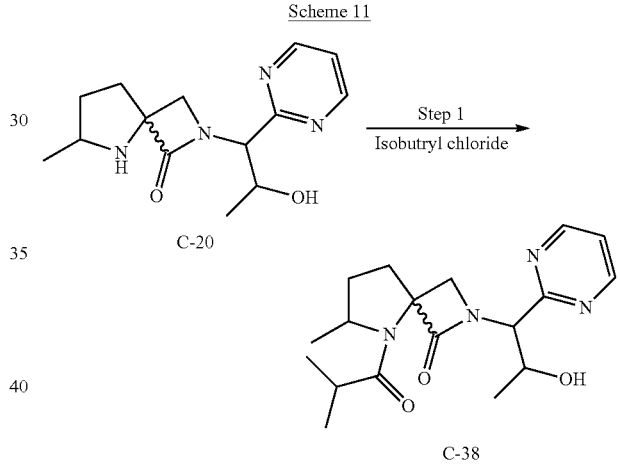

Scheme 11

Synthesis of 2-(2-hydroxy-1-(pyrimidin-2-yl)propyl)-5-isobutyryl-6-methyl-2,5-diazaspiro[3,4]octan-1-one (C-38)

To a stirring solution of C-20 (500 mg, 1.81 mmol) in DCM (10 mL) was added DIPEA (0.94 mL, 5.43 mmol) at 0° C. After added iso butyrylchloride (578 mg, 5.43 mmol) at 0° C. and stirred at RT for 4 h. After consumption of the starting material (by TLC), the reaction mixture was diluted with water (10 mL). The separated organic layer was dried over anhydrous Na₂SO₄ and concentrated under reduced pressure to afford crude compound which was purified by column chromatography by eluting 2% MeOH/DCM to obtained C-38 (150 mg, 24%) as pale yellow solid.

¹H-NMR: (400 MHz, CD₃OD): δ 8.82-8.77 (m, 2H), 7.39 (t, J=5.2 Hz, 1H), 4.76 (d, J=8.0 Hz, 1H), 4.47-4.44 (m, 1H), 4.20-4.14 (m, 1H), 3.82-3.74 (m, 1H), 3.51-3.40 (m, 1H), 2.78-2.72 (m, 1H), 2.46-2.37 (m, 1H), 2.18-2.12 (m, 2H), 1.77-1.72 (m, 1H), 1.34-1.29 (m, 3H), 1.26-1.22 (m, 3H), 1.06-1.02 (m, 6H)
LCMS (ESI): m/z 347.2 [M⁺+1];
HPLC: 99.7%

Scheme 12

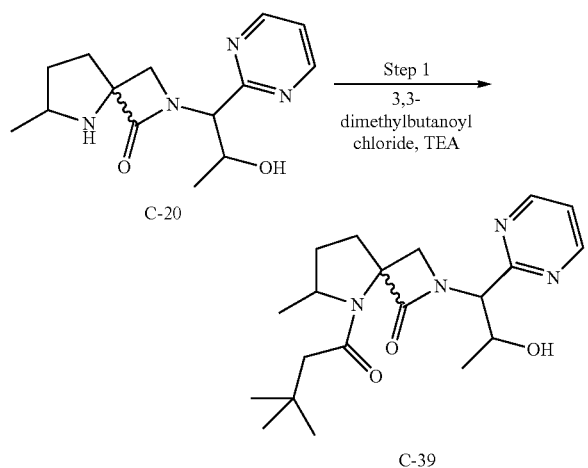

Synthesis of 5-(3,3-dimethylbutanoyl)-2-(2-hydroxy-1-(pyrimidin-2-ylpropyl)-6-methyl-2,5-diazaspiro[3,4]octan-1-one (C-39)

To a stirring solution of C-20 (150 mg, 0.54 mmol) in DCM (10 mL) was added TEA (137 mg, 1.35 mmol) at 0° C. After added 3,3-dimethylbutanoyl chloride (87 mg, 0.65 mmol) at 0° C. and stirred at RT for 1 h. After consumption of the starting material (by TLC), the reaction mixture was diluted with water (10 mL). The separated organic layer was dried over anhydrous $Na_2SO_4$ and concentrated under reduced pressure to afford crude compound which was purified by column chromatography by eluting 2% MeOH/DCM to obtained C-39 (150 mg, 24%) as sticky solid.

$^1$H-NMR: (400 MHz, DMSO-$d_6$): δ 8.80-8.75 (m, 2H), 7.43-7.37 (m, 1H), 4.73-4.65 (m, 2H), 4.24-4.17 (m, 2H), 3.78-3.59 (m, 1H), 3.23-3.16 (m, 1H), 2.36 (s, 2H), 2.32-2.08 (m, 3H), 1.58-1.50 (m, 1H), 1.20-1.08 (m, 6H), 0.86 (s, 9H)

LCMS (ESI): m/z 375.49 [M$^+$+1];
HPLC: 96.9%

Scheme 13

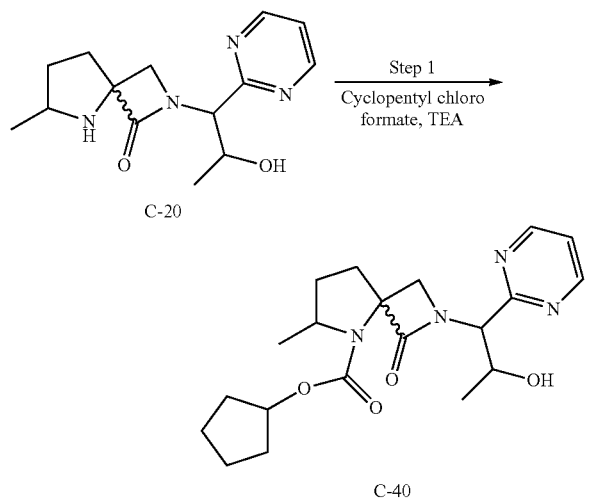

Synthesis of cyclopentyl 2-(2-hydroxy-1-(pyrimidin-2-yl)propyl)-6-methyl-1-oxo-2,5-diazaspiro[3,4]octane-5-carboxylate (C-40)

To a stirring solution of C-20 (150 mg, 0.54 mmol) in DCM (5 mL) was added TEA (0.23 mL, 1.63 mmol) at 0° C. After added cyclopentyl chloroformate (88 mg, 0.59 mmol) at 0° C. and stirred at RT for 1 h. After consumption of the starting material (by TLC), the reaction mixture was diluted with water (10 mL). The separated organic layer was washed with saturated brine solution (20 mL). The organic layer was dried over anhydrous $Na_2SO_4$ and concentrated under reduced pressure to afford crude compound which was purified by column chromatography by eluting 3% MeOH/DCM to obtained C-40 (110 mg, 52%) as sticky solid.

$^1$H-NMR: (400 MHz, DMSO-$d_6$): δ 8.81-8.76 (m, 2H), 7.45-7.42 (m, 1H), 5.20-4.91 (m, 1H), 4.77-4.64 (m, 2H), 4.30-3.63 (m, 1H), 3.57-3.31 (m, 3H), 2.16-1.86 (m, 4H), 1.77-1.32 (m, 8H), 1.18-1.08 (m, 6H)

LCMS (ESI): m/z 389.4 [M$^+$+1];
UPLC: 97.6%

Scheme 14

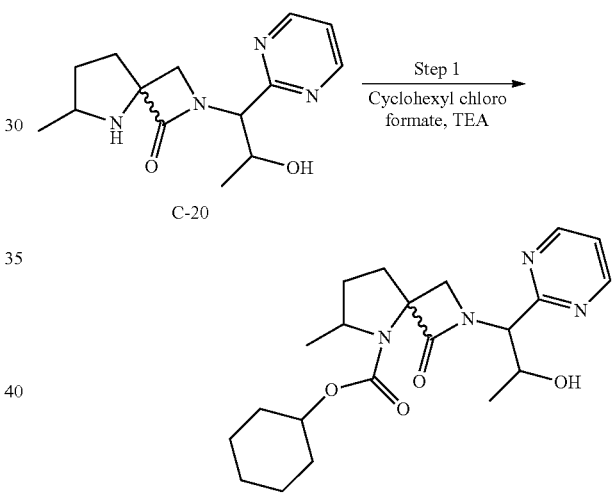

Synthesis of cyclohexyl 2-(2-hydroxy-1-(pyrimidin-2-yl)propyl)-6-methyl-1-oxo-2,5-diazaspiro[3,4]octane-5-carboxylate (C-41)

To a stirring solution of C-20 (150 mg, 0.54 mmol) in DCM (5 mL) was added TEA (0.2 mL, 1.35 mmol) at 0° C. After added cyclohexyl chloroformate (105 mg, 0.65 mmol) at 0° C. and stirred at RT for 1 h. After consumption of the starting material (by TLC), the reaction mixture was diluted with water (10 mL). The separated organic layer was washed with citric acid solution (20 mL), saturated brine solution (20 mL). The organic layer was dried over anhydrous $Na_2SO_4$ and concentrated under reduced pressure to afford crude compound which was purified by column chromatography by eluting 2% MeOH/DCM to obtained C-41 (90 mg, 41%) as sticky solid.

$^1$H-NMR: (400 MHz, DMSO-$d_6$): δ 8.82-8.78 (m, 2H), 7.48-7.41 (m, 1H), 4.78-4.61 (m, 2H), 4.24-4.13 (m, 2H), 3.94-3.87 (m, 1H), 3.76-3.53 (m, 2H), 2.27-1.99 (m, 3H), 1.97-1.92 (m, 1H), 1.56-1.32 (m, 10H), 1.29-1.10 (m, 2H)

LCMS (ESI): m/z 403.5 [M++1];
UPLC: 98.06%

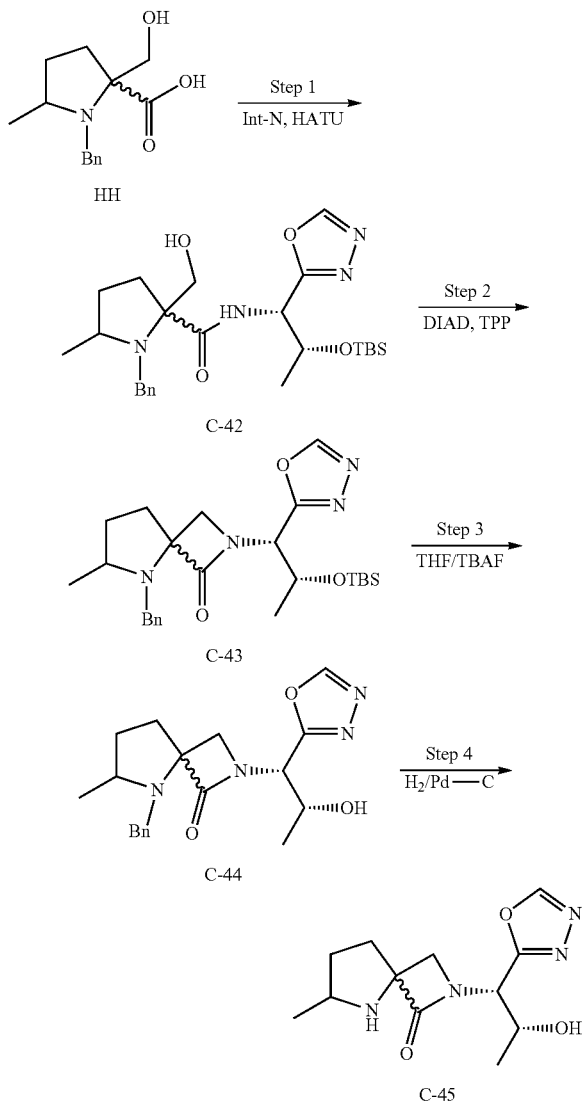

Scheme 15

Synthesis of 1-benzyl-N-((1S, 2R)-2-((tert-butyldimethylsilyl)oxy)-1-(1, 3, 4-oxadiazol-2-yl)propyl)-2-(hydroxymethyl)-5-methylpyrrolidine-2-carboxamide (C-42)

To a stirring solution of HH (2.5 g, 10.04 mmol) in DMF (15 mL) were added N,N-diisopropylethylamine (5.4 mL, 30.12 mmol), Int N (2.58 g, 10.04 mmol) followed by HATU (4.57 g, 12.04 mmol) at 0° C. and stirred at RT for 16 h. After consumption of the starting material (by TLC), the reaction mixture was diluted with water (100 mL) and EtOAc (100 mL). The organic layer was washed with water (100 mL), saturated sodium bicarbonate solution (50 mL) followed by brine solution (50 mL). The organic layer was dried over anhydrous $Na_2SO_4$, filtered and concentrated under reduced pressure to afford crude compound which was purified by column chromatography by eluting 20% EtOAc/n-hexane to obtained C-42 (3.2 g, 65%) as brown syrup.

$^1$H-NMR: (500 MHz, DMSO-$d_6$): δ 9.26 (s, 1H), 8.78 (d, J=10.0 Hz, 1H), 7.30-7.21 (m, 5H), 5.26 (d, J=10.0 Hz, 1H), 4.43 (s, 2H), 4.05-4.02 (m, 2H), 3.87-3.72 (m, 1H), 3.15-3.10 (m, 1H), 2.81-2.65 (m, 1H), 1.39-1.26 (m, 4H), 1.25-1.16 (m, 6H), 0.05 (s, 6H)
LCMS (ESI): m/z 489.70 [M++1]

Synthesis of 5-benzyl-2-((1S, 2R)-2-((tert-butyldimethylsilyl)oxy)-1-(1,3,4-oxadiazol-2-yl)propyl)-6-methyl-2,5-diazaspiro[3,4]octan-1-one (C-43)

To a stirring solution of triphenylphosphine (4.02 g, 15.36 mmol) in dry THF (30 mL) was added DIAD (2.48 g, 12.29 mmol) at RT and stirred for 15 min. After added C-42 (3 g, 6.14 mmol) in THF (30 mL) was added dropwise and the reaction mixture was stirred at RT for 4 h. After consumption of the starting material (by TLC), the reaction mixture was concentrated under reduced pressure. The crude material was purified by column chromatography by eluting 20% EtOAc/n-hexane to afford C-43 (1.3 g, 45%) as pale green syrup.

$^1$H-NMR: (400 MHz, DMSO-$d_6$): δ 9.28 (s, 1H), 7.33-7.19 (m, 5H), 5.24-5.19 (m, 1H), 4.73 (s, 2H), 4.47-4.41 (m, 1H), 4.02 (t, J=7.2 Hz, 1H), 3.68 (s, 2H), 2.49-2.28 (m, 1H), 2.27-2.10 (m, 1H), 1.98-1.94 (m, 1H), 1.47-1.40 (m, 1H), 1.23-1.15 (m, 6H), 0.87 (s, 9H), 0.02 (s, 6H)
LCMS (ESI): m/z 491.6 [M++1]

Synthesis of 5-benzyl-2-((1S, 2R)-2-hydroxy-1-(1,3,4-oxadiazol-2-yl) propyl)-6-methyl-2,5-diazaspiro[3,4]octan-1-one (C-44)

To a stirring solution of C-43 (1.3 g, 2.76 mmol) in dry THF (30 mL) was added TBAF (1M in THF) (4.13 mL, 4.14 mmol) at 0° C. and stirred for 2 h at RT. After consumption of the starting material (by TLC), the reaction mixture was concentrated under reduced pressure. The crude material was diluted with water (100 mL) and EtOAc (100 mL). The organic layer was washed with water (100 mL), brine solution (50 mL). The organic layer was dried over anhydrous $Na_2SO_4$, filtered and concentrated under reduced pressure to afford crude compound which was purified by column chromatography by eluting 2% MeOH/$CH_2Cl_2$ to obtained C-44 (350 mg, 35%) as thick syrup.

$^1$H-NMR: (400 MHz, DMSO-$d_6$): δ 9.18 (s, 1H), 7.34-7.16 (m, 5H), 5.21 (t, J=5.6 Hz, 1H), 5.01-4.83 (m, 1H), 4.22-4.18 (m, 1H), 3.88 (s, 2H), 3.84-3.67 (m, 1H), 3.54-3.35 (m, 1H), 2.98-2.89 (m, 1H), 2.31-1.89 (m, 3H), 1.45-1.41 (m, 1H), 1.39-1.14 (m, 3H), 0.90-0.81 (s, 3H)
LCMS (ESI): m/z 357.43 [M++1]
HPLC: 92.46%

Synthesis of 5-benzyl-2-((1S, 2R)-2-hydroxy-1-(1,3,4-oxadiazol-2-yl) propyl)-6-methyl-2,5-diazaspiro[3,4]octan-1-one (C-45)

To a stirring solution of C-44 (1.3 g, 2.76 mmol) in dry THF (30 mL) was added TBAF (1M in THF) (4.13 mL, 4.14 mmol) at 0° C. and stirred for 2 h at RT. After consumption of the starting material (by TLC), the reaction mixture was concentrated under reduced pressure. The crude material was diluted with water (100 mL) and EtOAc (100 mL). The organic layer was washed with water (100 mL), brine solution (50 mL). The organic layer was dried over anhydrous $Na_2SO_4$, filtered and concentrated under reduced pressure to afford crude compound which was purified by column chromatography by eluting 2% MeOH/CH$_2$Cl$_2$ to obtained C-45 (350 mg, 35%) as thick syrup.

$^1$H-NMR: (400 MHz, DMSO-d$_6$): δ 9.18 (s, 1H), 7.34-7.16 (m, 5H), 5.21 (t, J=5.6 Hz, 1H), 5.01-4.83 (m, 1H), 4.22-4.18 (m, 1H), 3.88 (s, 2H), 3.84-3.67 (m, 1H), 3.54-3.35 (m, 1H), 2.98-2.89 (m, 1H), 2.31-1.89 (m, 3H), 1.45-1.41 (m, 1H), 1.39-1.14 (m, 3H), 0.90-0.81 (s, 3H)

LCMS (ESI): m/z 357.43 [M$^+$+1]
HPLC: 92.46%

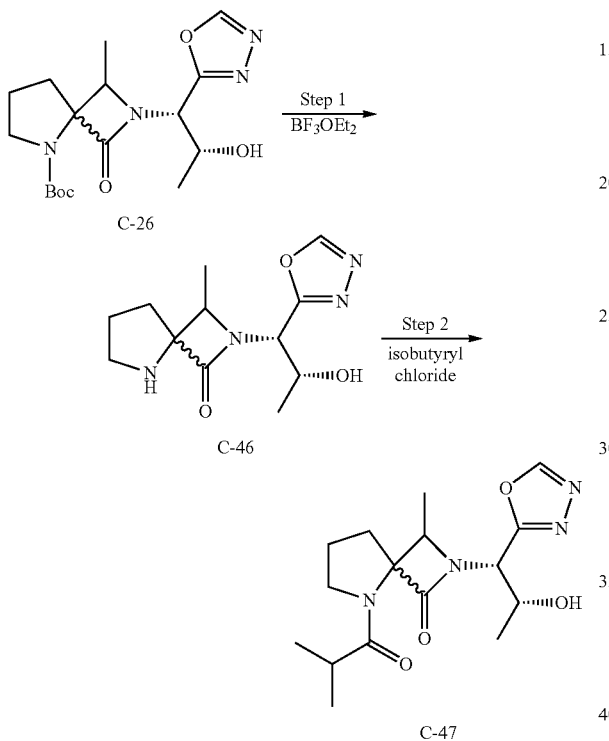

Scheme 16

C-26

C-46

C-47

Synthesis of 2-((1S,2R)-2-hydroxy-1-(1,3,4-oxadiazol-2-yl)propyl)-3-methyl-2,5-diazaspiro[3,4]octan-1-one (C-46)

To a stirring solution of C-26 (800 mg, 2.18 mmol) in DCM (10 mL) were added BF$_3$OEt$_2$ (620 mg, 4.37 mmol), molecular sieves (150 mg) at 0° C. and stirred for 3 h at RT. After consumption of the starting material (by TLC), the reaction mixture was diluted with n-pentane (5 mL). The precipitated solid was filtered and filtrate was concentrated under reduced pressure. Obtained crude material was purified by silica gel column chromatography eluting with 3% MeOH/DCM to afford C-46 (700 mg, crude) as yellow liquid.

Mass (ESI): m/z 267.3 [M$^+$+1]

Synthesis of 2-((1S,2R)-2-hydroxy-1-(1,3,4-oxadiazol-2-yl)propyl)-5-isobutyryl-3-methyl-2,5-diazaspiro[3,4]octan-1-one (C-47)

To a stirring solution of C-46 (700 mg (crude), 2.63 mmol) in DCM (10 mL) was added TEA (0.53 mL, 3.94 mmol) at 0° C. After 10 min added isobutyryl chloride (0.41 mL, 3.94 mmol) at 0° C. and stirred for 2 h at RT. After consumption of the starting material (by TLC), the reaction mixture was diluted with water (5 mL). The separated organic layer was dried over anhydrous Na$_2$SO$_4$, filtered and concentrated under reduced pressure. Obtained crude material was purified by silica gel column chromatography eluting with 3% MeOH/DCM followed by preparative HPLC purification to afford C-47 (150 mg, 17%) as thick syrup.

$^1$H-NMR: (400 MHz, DMSO-d$_6$): δ 9.27 (s, 1H), 5.20-5.17 (m, 1H), 4.87-4.85 (m, 1H), 4.30-4.25 (m, 1H), 3.84-3.79 (m, 1H), 3.64-3.50 (m, 2H), 2.72-2.66 (m, 1H), 2.13-2.09 (m, 1H), 2.01-1.79 (m, 3H), 1.37-1.19 (m, 3H), 1.10-0.94 (m, 9H)

Mass (ESI): m/z 337.4 [M$^+$+1]
HPLC: 99.5%

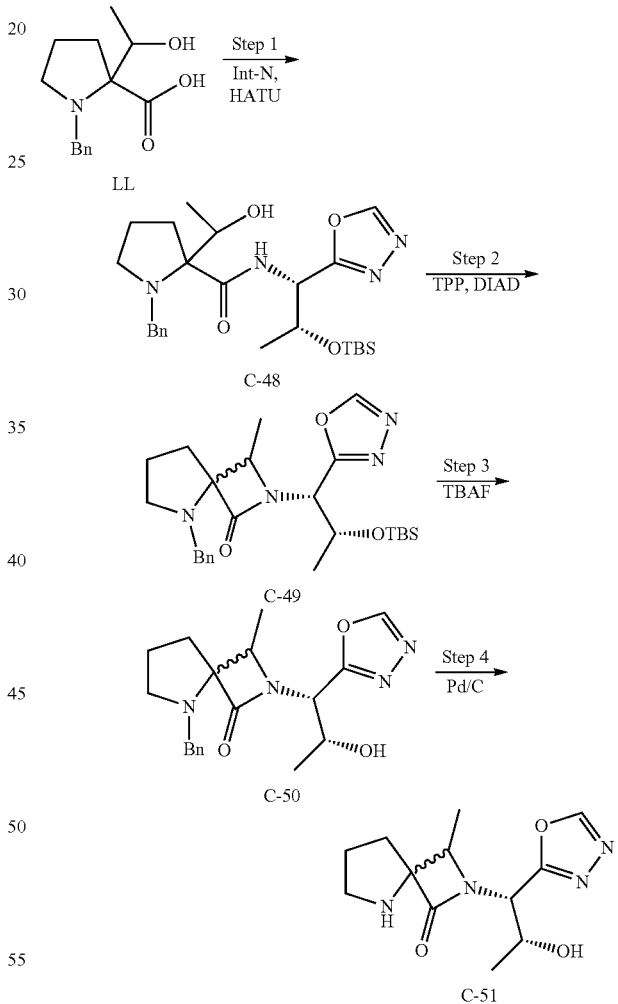

Scheme 17

LL

C-48

C-49

C-50

C-51

Synthesis of 1-benzyl-N-((1S, 2R)-2-((tert-butyldimethylsilyl) oxy)-1-(1,3,4-oxadiazol-2-yl)propyl)-2-(1-hydroxyethyl) pyrrolidine-2-carboxamide (C-48)

To a stirring solution of LL (3.9 g, 15.66 mmol) in DMF (10 mL) were added X 2V-diisopropylethylamine (8.16 mL, 46.98 mmol), Int-N (4.03 g, 15.66 mmol) followed by HATU (7.14 g, 18.79 mmol) at 0° C. and stirred at RT for 16 h. After consumption of the starting material (by TLC), the reaction mixture was diluted with water (100 mL) and EtOAc (150 mL). The separated organic layer was washed with water (100 mL) followed by brine solution (100 mL). The organic layer was dried over anhydrous $Na_2SO_4$ and concentrated under reduced pressure to afford crude compound which was purified by column chromatography by eluting 30% EtOAc/n-hexane to obtained C-48 (1.8 g, 24%) as yellow syrup.

$^1$H-NMR: (400 MHz, DMSO-$d_6$): δ 9.25 (s, 1H), 8.74 (d, J=8.8 Hz, 1H), 7.34-7.21 (m, 5H), 5.47-5.27 (m, 1H), 5.26-5.23 (m, 1H), 4.42-4.40 (m, 1H), 4.13-4.01 (m, 2H), 3.82-3.77 (m, 1H), 2.70-2.60 (m, 2H), 1.99-1.82 (m, 2H), 1.69-1.64 (m, 2H), 1.29-1.21 (m, 6H), 0.72 (s, 9H), −0.01 (s, 3H), −0.02 (s, 3H);

LCMS (ESI): m/z 489.6 [M$^+$+1]

Synthesis of 5-benzyl-2-((1S, 2R)-2-((tert-butyldimethylsilyl)oxy)-1-(1,3,4-oxadiazol-2-yl)propyl)-3-methyl-2,5-diazaspiro[3,4]octan-1-one (C-49)

To a stirring solution of triphenylphosphine (2.41 g, 9.22 mmol) in dry THF (20 mL) was added DIAD (1.49 g, 7.37 mmol) as portionwise and stirred for 15 min at RT. To this precipitated solution added C-48 (1.8 g, 3.68 mmol) in dry THF (15 mL) dropwise at RT and stirred for 16 h. After consumption of the starting material (by TLC), the reaction mixture was concentrated under reduced pressure. The obtained solid was triturated with 20% di ehylether/n-hexane (2×100 mL). The filterate was concentrated under reduced pressure to obtained crude compound which was purified by silica gel column chromatography eluting 20% EtOAc/hexane to afford C-49 (400 mg, crude) as pale green syrup.

$^1$H-NMR: (400 MHz, DMSO-$d_6$): δ 9.30 (s, 1H), 7.40-7.24 (m, 5H), 5.26-5.22 (m, 1H), 4.80-4.73 (m, 2H), 4.62-4.48 (m, 1H), 4.15-4.00 (m, 1H), 3.81-3.75 (m, 1H), 2.85 (t, J=8.0 Hz, 1H), 2.49-2.39 (m, 3H), 2.26-2.11 (m, 1H), 1.71-1.64 (m, 3H), 1.25-1.15 (m, 3H), 0.78 (s, 9H), 0.02 (s, 6H);

LCMS (ESI): m/z 471.6 [M$^+$+1]

Synthesis of 5-benzyl-2-((1S, 2R)-2-hydroxy-1-(1,3,4-oxadiazol-2-yl)propyl)-3-methyl-2,5-diazaspiro[3,4]octan-1-one (C-50)

To a stirring solution of C-49 (1.5 g, 3.19 mmol) in dry THF (30 mL) was added TBAF (1M in THF) (4.78 mL, 1.5 mmol) at 0° C. and stirred at RT for 1 h. After consumption of the starting material (by TLC), the reaction mixture was concentrated under reduced pressure. The crude material was diluted with water (75 mL) and EtOAc (100 mL). The organic layer was washed with water (2×50 mL), brine solution (2×50 mL). The organic layer was dried over anhydrous $Na_2SO_4$, filtered and concentrated under reduced pressure to afford crude compound which was purified by column chromatography by eluting 30% EtOAc/n-hexane to obtained C-50 (500 mg, 44%) as white solid.

$^1$H-NMR: (400 MHz, DMSO-$d_6$): δ 9.26 (s, 1H), 7.37-7.22 (m, 5H), 5.29-5.21 (m, 1H), 4.96-4.75 (m, 1H), 4.33-4.02 (m, 1H), 4.00-3.94 (m, 2H), 3.77-3.70 (m, 2H), 2.91-2.80 (m, 1H), 2.42-2.38 (m, 1H), 2.16-2.08 (m, 2H), 1.80-1.63 (m, 1H), 1.30 (d, J=6.4 Hz, 3H), 1.12 (d, J=6.0 Hz, 3H);

LCMS (ESI): m/z 357.43 [M$^+$+1]
HPLC: 99.61%

Synthesis of 2-((1S,2R)-2-hydroxy-1-(1,3,4-oxadiazol-2-yl)propyl)-3-methyl-2,5-diazaspiro[3,4]octan-1-one (C-51)

To a stirring solution of compound C-50 (420 mg, 1.17 mmol) in methanol (10 mL) was added 10% Pd/C (400 mg) under $N_2$ atmosphere. The reaction mixture was stirred under $H_2$ atmosphere at RT for 3 h. After consumption of the starting material (by TLC), the reaction mixture was filtered through a pad of celite and the pad was washed with methanol (10 mL). Obtained filtrate was concentrated under reduced pressure to afford C-51 (220 mg, 70%) as an off-white solid.

$^1$H-NMR: (500 MHz, DMSO-$d_6$): δ 9.26 (s, 1H), 5.25-5.17 (m, 1H), 4.89-4.69 (m, 1H), 4.28-4.21 (m, 1H), 3.84-3.56 (m, 2H), 2.95-2.79 (m, 2H), 1.99-1.84 (m, 2H), 1.77-1.59 (m, 2H), 1.24-1.10 (m, 6H);

LCMS (ESI): m/z 260 [M$^l$+1]
HPLC: 97.94%

Scheme 18

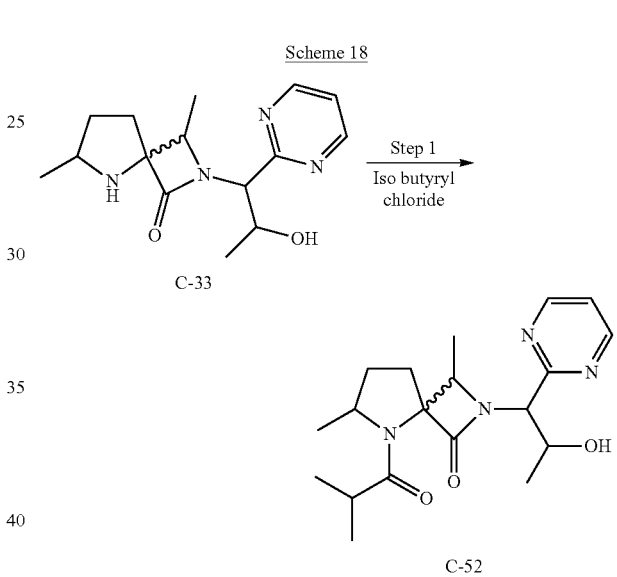

Synthesis of 2-(2-hydroxy-1-(pyrimidin-2-yl)propyl)-3,6-dimethyl-2,5-diazaspiro[3,4]octan-1-one (C-52)

To a stirring solution of C-33 (500 mg, 1.72 mmol) in dry DCM (10 mL) was added DIPEA (556 mg, 4.31 mmol) followed by isobutyryl chloride (273 mg, 2.58 mmol) slowly at 0° C. and stirred at RT for 3 h. After consumption of the starting material (by TLC), the reaction mixture was concentrated under reduced pressure. The crude residue was diluted with water (10 mL). The separated organic layer was washed with brine solution (20 mL). The separated organic layer was dried over anhydrous $Na_2SO_4$ and concentrated under reduced pressure to afford crude compound which was purified by column chromatography by eluting 1% MeOH/DCM to obtained C-52 (90 mg, 14.5%) as pale brown syrup.

$^1$H-NMR: (400 MHz, CD$_3$OD): δ 8.81-8.77 (m, 2H), 7.41-7.37 (m, 1H), 4.63-4.53 (m, 2H), 4.24-4.18 (m, 2H), 2.87-2.72 (m, 1H), 2.33-2.27 (m, 1H), 2.16-2.08 (m, 2H), 1.73-1.69 (m, 1H), 1.40-1.35 (m, 3H), 1.28-1.20 (m, 3H), 1.15-1.02 (m, 9H);

LCMS (ESI): m/z 361.3 [M$^+$+1];
HPLC: 94.85%

Scheme 19

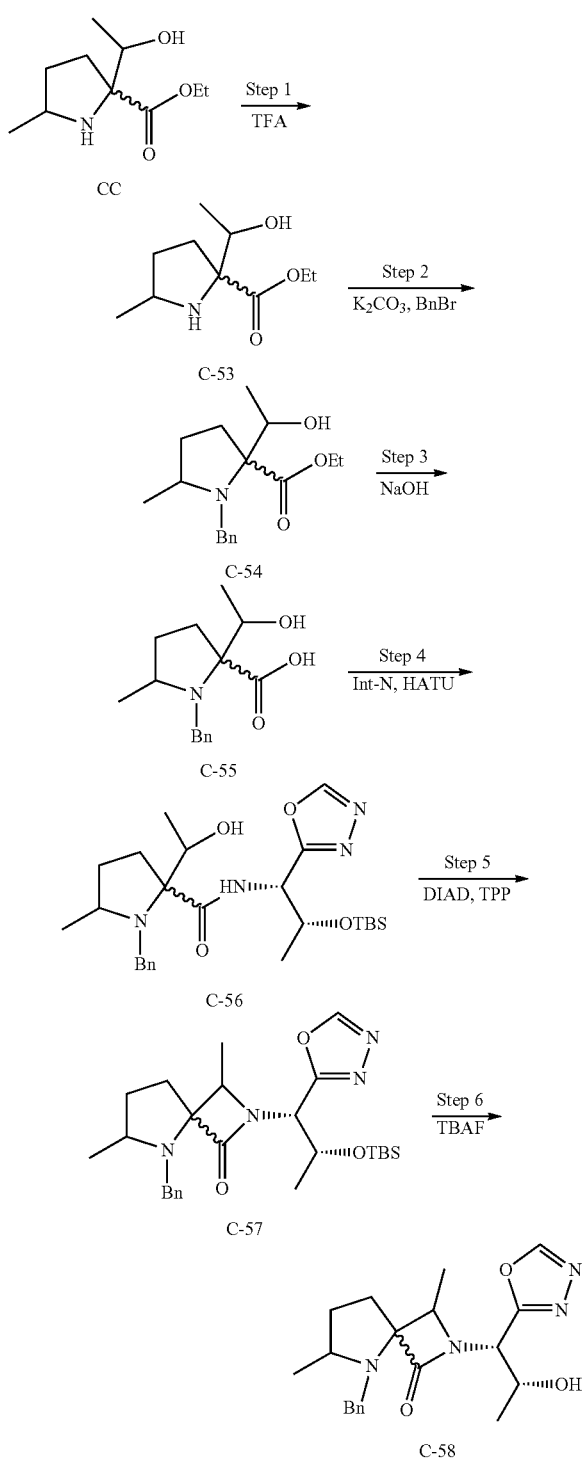

Synthesis of ethyl 2-(1-hydroxyethyl)-5-methylpyrrolidine-2-carboxylate (C-53)

To a stirring solution of CC (5 g, 16.61 mmol) in CH$_2$Cl$_2$ (50 mL) was added TFA (6.34 mL, 83.05 mmol) at 0° C. After being stirred at RT for 4 h, the reaction mixture was concentrated under reduced pressure to afford crude compound which was triturated with n-pentane (50 mL) to obtained C-53 (5 g, crude) as black syrup was directly taken for the next step without further purification.

$^1$H-NMR: (500 MHz, DMSO-d$_6$): δ 8.71 (br s, 1H), 4.29-4.25 (m, 1H), 4.25-4.21 (m, 3H), 4.14-4.03 (m, 1H), 2.31-2.10 (m, 4H), 1.36-1.18 (m, 6H), 1.18-1.10 (m, 3H)

LCMS (ESI): m/z 202.38 [M$^+$+1]

Synthesis of ethyl 1-benzyl-2-(1-hydroxyethyl)-5-methylpyrrolidine-2-carboxylate (C-54: C-54-A & C-54-B)

To a stirring solution of C-53 (5 g (crude), 15.87 mmol) in acetonitrile (50 mL) was added K$_2$CO$_3$ (6.57 g, 47.61 mmol) followed by benzyl bromide (2.82 mL, 23.80 mmol) at RT and stirred for 16 h. After completion of the reaction, diluted the reaction mixture with EtOAc (150 mL) and water (75 mL). The organic layer was washed with brine solution (2×150 mL). The organic layer was dried over anhydrous Na$_2$SO$_4$ and concentrated under vacuum. Obtained crude material was purified by column chromatography eluting with 10%

EtOAc/Hexane to afford 1 g of C-54-A and 1.2 g of C-54-B (separated isomers of C-54) (48%) as yellow syrups.

$^1$H-NMR (C-54-A isomer): (500 MHz, DMSO-d$_6$): δ 7.35-7.14 (m, 5H), 4.55 (s, 2H), 4.24-4.19 (m, 1H), 4.13-4.02 (m, 2H), 3.96-3.91 (m, 2H), 2.14-1.99 (m, 1H), 1.95-1.82 (m, 3H), 1.25-1.18 (m, 3H), 1.10-1.06 (m, 3H), 0.75 (d, J=6.0 Hz, 3H)

LCMS (ESI): m/z 292.3 [M$^+$+1] $^1$H-NMR (C-54-B isomer): (500 MHz, DMSO-d$_6$): δ 7.34-7.18 (m, 5H), 5.15 (t, J=5.5 Hz, 2H), 4.63-4.49 (m, 1H), 4.24-4.22 (m, 1H), 4.10-4.06 (m, 2H), 3.18-3.10 (m, 1H), 2.39-2.33 (m, 1H), 1.89-1.83 (m, 3H), 1.42-1.39 (m, 3H), 1.20-1.13 (m, 3H), 0.76 (d, J=6.0 Hz, 3H)

LCMS (ESI): m/z 292.3 [M$^+$+1]

Synthesis of 1-benzyl-2-(1-hydroxyethyl)-5-methyl-pyrrolidine-2-carboxylic acid (C-55-A)

To a stirring solution of C-54-A (1 g, 3.43 mmol) in MeOH/THF/H$_2$O (5 mL/5 mL/5 mL) were added NaOH (206 mg, 5.14 mmol) at 0° C. The reaction mixture was heated to 90° C. for 6 h. After consumption of the starting material (by TLC), the solvent was evaporated under reduced pressure. The aqueous layer was washed with di ethylether (50 mL). The separated aqueous layer was acidified by using 2N HCl (pH ~3). The aqueous layer was extracted with 10% MeOH/DCM (2×100 mL). The combined organic layer was dried over Na$_2$SO$_4$ and concentrated under reduced pressure to afford compound C-55-A (1 g, crude) as yellow solid.

$^1$H-NMR: (400 MHz, DMSO-d$_6$): δ 9.84 (s, 1H), 7.60 (d, J=6.8 Hz, 2H), 7.50-7.30 (m, 3H), 5.12 (br s, 1H), 4.48-4.35 (m, 2H), 4.09-3.81 (m, 1H), 2.39-2.22 (m, 2H), 2.16-2.08 (m, 2H), 1.66-1.57 (m, 1H), 1.16-0.86 (m, 6H);

LCMS (ESI): m/z 264.3 [M$^+$+1]

Synthesis of 1-benzyl-2-(1-hydroxyethyl)-5-methyl-pyrrolidine-2-carboxylic acid (C-55-B)

To a stirring solution of C-54-B (1.2 g, 4.12 mmol) in MeOH/THF/H$_2$O (5 mL/5 mL/5 mL) were added NaOH (206 mg, 5.14 mmol) at 0° C. The reaction mixture was heated to 90° C. for 6 h. After consumption of the starting material (by TLC), the solvent was evaporated under reduced pressure. The aqueous layer was washed with di ethylether (50 mL). The separated aqueous layer was acidified by using 2N HCl (pH ~3). The aqueous layer was extracted with 10% MeOH/DCM (2×100 mL). The combined organic layer was dried over Na$_2$SO$_4$ and concentrated under reduced pressure to afford compound C-55-B (780 mg) as yellow solid.

$^1$H-NMR (C-55-B isomer): (400 MHz, DMSO-d$_6$): δ 9.14 (s, 1H), 7.64 (d, J=6.0 Hz, 2H), 7.49-7.44 (m, 3H), 4.99 (d, J=12.8 Hz, 1H), 4.48 (s, 2H), 4.45-4.41 (m, 1H), 3.98-3.93 (m, 1H), 2.32-2.13 (m, 4H), 1.40 (d, J=6.4 Hz, 3H), 0.76 (d, J=6.4 Hz, 3H);

LCMS (ESI): m/z 272.4 [M$^+$–1]

Synthesis of 1-benzyl-N-((1S, 2R)-2-((tert-butyldimethylsilyboxy)-1-(1,3,4-oxadiazol-2-yl)propyl)-2-(1-hydroxyethyl)-5-methylpyrrolidine-2-carboxamide (C-56)

To a stirring solution of C-55 (1.78 g, 6.75 mmol)(mixture of two isomers C-55-A & C-55-B) in DMF (10 mL) were added N, N-diisopropylethylamine (3.51 mL, 20.27 mmol), Int N (1.74 g, 6.75 mmol) followed by HATU (3.08 g, 8.11 mmol) at 0° C. and stirred at RT for 16 h. After consumption of the starting material (by TLC), the reaction mixture was diluted with water (100 mL) and EtOAc (150 mL). The separated organic layer was washed with water (100 mL) followed by brine solution (100 mL). The organic layer was dried over anhydrous Na$_2$SO$_4$ and concentrated under reduced pressure to afford crude compound which was purified by column chromatography by eluting 30% EtOAc/n-hexane to obtained C-56 (1.2 g, 35%) as brown syrup.

$^1$H-NMR: (500 MHz, DMSO-d$_6$): δ 9.31 (s, 1H), 8.42 (s, 1H), 7.44-7.19 (m, 5H), 5.26-4.95 (m, 1H), 4.36 (s, 2H), 4.33-4.18 (m, 2H), 4.09-3.94 (m, 1H), 2.32-2.22 (m, 1H), 2.15-1.86 (m, 4H), 1.37-1.05 (m, 9H), 0.85 (s, 9H), 0.04 (s, 6H);

LCMS (ESI): m/z 503.7 [M$^+$+1]

Synthesis of 1-benzyl-N-((1S, 2R)-2-((tert-butyldimethylsilyl)oxy)-1-(1,3,4-oxadiazol-2-yl)propyl)-2-(1-hydroxyethyl)-5-methylpyrrolidine-2-carboxamide (C-57)

To a stirring solution of triphenylphosphine (1.56 g, 5.97 mmol) in dry THF (15 mL) was added DIAD (967 mg, 4.78 mmol) as portionwise and stirred for 15 min at RT. To this precipitated solution added C-56 (1.2 g, 2.39 mmol) in dry THF (15 mL) slowly at RT and stirred for 4 h. After consumption of the starting material (by TLC), the reaction mixture was concentrated under reduced pressure. The obtained solid was triturated with 20% di ehylether/n-hexane (2×100 mL). The filterate was concentrated under reduced pressure to obtained crude compound which was purified by silica gel column chromatography eluting 20% EtOAc/hexane to afford C-57 (400 mg, crude) as brown thick syrup.

$^1$H-NMR: (400 MHz, DMSO-d$_6$): δ 9.27 (s, 1H), 7.43-7.18 (m, 5H), 4.91-4.73 (m, 2H), 4.42-4.02 (m, 2H), 3.96-3.75 (m, 2H), 2.11-1.84 (m, 3H), 1.42-1.37 (m, 1H), 1.35 (d, J=6.0 Hz, 3H), 1.23-1.11 (m, 6H), 0.70 (s, 9H), 0.02 (s, 6H);

LCMS (ESI): m/z 485.7 [M$^+$+1]

Synthesis of 5-benzyl-2-((1S, 2R)-2-hydroxy-1-(1,3,4-oxadiazol-2-yl) propyl)-3,6-dimethyl-2,5-diazaspiro[3,4]octan-1-one (C-58)

To a stirring solution of C-57 (400 mg, 0.82 mmol) in dry THF (5 mL) was added TBAF (1M in THF) (1.23 mL, 1.5 mmol) at 0° C. and stirred for 1 h at RT. After consumption of the starting material (by TLC), the reaction mixture was concentrated under reduced pressure. The crude material was diluted with water (30 mL) and EtOAc (50 mL). The organic layer was washed with water (2×20 mL), brine solution (2×20 mL). The organic layer was dried over anhydrous Na$_2$SO$_4$, filtered and concentrated under reduced pressure to afford crude compound which was purified by column chromatography by eluting 30% EtOAc/n-hexane to obtained C-58 (90 mg, 29%) as thick syrup.

$^1$H-NMR: (400 MHz, DMSO-d$_6$): δ 9.25 (s, 1H), 7.41-7.18 (m, 5H), 5.28-5.17 (m, 1H), 4.97-4.62 (m, 1H), 4.43-4.20 (m, 1H), 4.02-3.89 (m, 1H), 3.77-3.64 (m, 2H), 3.20-3.01 (m, 1H), 2.09-1.80 (m, 3H), 1.44-1.40 (m, 1H), 1.38-1.30 (m, 1H), 1.28-1.21 (m, 4H), 1.19-1.06 (m, 1H), 0.90-0.85 (m, 3H)

LCMS (ESI): m/z 371.45 [M$^+$+1]

HPLC: 94.53%

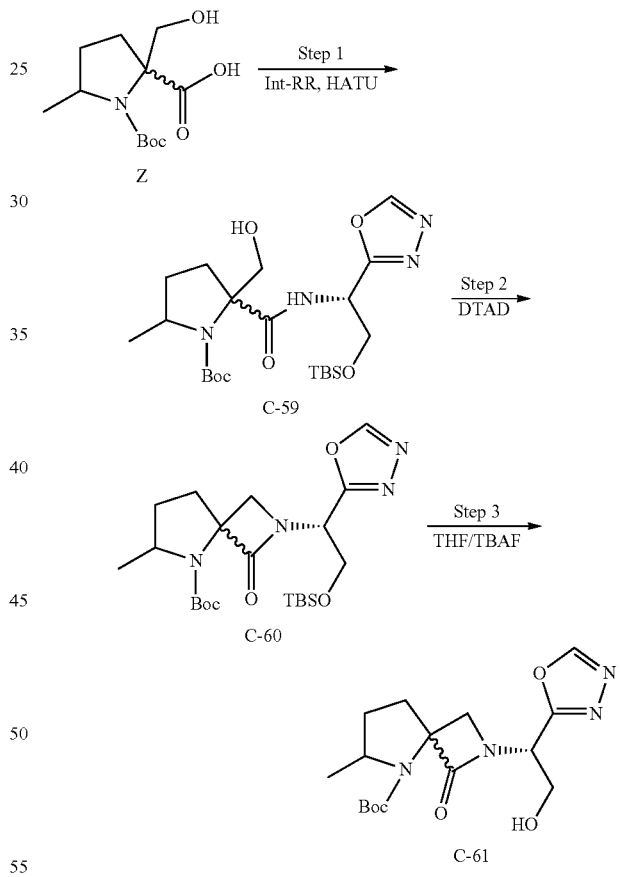

Scheme 20

Synthesis of tert-butyl 2-(((S)-2-((tert-butyldimethylsilyboxy)-1-(1,3,4-oxadiazol-2-yl)ethyl)carbamoyl)-2-(hydroxymethyl)-5-methylpyrrolidine-1-carboxylate (C-59)

To a stirring solution of Z (2 g, 7.72 mmol) in DCM (25 mL) were added N,N-diisopropylethylamine (4 mL, 23.16 mmol), Int RR (2.06 g, 8.49 mmol), followed by HATU (3.52 g, 9.26 mmol) at 0° C. and stirred at RT for 16 h. After consumption of the starting material (by TLC), the reaction mixture was diluted with water (50 mL). The separated organic layer was washed with citric acid solution (1×50 mL), saturated brine solution (1×50 mL). The separated organic layer was dried over anhydrous Na$_2$SO$_4$ and concentrated under reduced pressure to afford crude compound which was purified by column chromatography by eluting 50% EtOAc/n-hexane to obtained C-59 (2.5 g, 67%) as thick syrup.

$^1$H-NMR: (500 MHz, DMSO-d$_6$): δ 9.25 (s, 1H), 7.99 (d, J=3.5 Hz, 1H), 5.29-5.26 (m, 2H), 4.05-3.99 (m, 3H), 3.57-3.54 (m, 2H), 2.28-1.91 (m, 3H), 1.42 (s, 9H), 1.38-1.31 (m, 1H), 1.18-1.11 (m, 3H), 0.84 (s, 9H), −0.01 (s, 6H)

Synthesis of tert-butyl 2-((S)-2-((tert-butyldimethyl-silyboxy)-1-(1,3,4-oxadiazol-2-yl)ethyl)-6-methyl-1-oxo-2,5-diazaspiro[3,4]octane-5-carboxylate (C-60)

To a stirring solution of triphenylphosphine (2.7 g, 10.33 mmol) in dry THF (20 mL) was added DTAD (2.37 g, 10.33 mmol) at RT and stirred for 15 min. After added C-59 (2.5 g, 5.16 mmol) and the reaction mixture was stirred at RT for 3 h. After consumption of the starting material (by TLC), the reaction mixture was concentrated under reduced pressure. The crude material was triturated with di ethylether/n-pentane and obtained solid was filtered. The filtrate was evaporated, purified by silica gel column chromatography eluting 30% EtOAc/hexane to afford C-60 (2.1 g, 87.5%) as yellow liquid.

$^1$H-NMR: (500 MHz, DMSO-d$_6$): δ 9.32 (s, 1H), 5.19-5.08 (m, 1H), 4.12-3.87 (m, 3H), 3.58-3.45 (m, 2H), 1.56-1.42 (m, 3H), 1.40 (s, 9H), 1.38-1.20 (m, 1H), 1.18-1.12 (m, 3H), 0.80 (s, 9H), 0.02 (s, 6H)

Synthesis of tert-butyl 2-(2-hydroxy-1-(pyrimidin-2-yl)propyl)-6-methyl-1-oxo-2,5-diazaspiro[3,4]octane-5-carboxylate (C-61)

To a stirring solution of C-60 (2.1 g, 4.5 mmol) in dry THF (10 mL) was added TBAF (2.34 g, 9 mmol) at 0° C. The reaction mixture was stirred at RT for 3 h. After consumption of the starting material (by TLC), the reaction mixture was concentrated under reduced pressure. The crude material was purified by silica gel column chromatography eluting 2% MeOH/DCM to afford C-61 (800 mg, 51%) as thick syrup.

$^1$H-NMR: (400 MHz, DMSO-d$_6$): δ 9.25 (s, 1H), 5.33-5.08 (m, 2H), 3.94-3.75 (m, 3H), 3.67-3.51 (m, 1H), 3.39-3.31 (m, 1H), 2.13-1.93 (m, 3H), 1.55-1.50 (m, 1H), 1.40 (s, 9H), 1.15-1.08 (m, 3H),

LCMS (ESI): m/z 353.3 [M$^+$+1];
HPLC: 96.6%

Scheme 21

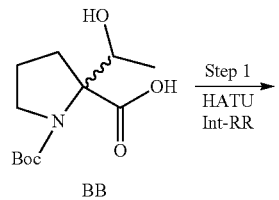

BB

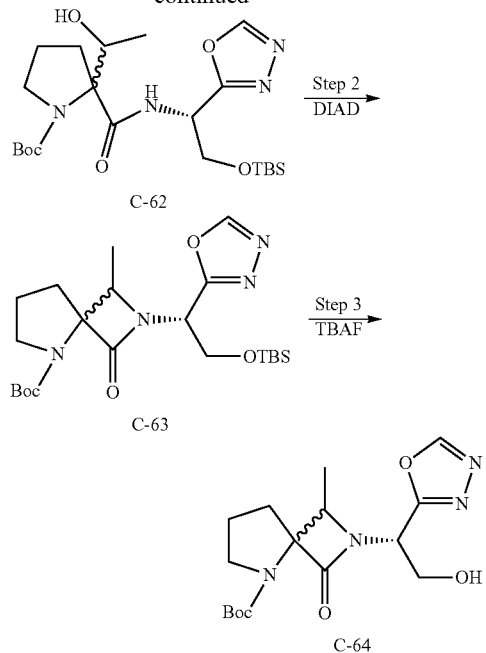

Synthesis of tert-butyl 2-(((S)-2-((tert-butyldimethylsilyl)oxy)-1-(1,3,4-oxadiazol-2-yl)ethyl)carbamoyl)-2-(1-hydroxyethyl) pyrrolidine-1-carboxylate (C-62)

To a stirring solution of BB (3.5 g, 13.51 mmol) in CH$_2$Cl$_2$ (40 mL) were added DIPEA (7.0 mL, 40.53 mmol), RR (3.2 g, 13.51 mmol), HATU (5.6 g, 14.85 mmol) at 0° C. and stirred for 12 h. After consumption of the starting material (by TLC), the reaction mixture was diluted with water (30 mL) and extracted with CH$_2$Cl$_2$ (2×100 mL). The separated organic layer was washed with brine, dried over anhydrous Na$_2$SO$_4$, filtered and concentrated under reduced pressure to afford C-62 (3.5 g, crude) as colorless liquid.

Mass (ESI): m/z 485.67 [M$^l$+1]

Synthesis of tert-butyl 2-((S)-2-((tert-butyldimethylsilyl) oxy)-1-(1,3,4-oxadiazol-2-yl)ethyl)-1-methyl-3-oxo-2,5-diazaspiro[3,4]octane-5-carboxylate (C-63)

To a stirring solution of triphenylphosphine (2.03 g, 7.75 mmol) in THF (25 mL) was added DIAD (1.59 g, 7.75 mmol) at 0° C. and stirred for 30 min. C-62 (1.5 g, 3.10 mmol) in THF (10 mL) was added dropwise and the reaction mixture was stirred at RT for 16 h. After consumption of the starting material (by TLC), the reaction was concentrated under reduced pressure. The crude material was purified by silica gel column chromatography eluting 30% EtOAc/hexane to afford C-63 (600 mg, 43%) as pale yellow liquid.

$^1$H-NMR: (500 MHz, DMSO-d$_6$): δ 9.24 (s, 1H), 5.93-4.75 (m, 2H), 4.16-3.91 (m, 2H), 3.78-3.70 (m, 2H), 3.91 (d, J=7.0 Hz, 1H), 3.77 (d, J=7.0 Hz, 2H), 3.44-3.34 (m, 4H), 2.01-1.91 (m, 2H), 1.85-1.68 (m, 6H), 2.11-1.68 (m, 4H), 1.40 (s, 9H), 1.38-1.18 (m, 3H), 0.80 (s, 9H), −0.02 (s, 6H).

Mass (ESI): m/z 467.6 [M$^+$+1]

Synthesis of tert-butyl 2-((S)-2-hydroxy-1-(1,3,4-oxadiazol-2-yl)ethyl)-1-methyl-3-oxo-2,5-diazaspiro[3,4]octane-5-carboxylate (C-64)

To a stirring solution of C-63 (0.5 g, 1.07 mmol) in dry THF (10 mL) was added TBAF (1M in THF) (1.07 mL, 1.91 mmol) at 0° C. and stirred at RT for 3 h. After consumption of the starting material (by TLC), the reaction mixture was concentrated under reduced pressure. The crude material was diluted with water (15 mL) and EtOAc (30 mL). The organic layer was washed with water (2×15 mL), brine solution (2×10 mL). The organic layer was dried over anhydrous $Na_2SO_4$, filtered and concentrated under reduced pressure to afford crude compound which was purified by column chromatography by eluting 70% EtOAc/n-hexane to obtained C-64 (95 mg, 25%) as white solid.

$^1$H-NMR: (400 MHz, DMSO-$d_6$): δ 9.26 (s, 1H), 5.32-5.04 (m, 2H), 3.98-3.72 (m, 4H), 2.14-1.66 (m, 4H), 1.39 (s, 1H), 1.37-1.09 (m, 3H)
LCMS (ESI): m/z 353.3 [M$^+$+1]
HPLC: 88.9%

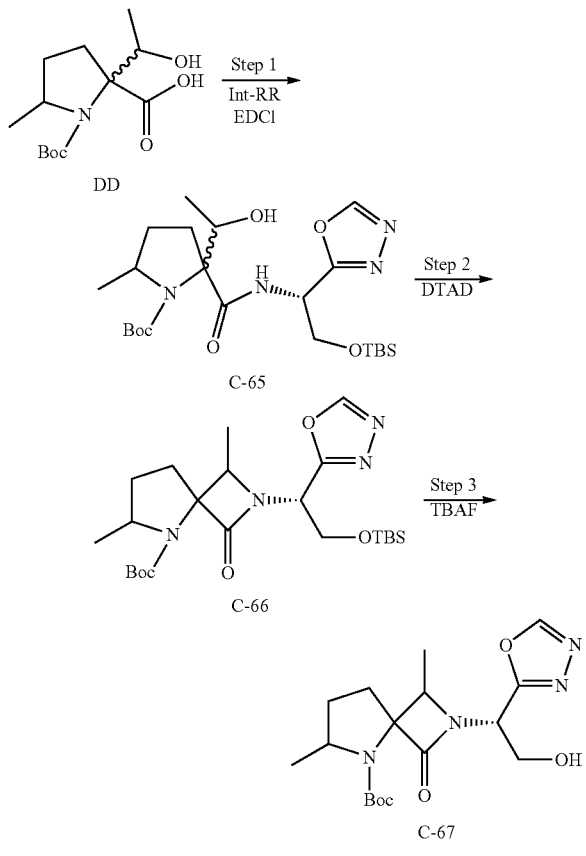

Scheme 22

C-65

C-66

C-67

Synthesis of tert-butyl 2-(((S)-2-((tert-butyldimethylsilyboxy)-1-(1,3,4-oxadiazol-2-yl)ethyl)carbamoyl)-2-(1-hydroxyethyl)-5-methylpyrrolidine-1-carboxylate (C-65)

To a stirring solution of DD (1 g, 3.66 mmol) in DCM (20 mL) were added N,N-diisopropylethylamine (1.9 mL, 10.98 mmol), Int RR (978 mg, 4.02 mmol), EDCI (1.04 g, 5.49 mmol) followed by HOBT (741 mg, 5.49 mmol) at 0° C. and stirred at RT for 16 h. After consumption of the starting material (by TLC), the reaction mixture was diluted with water (20 mL). The separated organic layer was washed with brine solution (30 mL). The separated organic layer was dried over anhydrous $Na_2SO_4$ and concentrated under reduced pressure to afford crude compound which was purified by column chromatography by eluting 40% EtOAc/n-hexane to obtained C-65 (700 mg, 38.4%) as thick syrup.

$^1$H-NMR: (500 MHz, DMSO-$d_6$): δ 9.26 (s, 1H), 5.22-5.18 (m, 1H), 4.58-4.50 (m, 2H), 4.04-3.92 (m, 3H), 1.47-1.41 (m, 1H), 1.38 (s, 9H), 1.29-1.16 (m, 6H), 1.14-1.11 (m, 3H), 0.83 (s, 9H), −0.02 (s, 6H);
LCMS (ESI): m/z 523.6 [M$^+$+1]

Synthesis of tert-butyl 2-((S)-2-((tert-butyldimethylsilyboxy)-1-(1,3,4-oxadiazol-2-yl)ethyl)-1,6-dimethyl-3-oxo-2,5-diazaspiro[3.4]octane-5-carboxylate (C-66)

To a stirring solution of triphenylphosphine (736 mg, 2.81 mmol) in dry THF (10 mL) was added DTAD (646 mg, 2.81 mmol) as portionwise and stirred for 15 min at RT. To this precipitated solution added C-65 (700 mg, 1.4 mmol) in dry THF (15 mL) slowly at RT and stirred for 6 h. After consumption of the starting material (by TLC), the reaction mixture was concentrated under reduced pressure. The crude material was triturated with n-pentane (20 mL)/diethylether (20 mL). The filtrate was concentrated under reduced pressure to obtained crude compound which was purified by silica gel column chromatography eluting 25% EtOAc/hexane to afford C-66 (430 mg, 64%) as thick syrup.

$^1$H-NMR: (400 MHz, DMSO-$d_6$): δ 9.25 (s, 1H), 5.20-5.16 (m, 1H), 4.16-4.00 (m, 1H), 3.88-3.70 (m, 3H), 2.17-2.08 (m, 1H), 1.96-1.85 (m, 1H), 1.40 (s, 9H), 1.26-1.07 (m, 8H), 0.82 (s, 9H), −0.02 (s, 6H);
LCMS (ESI): m/z 505.5 [M$^+$+1]

Synthesis of tert-butyl 2-((S)-2-hydroxy-1-(1,3,4-oxadiazol-2-yl)ethyl)-1,6-dimethyl-3-oxo-2,5-diazaspiro[3,4]octane-5-carboxylate (C-67)

To a stirring solution of C-66 (430 mg, 0.89 mmol) in dry THF (10 mL) was added TBAF (1.8 mL, 1.79 mmol) slowly at 0° C. and stirred at RT for 6 h. After consumption of the starting material (by TLC), the reaction mixture was concentrated under reduced pressure. The crude residue was purified with column chromatography by eluting 90% EtOAc/n-hexane to afford C-67 (80 mg, 24.5%) as thick syrup.

$^1$H-NMR: (400 MHz, DMSO-$d_6$): δ 9.25 (s, 1H), 5.20-5.03 (m, 2H), 3.98-3.72 (m, 3H), 2.50-1.85 (m, 3H), 1.56-1.50 (m, 1H), 1.40 (s, 9H), 1.27-1.11 (m, 6H)
LCMS (ESI): m/z 291.3 [M$^+$+1];
HPLC: 91.4%

Example 3—[$^3$H] MK-801 Binding Assay

Methods
Assays were conducted as described in Moskal et al. (Moskal, J. R., Kuo, A. G., Weiss, C., Wood, P. L., O'Connor Hanson, A., Kelso, S., Harris, R. B., Disterhoft, J. F., 2005. GLYX-13: a monoclonal antibody-derived peptide that acts as an N-methyl-D-aspartate receptor modulator. Neuropharmacology. 49, 1077-87) The potentiation of [³H]MK-801 binding (5 nM; 22.5 Ci/mmol) to well washed rat cortical membranes (200 µg) was measured under non-equilibrium conditions (15 min @25° C.) in the presence of increasing concentrations of test compounds and 50 µM glutamate. Zero levels were determined in the absence of any glycine ligand and in the presence of 30 µM 5,7 DCKA. Maximal stimulation was measured in the presence of 1 mM glycine, and 50 µM glutamate was present in all samples. The facilitation of [³H]MK-801 binding by tests compounds was calculated by using a 3 parameter log agonist vs. response equation (Graph pad Prism, USA) and potency (EC$_{50}$, expressed in pM) and maximal activity (% maximal stimulation) were calculated for the test compound.

Results

The potency and maximal activity for Compound Y is 288 pM, 14%.

TABLE 2

Additional Biological Data

| Compound | Unified Activity Data: LTP Augmentation (Percent) | Unified Activity Data: LTP Concentration (uM) | Unified Activity Data: LTP, Significant (S) or Non-significant (NS) | Unified Activity Data: Porsolt Floating Time Inhibition (Percent) | Unified Activity Data: Porsolt Dose (mg/kg) | Unified Activity Data: Porsolt Dose, route | Unified Activity Data: Porsolt Time Post Dose (Hours) | MK-801 Glycine Site Binding Assay: Rat Cortex EC50 (M) |
|---|---|---|---|---|---|---|---|---|
| C-4 | 140 | 1 | S | 92 | 3 | IV | 1 | 2.879E−10 |
| C-15 | 120 | 1 | S | 86 | 1 | PO | 1 | |

TABLE 3

Additional Biological Data

| Compound | MK-801 Glycine Site Binding Assay: Rat Cortex EC50 (M) | LTP: LTP Augmentation (%) | LTP: LTP Concentration (uM) | LTP: LTP Significance, S or NS |
|---|---|---|---|---|
| C-33 | 7.129E−12 | 30 | 1 | NS |
| C-19 | 1.096E−10 | 110 | 1 | S |
| C-26 | 7.23E−13 | 65 | 1 | NS |
| C-29 | 1.353E−10 | 125 | 1 | S |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound represented by formula I:

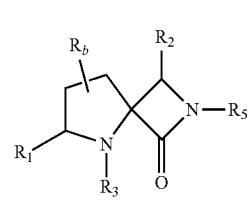

or a pharmaceutically acceptable salt, a stereoisomer, and/or an N-oxide thereof, wherein $R_b$ is selected from the group consisting of H, halogen, hydroxyl, cyano and $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

$R_5$ is X or —$C_1$-$C_6$ alkylene-X, wherein X is selected from the group consisting of:

(i) heteroaryl including from 5 to 6 ring atoms wherein 1, 2, or 3 of the ring atoms are independently selected from the group consisting of N, O, and S; and (ii) heterocyclyl including from 3 to 6 ring atoms wherein 1, 2, or 3 of the ring atoms are independently selected from the group consisting of N, O, and S;

wherein $R_5$ is optionally substituted with

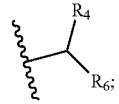

and $R_6$ is selected from the group consisting of H, halogen, hydroxyl, cyano, —O—C(O)—$C_1$-$C_6$ alkyl, $C_1$-$C_6$ alkyl, and $C_1$-$C_6$ alkoxy.

2. The compound of claim 1, wherein $R_1$ is H.

3. The compound of claim 1, wherein $R_2$ is H.

4. The compound of claim 1, wherein $R_3$ is H.

5. The compound of claim 1, wherein $R_3$ is a nitrogen protecting group.

6. The compound of claim 5, wherein $R_3$ has formula —C(O)OR$_{31}$, wherein $R_{31}$ is selected from the group consisting of $C_1$-$C_6$alkyl, $C_1$-$C_6$ haloalkyl, $C_2$-$C_6$ alkenyl, $C_2$-$C_6$alkynyl, $C_3$-$C_{10}$ cycloalkyl, —$CH_2$—$C_3$-$C_{10}$ cycloalkyl, —$CH_2$-phenyl, and $CH_2$-pyridyl, wherein $C_3$-$C_{10}$ cycloalkyl is optionally substituted with from 1-3 independently selected $C_1$-$C_3$ alkyl, and wherein phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, $SO_2Me$, cyano and —$OC(O)CH_3$.

7. The compound of claim 6, wherein $R_{31}$ is $C_1$-$C_6$ alkyl.

8. The compound of claim 7, wherein $R_{31}$ is tert-butyl.

9. The compound of claim 5, wherein $R_3$ has formula —$C(O)R_{32}$, wherein $R_{32}$ is selected from the group consisting of H, $C_1$-$C_6$ alkyl, $C_1$-$C_6$ haloalkyl, phenyl, and pyridyl, wherein phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, $SO_2Me$, cyano and —$OC(O)CH_3$.

10. The compound of claim 9, wherein $R_{32}$ is $C_1$-$C_6$ alkyl.

11. The compound of claim 10, wherein $R_{32}$ is —$CH_3$ or iso-propyl.

12. The compound of claim 1, wherein $R_5$ is X.

13. The compound of claim 10, wherein X is heteroaryl including from 5 to 6 ring atoms wherein 1, 2, or 3 of the ring atoms are independently selected from the group consisting of N, O, and S.

14. The compound of claim 13, wherein X is selected from the group consisting of 1,2,4-oxadiazolyl, 1,3,4-oxadiazolyl, pyridyl, and pyrimidinyl.

15. The compound of claim 12, wherein $R_5$ is substituted with —$CH(R_4)(R_6)$.

16. The compound of claim 15, wherein $R_4$ is $C_1$-$C_6$ alkyl.

17. The compound of claim 15, wherein $R_4$ is methyl.

18. The compound of claim 15, wherein $R_6$ is selected from the group consisting of hydroxyl, —O—C(O)—$C_1$-$C_6$ alkyl, and $C_1$-$C_6$ alkoxy.

19. The compound of claim 18, wherein $R_6$ is hydroxyl.

20. The compound of claim 1, wherein $R_5$ is —$C_1$-$C_6$ alkylene-X.

21. The compound of claim 1, wherein $R_5$ is —$C_1$-$C_2$ alkylene-X.

22. The compound of claim 21, wherein $R_5$ is substituted with —$CH(R_4)(R_6)$.

23. The compound of claim 22, wherein $R_5$ is substituted on the alkylene portion with —$CH(R_4)(R_6)$.

24. The compound of claim 23, wherein $R_5$ has the formula —$CH(CHR_4R_6)$—X.

25. The compound of claim 22, wherein $R_4$ is $C_1$-$C_6$ alkyl.

26. The compound of claim 22, wherein $R_4$ is methyl.

27. The compound of claim 22, wherein $R_6$ is selected from the group consisting of hydroxyl, —O—C(O)—$C_1$-$C_6$ alkyl, and $C_1$-$C_6$ alkoxy.

28. The compound of claim 27, wherein $R_6$ is hydroxyl.

29. The compound of claim 20, wherein X is heteroaryl including from 5 to 6 ring atoms wherein 1, 2, or 3 of the ring atoms are independently selected from the group consisting of N, O, and S.

30. The compound of claim 20, wherein X is selected from the group consisting of 1,2,4-oxadiazolyl, 1,3,4-oxadiazolyl, pyridyl, and pyrimidinyl.

31. The compound of claim 1, wherein $R_b$ is H.

32. The compound of claim 1, wherein the compound is selected from the group consisting of

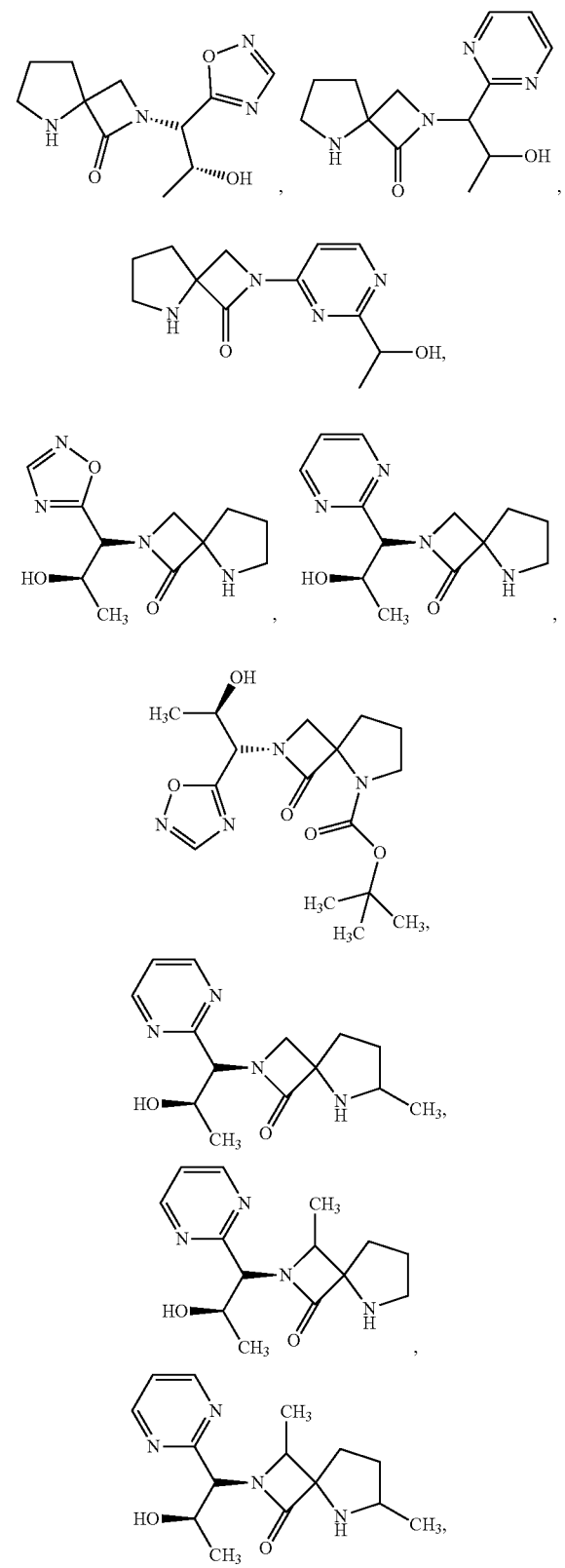

-continued

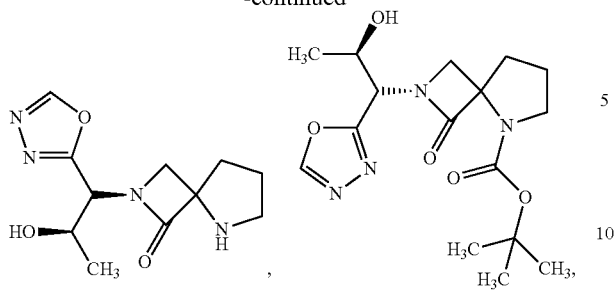

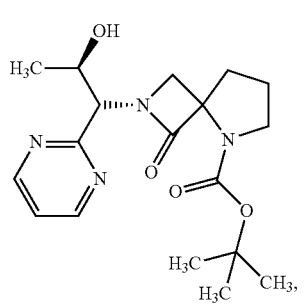

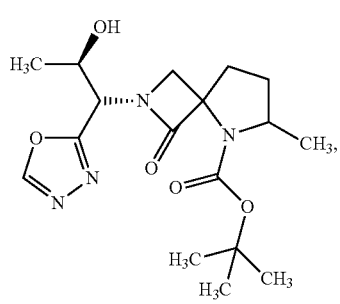

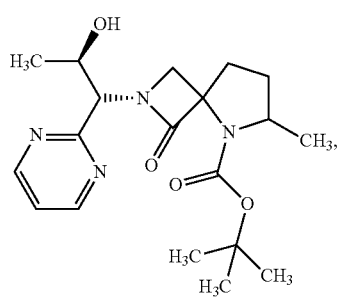

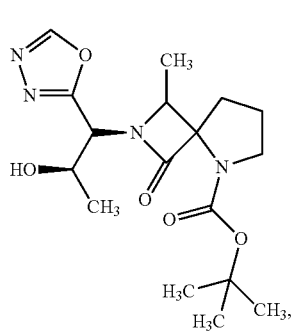

-continued

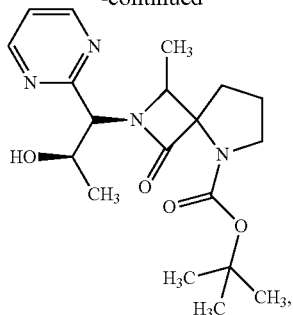

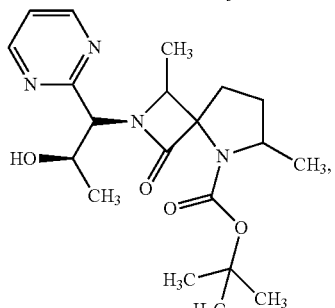

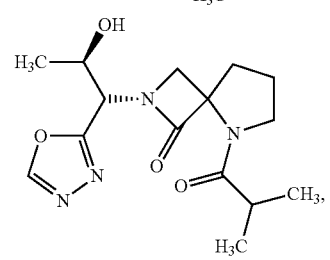

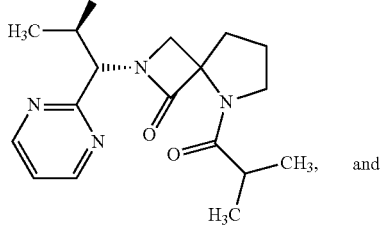, and

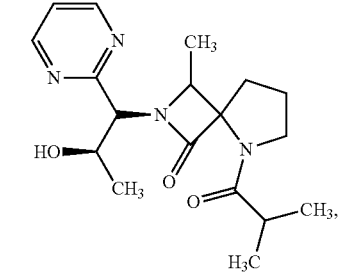

or a pharmaceutically acceptable salt, a stereoisomer, and/or an N-oxide thereof.

33. A pharmaceutical composition comprising a compound of claim 1, and a pharmaceutically acceptable excipient.

34. The pharmaceutical composition of claim 33, suitable for oral administration.

35. The pharmaceutical composition of claim 33, suitable for intravenous administration.

36. A method of treating of treating depression, Alzheimer's disease, attention deficit disorder, schizophrenia, or anxiety, in a patient in need thereof, the method comprising:

administering to said patient a pharmaceutically effective amount of a compound of claim 1.

37. A compound represented by formula I:

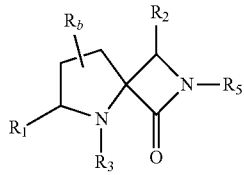
(I)

or a pharmaceutically acceptable salt, a stereoisomer, and/or an N-oxide thereof, wherein $R_b$ is selected from the group consisting of H, halogen, hydroxyl, cyano or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

$R_5$ is X or —$C_1$-$C_6$ alkylene-X, wherein X is selected from the group consisting of a 4- to 6-membered heteroaryl ring having 1, 2, or 3 heteroatoms selected from O, S, and N, and a 4- to 6-membered heterocyclyl ring having 1, 2, or 3 heteroatoms selected from O, S, and N, and wherein $R_5$ is optionally substituted with

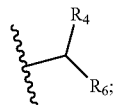

and $R_6$ is selected from the group consisting of H, halogen, hydroxyl, cyano, —O—C(O)—$C_1$-$C_6$ alkyl, $C_1$-$C_6$ alkyl, and $C_1$-$C_6$ alkoxy.

38. The compound of claim 37, wherein $R_1$ is H.

39. The compound of claim 37, wherein $R_2$ is H.

40. The compound of claim 37, wherein $R_3$ is H.

41. The compound of claim 37, wherein $R_4$ is $C_1$-$C_6$ alkyl.

42. The compound of claim 37, wherein $R_4$ is methyl.

43. The compound of claim 37, wherein $R_5$ is X, and wherein X is a 5- to 6-membered heteroaryl ring selected from the group consisting of azetidine, pyrrolidine, pyrazolidine, pyridine, pyrimidine, isooxazolidine, imidazolidine, oxazolidine, thiazolidine, and isothiazolidine.

44. The compound of claim 37, wherein $R_5$ is

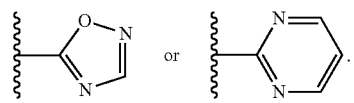

45. The compound of claim 37, wherein $R_5$ is X, and wherein X is optionally substituted with

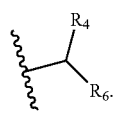

46. The compound of claim 37, wherein $R_6$ is hydroxyl.

47. The compound of claim 37, wherein the compound is

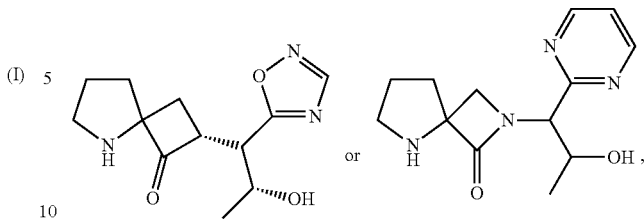

or a pharmaceutically acceptable salt, a stereoisomer, and/or an N-oxide thereof.

48. A compound represented by formula II:

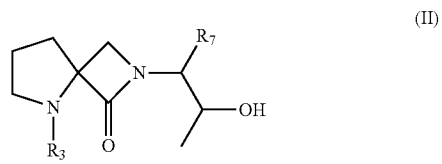
(II)

or a pharmaceutically acceptable salt, a stereoisomer, and/or an N-oxide thereof, wherein $R_3$ is selected from the group consisting of H, $C_1$-$C_6$ alkyl and a nitrogen protecting group; and $R_7$ is a 4- to 6-membered heteroaryl ring having 1, 2, or 3 heteroatoms selected from O, S, and N, optionally substituted on a free carbon by a substituent selected from the group consisting of halogen, $C_1$-$C_6$ alkyl, hydroxyl, cyano, and phenyl.

49. A compound represented by formula III:

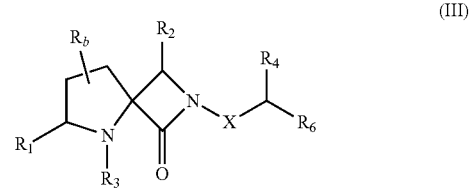
(III)

or a pharmaceutically acceptable salt, a stereoisomer, and/or an N-oxide thereof, wherein $R_b$ is selected from the group consisting of H, halogen, hydroxyl, cyano and $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ is H or $C_1$-$C_6$ alkyl;

X is selected from the group consisting of a 4- to 6-membered heteroaryl ring having 1, 2, or 3 heteroatoms selected from O, S, and N, and a 4- to 6-membered heterocyclyl ring having 1, 2, or 3 heteroatoms selected from O, S, and N, wherein

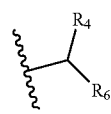

is present on a free carbon of X; and $R_6$ is selected from the group consisting of H, halogen, hydroxyl, cyano, —O—C(O)—$C_1$-$C_6$ alkyl, $C_1$-$C_6$ alkyl, and $C_1$-$C_6$ alkoxy.

50. The compound of claim 49, wherein R₁ is H.
51. The compound of claim 49, wherein R₂ is H.
52. The compound of claim 49, wherein R₃ is H.
53. The compound of claim 49, wherein R₄ is C₁-C₆ alkyl.
54. The compound of claim 49, wherein R₄ is methyl.
55. The compound of claim 49, wherein R_b is H.
56. The compound of claim 49, wherein X is

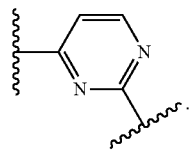 [SMILES: *c1ccnc(*)n1]

57. The compound of claim 49, wherein R₆ is hydroxyl.
58. The compound of claim 49, wherein the compound is

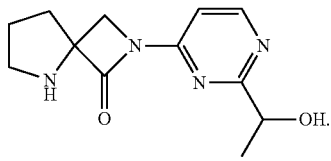 [SMILES: CC(O)c1nccc(N2CC3(CCCN3)C2=O)n1]

59. A pharmaceutical composition comprising a compound of claim 37, and a pharmaceutically acceptable excipient.
60. The pharmaceutical composition of claim 59, suitable for oral administration.
61. The pharmaceutical composition of claim 59, suitable for intravenous administration.
62. A method of treating of treating depression, Alzheimer's disease, attention deficit disorder, schizophrenia, or anxiety, in a patient in need thereof, the method comprising:
administering to said patient a pharmaceutically effective amount of a compound of claim 37.
63. The compound of claim 1, wherein the compound is

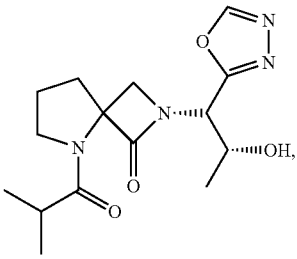

or a pharmaceutically acceptable salt, a stereoisomer, and/or an N-oxide thereof.

* * * * *